(12) United States Patent
Davis et al.

(10) Patent No.: US 7,085,689 B2
(45) Date of Patent: Aug. 1, 2006

(54) METHOD AND APPARATUS FOR CREATING A SIMULATED PARTICLE PACK

(75) Inventors: I. Lee Davis, Honeyville, UT (US); Micheal P. Iverson, Brigham City, UT (US)

(73) Assignee: Alliant Techsystems Inc., Edina, MN (US)

( * ) Notice: Subject to any disclaimer, the term of this patent is extended or adjusted under 35 U.S.C. 154(b) by 892 days.

(21) Appl. No.: 09/805,606

(22) Filed: Mar. 12, 2001

(65) Prior Publication Data

US 2003/0097244 A1 May 22, 2003

(51) Int. Cl.
*G06F 7/60* (2006.01)
*G06F 17/10* (2006.01)
*G06F 101/00* (2006.01)

(52) U.S. Cl. .................................. 703/2; 703/1; 703/7
(58) Field of Classification Search ................. 703/1–2, 703/6–12, 24
See application file for complete search history.

(56) References Cited

PUBLICATIONS

Fu et al, "Particle Packing by Kinematics and Dynamics Simulations," American Society of Civil Engineers, 14th Engineering Mechanics Conference, pp. 1–5 (May 2000)(paper available at http://www.ce.utexas.edu/em/2000/).*

Sutou et al, "A Study of the Global Optimization [sic] Approach to Spherical Packing Problems," Research Reports on Mathematical and Computing Sciences, Series B: Operations Research, pp. 1–26 (May 2000)(paper available at http://citeseer.ist.psu.edu/sut.*

Torquato et al, "Is Random Close Packing of Spheres Well Defined?" Physical Review Letters, vol. 84 No. 10, pp. 2064–2067 (Mar. 2000).*

Nandakumar et al, "Predicting Geometrical Properties of Random Packed Beds from Computer Simulation," American Institute of Chemical Engineers, AIChE Journal, vol. 45 No. 11, pp. 2286–2297 (Nov. 1999).*

Ortega et al, "Optimizing Particle Packing in Powder Consolidation," American Ceramic Society Bulletin, vol. 78 No. 8, pp. 106–111 (Aug. 1999).*

I. Lee Davis et al., Random particle packing by reduced dimension algorithms, J. Appl. Phys. 67 (2), Jan. 15, 1990, pp. 1022–1029.

* cited by examiner

*Primary Examiner*—Samuel Broda
(74) *Attorney, Agent, or Firm*—TraskBritt

(57) ABSTRACT

A machine-implemented method is provided for placing a plurality of particles to create a simulated particle pack. The method comprises defining a central string, a space disposed about the central string, and N concentric subspaces disposed about the central string and within the space, each of the N subspaces corresponding to one of the N particle categories, selecting a particle from the plurality of particles, and placing the selected particle in the corresponding subspace so that the selected particle becomes a placed particle at a particle location unique to that placed particle and is in non-overlapping relation with other placed particles. The selected particle placement includes defining a catch net representative of buoyancy of a portion of the placed particles and positioning the catch net within the space based upon the placement of the portion of the placed particles. The selected particle placement further includes defining a water level representative of a level of a portion of the placed particles that are smaller than the selected particle and represent a surface of the smaller placed particles. The selected particle is placed in non-overlapping relation with respect to the catch net and the water level. The method further includes positioning the water level within the space based upon the smaller particle surface. The particle selection and placement procedures are repeated until a desired number of particles have been placed. Related apparatus also are disclosed.

50 Claims, 4 Drawing Sheets

METHOD AND APPARATUS FOR CREATING A SIMULATED PARTICLE PACK

BACKGROUND OF THE INVENTION

1. Field of the Invention

The present invention relates to computerized methods and apparatus for creating particle packs and, more specifically, to computerized methods and apparatus for creating particle packs with enhanced speed and processing efficiency.

2. Description of the Related Art

The present invention relates to the creation of particle packs that can be used to model or simulate particle containing or particle filled systems. There are many varieties of particle containing systems. Specific yet merely illustrative examples are found in the fields of asphalts, concretes, ceramics, soils, chemical physics of amorphous materials, slurry mechanics, and solid propellants or gas generators. An important class of such systems comprises polymeric materials with particles embedded or embodied in the polymer body or binder.

It is highly desirable in many circumstances to have a capability to model or simulate the properties, performance, etc. of such particle containing systems. In designing such particle filled systems, for example, substantial trial and error can be avoided if one is able to use a model or simulation to assess the implications of making changes in the components, their configuration, the conditions, etc.

This is particularly true in microstructural analyses, e.g., wherein the analysis focuses on the material at a highly magnified level, such as at the molecular or grain stages. A specific example of microstructural analysis would involve the modeling or simulation of a particle pack for a propellant, which typically would include fuel and oxidizer particles in a polymeric binder. When modeling or simulating a particle containing system, it has become customary to construct an analytical replica or representation of the particle filled material, which is generally referred to as a particle pack. The term "particle pack" has come to be used in the field to refer generally to a collection of particles in a defined volume.

The general object in creating particle packs is to model or simulate the manner in which a plurality of particles, usually a large number of such particles, will fill or otherwise occupy a particular space. The nature of the particles may vary, in some cases considerably, depending on the particular application. These variations may include particle size variations, as well as other characteristics.

The complexity of models used to simulate real world particle containing systems increases dramatically if more than a limited number of variables are considered. The numbers of interactions, combinations and permutations brought to bear by anything other than relatively simple systems causes the processing requirements to become unwieldy even for the most advanced computer systems. This complexity and processing requirement limitation is even more pronounced for systems that employ large numbers of particles.

These limitations have caused workers in the field to invoke various simplifying assumptions to render the problem more workable. One such assumption involves the shape of the particle. The complexity and related processing demands can be substantially reduced, for example, if one assumes that the particles are spherical.

The general approach to simulating particle containing systems in the past has involved a more rigorous one in which a particle pack is constructed by placing the individual particles into a three dimensional volume, i.e., into a "full field." This approach in theory offers promise for accurate simulation of the real particle containing systems. The large number of particles required to construct a statistically meaningful or useful particle pack, however, usually renders this approach impractical. The processing power required to construct such a particle pack is prohibitive for all but extremely small numbers of particles, and only relatively small variations in particle size.

The simplifying assumptions necessary to reduce processing demands down to a manageable level can prevent the resulting particle pack from accurately portraying the actual packs that are intended to be simulated.

An approach that has been used to make the processing demands more manageable and yet the accuracy and reliability of the simulation to be good involves a reduced dimension approach. An example of this approach is described in I. Lee Davis and Roger G. Carter, "Random Particle Packing by Reduced Dimension Algorithms," J. Appl. Phys., 67(2), 15 Jan. 1990 pp. 1022–1029 (hereinafter "Davis and Carter"). The reduced dimension approach as described there involves simplifying the pack construction problem by employing the principle that an arbitrary straight line drawn through a uniformly random three-dimensional particle pack (regardless of whether the particles are spheres) will, on the average, lie inside particles the same fraction of its length as the packing fraction. As the length of the line goes to infinity, the fraction of its length residing inside the particles of a random pack goes to the packing fraction exactly. The line is referred to in Davis and Carter as a "central string." This approach has proven quite useful in enabling more complicated particle packs to be constructed. It can accommodate a substantially wider range of particle sizes.

Notwithstanding the usefulness of the reduced dimension approach to constructing particle packs, its direct application has been limited to a certain extent in that its accuracy can be compromised by considering only particles intersected by the central string. In real three-dimensional packs, and assuming the particles are spherical, each sphere initially intersecting the central sphere, as it slides down the central string during placement, comes to rest more often on a "nearest-neighbor" sphere than on a lower central string particle. The sphere then would roll away from the central string, thereby spreading the spheres over a greater distance along the central string.

A technique for addressing this limitation, also presented in the Davis and Carter paper noted above, involves relaxing the requirement that spheres must intersect the central. Under this modified approach, particles are permitted to come to rest within a defined range of the central string, after assuming that their path is modified to encounter and avoid previously placed spheres. This is referred to generally as "perturbation," or perturbed central string packing.

This modified reduced dimension approach also has been limited, however, in that, when perturbation approaches are used, processing demands once again increase, in some cases substantially. This can give rise to a fuller and more complicated particle field that once again begins to approach the complexity and processing intensity of a full field.

Accordingly, it would be desirable to provide apparatus and methods for creating a particle pack that simulate the actual particle distribution within a space with a reasonable degree of accuracy.

It would also be desirable to provide apparatus and methods for creating a particle pack that involve reduced processing demands and increased processing efficiency relatively to full field simulation.

Advantages of the invention will be apparent from the description, or may be learned by practice of the invention in accordance therewith. The advantages of the invention may be realized and obtained by means of the instrumentalities and combinations pointed out in the appended claims.

SUMMARY OF THE INVENTION

To achieve the foregoing objects, and in accordance with the purposes of the invention as embodied and broadly described in this document, a machine-implemented method is provided for placing a plurality of particles, each having a characteristic dimension, to create a particle pack, the plurality of particles comprising N categories of the particles, the characteristic dimension of the particles of a given category being different from the characteristic dimensions of the particles of other ones of the categories, the characteristic dimension of the particles increasing as the category N increases. The method comprises: a) defining a central string, a space disposed about the central string, and N concentric subspaces disposed about the central string and within the space, each of the N subspaces corresponding to one of the N particle categories; b) selecting a particle from the plurality of particles; c) placing the selected particle in the corresponding subspace so that the selected particle becomes a placed particle at a particle location unique to that placed particle and is in non-overlapping relation with other placed particles, wherein the selected particle placement, according to one aspect of the invention, includes defining a catch net representative of buoyancy of a portion of the placed particles and positioning the catch net within the space based upon the placement of the portion of the placed particles. The selected particle placement according to another aspect of the invention includes defining a water level representative of a level of a portion of the placed particles that are smaller than the selected particle and represent a surface of the smaller placed particles, and positioning the water level within the space based upon the smaller particle surface. The selected particle is placed in non-overlapping relation with respect to the catch net and the water level; and d) repeating the particle selection (b) and placement (c) until each of the particles of the plurality of particles has become one of the placed particles.

In accordance with preferred but optional implementations of the invention, the following may apply. The particles comprise spheres and the characteristic dimension of each of the particles comprises a radius. The central string comprises a line within the space, preferably the z axis of a rectilinear coordinate system imposed within the space. Each of the subspaces has a characteristic dimension that corresponds to the characteristic dimension of the particles of the corresponding subspace. Each of the subspaces may comprise a cylinder. The subspaces comprise concentric cylinders disposed about the central string, each of the cylinders defining one of the subspaces and having a radius that corresponds to the radius of the particles in the category corresponding to that cylinder. The particle selection may comprise selecting the particles randomly or selecting the selected particle from a distribution of the particles.

In accordance with another aspect of the invention, an apparatus is provided for placing a plurality of particles, each particle having a characteristic dimension, to create a particle pack, the plurality of particles comprising N categories of the particles, the characteristic dimension of the particles of a given category being different from the characteristic dimensions of the particles of other ones of the categories, the characteristic dimension of the particles increasing as the category N increases. The apparatus comprises: a) an input device for inputting particle selection information; b) a storage device operatively coupled to the input device for storing the particle selection information; c) a processor for selecting a particle from the plurality of particles, for placing the selected particle at a particle location unique to the selected particle in the corresponding subspace so that the selected particle becomes a placed particle at a particle location unique to that placed particle and is in non-overlapping relation with other placed particles, and for establishing a catch net representative of buoyancy of a portion of the placed particles and positioning the catch net within the space based upon the placement of the portion of the placed particles, the processor placing the selected particle being placed in non-overlapping relation with respect to the catch net.

In accordance with another aspect of the invention, a machine-readable medium is provided for use in placing a plurality of particles, each particle having a characteristic dimension, to create a particle pack, the plurality of particles comprising N categories of the particles, the characteristic dimension of the particles of a given category being different from the characteristic dimensions of the particles of other ones of the categories, the characteristic dimension of the particles increasing as the category N increase. The machine-readable medium comprises: a) machine executable instructions for defining a central string, a space disposed about the central string, and N concentric subspaces disposed about the central string and within the space, each of the N subspaces corresponding to one of the N particle categories; b) machine executable instructions for selecting a particle from the plurality of particles; c) machine executable instructions for placing the selected particle at a particle location unique to the selected particle in the corresponding subspace so that the selected particle becomes a placed particle at a particle location unique to that placed particle and is in non-overlapping relation with other placed particles, the selected particle placement instructions including instructions for defining a catch net representative of buoyancy of a portion of the placed particles and positioning the catch net within the space based upon the placement of the portion of the placed particles, the selected particle being placed in non-overlapping relation with respect to the catch net; and d) machine executable instructions for repeating the particle selection (b) and placement (c) instructions until each of the particles of the plurality of particles has become one of the placed particles.

In accordance with another aspect of the invention, an apparatus is provided for placing a plurality of particles, each particle having a characteristic dimension, to create a particle pack, the plurality of particles comprising N categories of the particles, the characteristic dimension of the particles of a given category being different from the characteristic dimensions of the particles of other ones of the categories, the characteristic dimension of the particles increasing as the category N increases. The apparatus comprises: a) an input device for inputting particle selection information; b) a storage device operatively coupled to the input device for storing the particle selection information; c) a processor for selecting a particle from the plurality of particles, for placing the selected particle in the corresponding subspace so that the selected particle becomes a placed particle at a particle location unique to that placed particle and is in non-overlapping relation with other placed particles, for establishing a water level representative of a level of a portion of the placed particles that are smaller than the selected particle and represent a surface of the smaller placed particles, and for positioning the water level within the space based upon the smaller particle surface, the selected particle being placed in non-overlapping relation with respect to the water level.

In accordance with still another aspect of the invention, a machine-readable medium is provided for use in placing a plurality of particles, each particle having a characteristic dimension, to create a particle pack, the plurality of particles comprising N categories of the particles, the characteristic dimension of the particles of a given category being different from the characteristic dimensions of the particles of other ones of the categories, the characteristic dimension of the particles increasing as the category N increases. The machine-readable medium comprises: a) machine executable instructions for defining a central string, a space disposed about the central string, and N concentric subspaces disposed about the central string and within the space, each of the N subspaces corresponding to one of the N particle categories; b) machine executable instructions for selecting a particle from the plurality of particles; c) machine executable instructions for placing the selected particle at a particle location unique to the selected particle in the corresponding subspace so that the selected particle becomes a placed particle at a particle location unique to that placed particle and is in non-overlapping relation with other placed particles, the selected particle placement instructions including instructions for defining a water level representative of a level of a portion of the placed particles that are smaller than the selected particle and represent a surface of the smaller placed particles, and positioning the water level within the space based upon the smaller particle surface, the selected particle being placed in non-overlapping relation with respect to the water level; and d) machine executable instructions for repeating the particle selection (b) and placement (c) instructions until each of the particles of the plurality of particles has become one of the placed particles.

BRIEF DESCRIPTION OF THE DRAWINGS

The accompanying drawings, which are incorporated in and constitute a part of the specification, illustrate presently preferred embodiments and methods of the invention and, together with the general description given above and the detailed description of the preferred embodiment and methods given below, serve to explain the principles of the invention.

DETAILED DESCRIPTION OF THE INVENTION

Figure 1:
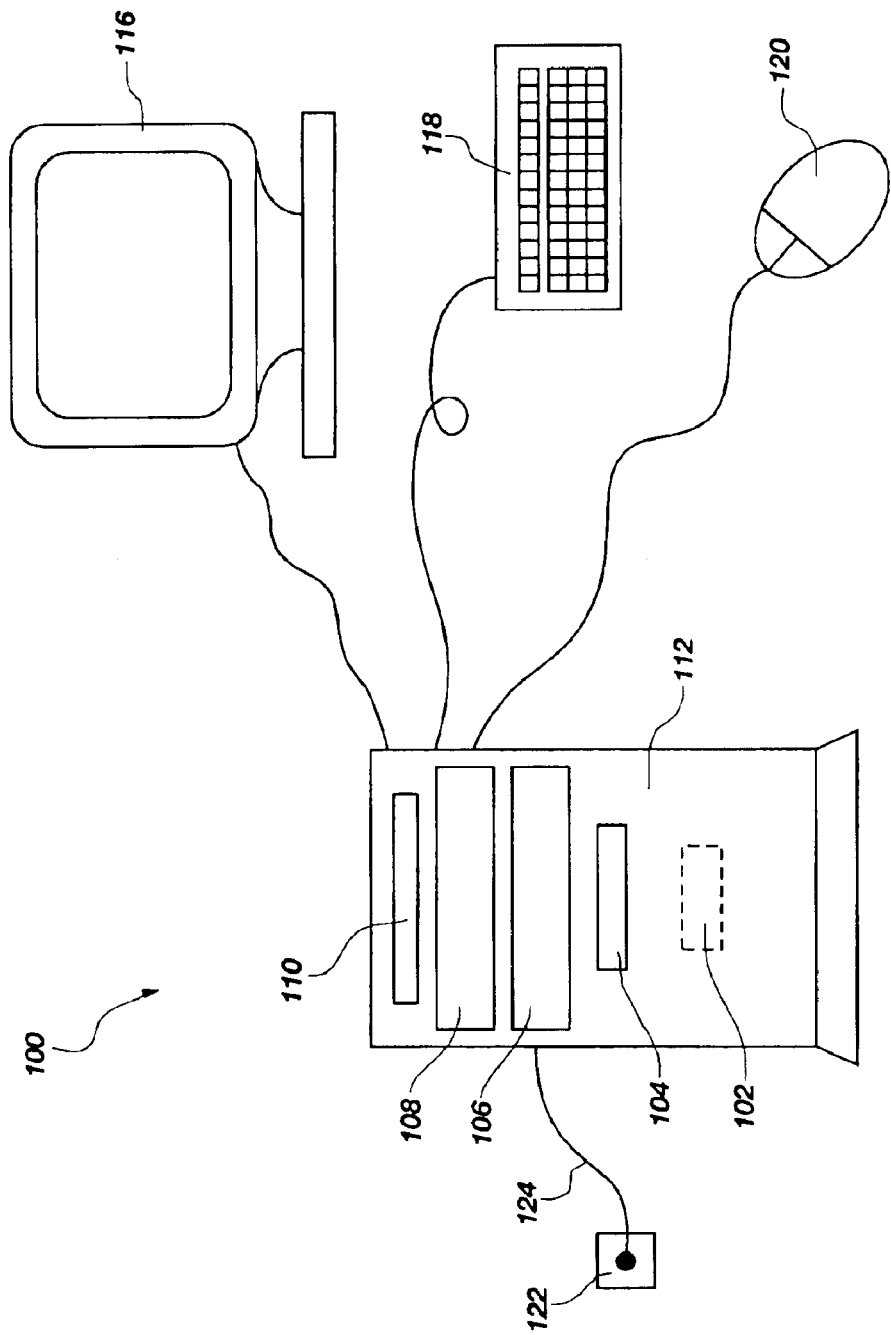
FIG. 1 is a pictorial diagram of a computer system which comprises a presently preffered embodiment of the apparatus according to the invention, and upon which the presently preferred vision of the inventive method may be carried out.

Reference will now be made in detail to the presently preferred embodiments and method of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

In accordance with one aspect of the invention, an apparatus is provided for creating a particle pack. In accordance with another aspect of the invention, a machine-implemented method is provided for placing a plurality of particles to create a particle pack.

A "particle," as the term is used herein, is used according to its common but broad meaning in the field. It includes any type of particle that might be found in a particle rigid body of arbitrary shape containing materials. In the preferred implementation, particles comprise rigid or nearly rigid objects of arbitrary size and shape.

It is useful in analyzing particle packs to be able to segregate the particles into categories. A group of substantially identical particles, or a group of particles that for purposes of analysis may be deemed identical, and which group is in some way distinguishable from other groups of particles is called a "mode." If there is only one type of particle comprising the pack and those particles are identical to each other, or may be assumed to be identical, the pack is said to be "monomodal." If there are two types of particles, the pack is "bimodal," and if multiple types of particles are present, it is "multimodal."

A mode represents a principal size or type of particle. In practice, particles even within a mode often are not exactly identical, but instead have slight variations. In some instances, for example, each mode can be divided into a size distribution about some mean. The distribution may comprise a number of discrete sizes about that mean. The sets of various particles of a given size or character within a particular mode are called "submodes." In the presently preferred implementation, if there is no size distribution attached to a particular mode, the submode arrays simply contain the mode data as their first and only entry. Because both modes and submodes theoretically merely involve segregating particles into categories based upon one or more distinguishing characters, modes and submodes are referred to generally herein as "categories."

Illustrated in FIG. 1 the apparatus according to the invention preferably comprises a computer system 100, such as a commercially available personal computer, small business computer, engineering work station, mainframe, microprocessor, or virtually any other machine with similar processing power, appropriately configured and programmed with computer software or "code" as outlined and described herein for performing the tasks identified herein. The computer system 100 includes a processor 102, storage in the form of RAM 104, a hard drive 106, a compact disk (CD) drive 108, and a drive for diskettes 110, all contained within a cabinet 112. System 100 also includes a monitor 116, a keyboard 118, and a pointing device 120 such as a mouse, track ball or the like. System 100 also may be part of a network, in which case it may include a network connection 122 and network bus 124. The method according to the present invention, in its presently preferred implementations, may be carried out on computer system 100, using the same hardware and software, as described herein with respect to the preferred embodiment of the apparatus according to the invention.

"Machine", as the term is used herein, refers broadly to a computer, processor, microprocessor, a network of such devices, or other apparatus capable of performing processing as described herein. Such machines typically and preferably will comprise a computer, such as computer system 100.

OVERVIEW OF THE PREFERRED EMBODIMENT

The method and apparatus according to the presently preferred yet merely illustrative versions of the invention will be described in this document as involving the implementation and execution of a computer program that can be run on a computer system or machine as described above. The preferred versions of the apparatus and methods according to the invention are referred to collectively in this document as the "preferred implementation."

The architecture of the preferred implementation is outlined below. In its presently preferred form, it is written in double precision C++ or Fortran 90. This is not, however, limiting. The code may, for example, be written in FORTRAN, or other suitable programming languages. An example of such a computer system is shown in FIG. 1. The code in its preferred version builds a single particle pack and outputs user-specified pack microgeometry and statistics. It is modular and can be disassembled into its component subroutines for use elsewhere.

In accordance with the apparatus aspect of the invention, an input device is provided for inputting particle selection information, and a storage device operatively coupled to the input device for storing the particle selection information. The information used by the preferred implementation will be described throughout this document. The input device may comprise any one or any combination of several input means, including a network download, the CD reader, a diskette reader, the keyboard, the tracking device, a tape drive, or any other means used for inputting data into a machine capable of implementing these aspects of the invention. The storage device also may comprise any suitable storage means, and may include RAM, the hard drive, an optical storage device, storage devices on a machine operably coupled to or accessible by computer 100, or other suitable storage devices readable by a computer directly or with translation.

The main program of the preferred implementation comprises seven subroutine calls. The names and functions of these subroutines are as follows:

| SUBROUTINE NAME | SUBROUTINE FUNCTION |
| --- | --- |
| INITERROR | Initializes arrays containing the number of errors, warnings, and notations accumulated during program execution. It also initializes arrays containing information on how these data are to be displayed. |
| INNAME | Looks for and reads an input file named INNAME.INP which contains the names of files containing the input data needed by the preferred implementation to build the user-specified pack and output the requested pack information. If the file INNAME.INP does not exist, default file names are used to find instructions on pack building. Default values are used if user-specified instructions are lacking. If essential instructions are lacking, pack building is aborted and error messages are issued. |
| SETHISTOGRAM | Reads the information for the types, quantities, and sizes of particles to be used in constructing the pack. |
| SETCONTROL | Reads flags and parameters controlling the construction of the pack. Default values are used if files containing these instructions cannot be found. |
| SETOUTPUT | Reads flags and parameters controlling the type of pack data to be output. Default values are again used if files containing these instructions cannot be found. |
| PPACK | Constructs the particle pack according to instructions read by the previous subroutines. Each time it is called to build a new pack, it initializes all variables and arrays so there will be no interfering data left over from a previous call. |
| OUTSTAT | Outputs the user-specified information on pack microgeometry and statistics. |

In summary, the first subroutine (INITERROR) initializes error, warning, and notation arrays and parameters. The next four subroutines (INNAME, SETHISTOGRAM, SETCONTROL, SETOUTPUT) and the seventh subroutine (OUTSTAT) control the reading of building instructions and the output of data. The sixth routine (PPACK) constructs the particle pack. This modularity facilitates incorporation of the code or portions of it into larger calling codes, such as codes using numerical methods or finite element analysis.

Because in the preferred implementation a substantial amount of information may be used to govern particle pack construction, the manner in which the data used by the software code is categorized in the context of the preferred implementation will now be described. These data categories are placed into common blocks and passed from one code section to another as needed. In the presently preferred implementation, all data about the pack along with building instructions are placed into one of the following categories:

| DATA BLOCK | DESCRIPTION |
| --- | --- |
| HISTO | Governs the types and quantities of particles to be used in constructing the pack, i.e., the particle histogram. |
| CONTROL | Contains all parameters and flags controlling how the pack will be built and stored. |
| CURINFO | Contains information on the status of the particle currently being placed, such as its position and which other particles it is currently touching. |
| PLACED | Contains information on all particles placed so far in the pack including the position, size, and type of each particle. |
| SETOUT | Contains the flags and parameters governing what pack statistics are to be generated and how the pack microgeometry and its statistics are to be output. |
| ERRORS | Contains the names errors, warnings, and notations that can occur in program input, execution, and output. It is used to monitor the number of times each error, warning, or notation occurs and records such information in a file and/or to the screen, according to the dictates of the user. |

THE SUBROUTINE INITERROR

In the presently preferred implementations, there are three categories of information, called "advisors," used to monitor the health of the pack, i.e., to monitor whether any of the pack construction rules, such as the prohibitions against particle overlap, and general requirements for particle distribution in the pack (e.g., homogeneity at the macro level of the random or other specified statistical distributions at the microphone mount level) have been violated. They are contained in the program's error arrays and parameters. The three categories of advisors are errors, warnings, and notations.

Error advisors are of two kinds, fatal and nonfatal. A fatal error will stop program execution because there is not enough information available to build the pack. Nonfatal errors will not stop the program execution but will use default values in place of erroneous user-data. Therefore, a pack will be built but may not be the kind of pack the user intended.

Warning advisors are notifications of unusual situations or potential problems. If the warning deals with user input, the user should correct the input problem because the warning sometimes precipitates the use of defaults that may not have been intended.

The third category is notation advisors. There are many data that may be of interest during pack building. Notations report on these items. They are not errors or warnings but simply notifications of items of interest as pack building proceeds or after it has finished.

All advisors in this implementation have arrays that keep track of how many times each has been called: NumErrors(i), NumWarnings(i), and NumNotes(i), for the i-th error, warning, or notation, respectively. The totals for each category of advisor are also accumulated in the parameters NTotErrors, NTotWarnings, NtotNotes.

The display of advisors in this preferred implementation is controlled by arrays containing integers limiting the number of times an advisor is to be displayed to the computer screen and written to a disk file created for that purpose. The integer arrays LimScErrors(i) and LimDiErrors(i) dictate how many times the i-th error is to be written to the screen and the disk file, respectively. Similarly, LimScWarnings(i) and LimDiWarnings(i) are provided for warnings and LimScNotes(i) and LimDiNotes(i) for notations. If any of these array elements is less than or equal to zero, the corresponding advisor is not written. If the user wants all advisors written every time they are encountered, the limit arrays need simply be set to a very large integer (in this implementation not to exceed 2147483646, which is one less than the maximum integer size). The total number of times any advisor has been encountered is monitored in NTotErrors, NTotWarnings, and NTotNotes whether or not it is displayed.

All data on all advisors according to this preferred implementation are kept in and monitored by the subroutine ErrWarnNote(ierr, iwarn, inote, iunitnumber), where ierr is the integer specifying the error, and similarly for iwarn and inote. The integer iunitnumber is the disk file unit number to which advisors are written as requested. It is assigned the number 13 in this implementation.

THE SUBROUTINE INNAME

In the presently preferred implementation, the data required by the code are read from several data files. The INNAME subroutine reads the names of the data files in which the data resides from a file called INNAME.INP. The files whose names are specified in INNAME.INP are as follows:

| FILE | DESCRIPTION | DEFAULT NAME |
| --- | --- | --- |
| Histogram | Contains data on sizes, quantities, and types of particles along with material information and the sizes of the cylinders into which they are to be dropped | HIST.INP |
| Drop File | Contains data on where and how particles are to be dropped onto the pack. | DROPDATA.INP |
| Preplace File | Containing the positions and types of particles to be preplaced in the pack, if any. | PREPLACE.INP |
| Input Control File | Contains the input flags and parameters that control how the pack is to be built. | INFLAG.INP |
| Output Control File | Contains flags and parameters controlling what output data is to be generated and how it is to be displayed. | SETOUT.INP |

In accordance with the preferred implementation, if the file INNAME.INP does not exist, then default names are used for each of the five files containing input data. The default names for this implementation are identified in the third column of the table above.

In the preferred implementation, the histogram file is mandatory but the other files are not. Packs can be built if all other files are missing by using defaults. Of course, the various options and data production capabilities of the presently preferred implementation may not be exercisable without these other files.

THE SUBROUTINE SETHISTOGRAM

The SETHISTOGRAM subroutine according to this preferred implementation reads the particle histogram from the histogram file and sets necessary parameters in the program associated with that file. The particle histogram comprises a set of particle modes and submodes, in this implementation in the form of arrays. If there is no size distribution attached to a particular mode, the submode arrays simply contain the mode data as their first and only entry.

First, subroutine SETHISTOGRAM checks to see if the histogram file exists. If it does not, the program is terminated with a fatal error message. If the file exists, the data is read as follows.

The number on the first line of the histogram file is the "stop build" criterion in the form of an integer called STOPBUILD. If STOPBUILD is positive, then that is the total number of particles to be placed in the pack. If STOPBUILD is less than or equal to zero, then pack building is to be stopped when the center of the highest placed particle reaches a certain altitude or when a prespecified maximum number of particles is placed, whichever comes first. If STOPBUILD is less than or equal to zero, the second line is the real number STOPALTITUDE specifying the altitude at which pack building is to cease.

The particle histogram is processed next in this implementation. Each set of lines contains the data for one mode. The modes do not have to be in any particular order. The first line of the set contains the mode information. If there is a size distribution associated with this mode, a set of lines follows that specifies the submodes. In this implementation there are six numbers on each mode line.

1. The first number is the mean particle size for the mode. It is read in as a particle diameter but is internally converted to particle radius.
2. The second number is the mass quantity for the mode. Because the total mass quantities are normalized later, relative mass quantities are adequate.

3. The third number is the mass density for the mode. The units of particle size and density preferably are consistent. In this implementation this is a requirement. For example, one should not input a mode diameter in microns and its density in grams/cm$^3$.
4. The fourth number is an integer specifying a material number for the mode. Material numbers are a way of specifying some property unique to a mode or set of modes. For example, a material number may specify a particular material composition or it may specify a set of modes that have some other feature in common.
5. The fifth number is the radius of the cylinder into which the particles of this mode will be dropped. The centers of the particles are constrained to stay within this cylinder wall. If there is a distribution associated with this mode, the cylinder radius of the mode is ignored and the cylinder radii for each submode are used.
6. The last number is a logical parameter RDIST specifying whether there is a distribution of submodes associated with this mode. If the parameter is FALSE, there is no distribution and the first submode array elements are filled with information for that mode. If the parameter is TRUE, the program next reads the submode information in the following form.

The submode data for this implementation comprises a set of lines, each one of which includes the following three pieces of information:

1. The submode size. As with the mode sizes, it is read in as a diameter but internally converted to a radius.
2. The fractional mass of the submode. This number is the fraction of the mode's mass contained within this submode. The sum of a mode's fractional masses should add to unity. The program normalizes them if they do not.
3. The submode cylinder radius.

In many parts of the code as presently preferred and implemented, it is convenient to have the submodes ordered in increasing particle size. A global size array is created that contains all submodes in increasing particle size. The global submode arrays comprise an array of submode radii (QSIZE), submode mass (QMASS), submode mass density (DENSITY), submode material number (MODEMAT), and submode cylinder radii (SUBCYLRAD).

The end of a submode is signaled by a set of zeroes everywhere that a nonzero number was expected, and the end of a mode is likewise signaled when a set of zeroes is read.

After reading all mode and submode information, the SETHISTOGRAM subroutine reads the information in the drop file if it exists. If it does not exist, the program drops the particles randomly anywhere within the cylinder corresponding to that mode or submode. If it does exist, then it contains the following data.

The first line has two integers. The first integer is a drop option, either 1, 2, or 3. The second integer is the number of particles that are to be dropped according to that option.

Option 1 means that first group of particles are to be dropped randomly anywhere within their cylinder.

Option 2 means that the particle group is to be dropped within a circle of relative radius $a_r$ where the drop radius is some fraction of the cylinder radius ($0 \leq a_r \leq 1$) of the particle that will be selected. The center of this circular region is at relative radial position $p_r$ where $p_r$ is some fraction of the particle's cylinder radius when it is chosen ($0 \leq p_r \leq 1$). Because dropping particles outside the cylinder wall is forbidden, it should hold that $p_r + a_r \leq 1$. These data are stored in the pack position arrays.

Option 3 means that each particle in that group is to be dropped from a specified position and is of a specified mode. The x position of the drop site is stored in the x position array, the y position in the y position array, and the mode number in the mode number pack array. If an (x, y) position lies outside the cylinder corresponding to that mode, a warning message is issued and the particle is randomly dropped anywhere within the cylinder.

The end of this input file is signaled by a value of zero for the drop option.

Another function of the SETHISTOGRAM subroutine in this implementation is to create an index array that orders the global cylinder radii in ascending order with an integer array called CylSizeOrder so that cylrad(CylSizeOrder(1)) is the smallest cylinder radius, cylrad(CylSizeOrder(2)) is the second smallest, and so forth.

THE SUBROUTINE SETCONTROL

The currently preferred implementation includes a variety of options for pack construction. Some of those options are read in a file that can have any name as specified in Subroutine INNAME but whose default value is INFLAG-.INP. This subroutine SETCONTROL reads those control parameters.

If a data file containing input control parameters exists, then the control parameters are read from it in this implementation. If it does not exist, a default is set for each parameter in this routine. The parameters used in this implementation are described in detail below but in summary include the following:

ROUGHNET=A flag that specifies whether the k-th mode catch net (described below) is ratcheted up after each particle placement so that no two particles are at exactly the same altitude. It is mostly used at the beginning of pack building so the spheres at the bottom of the pack do not lie exactly on the bottom of the cylinder. The default is TRUE.

POOL=A flag that specifies whether the number of particles in the pack are selected by a random number generator, weighted by their frequency of occurrence in an infinite pack, or whether they are selected from a pool whose mode proportions are, to the nearest integer, exactly the proportions of an infinite pack. If the POOL flag is TRUE, then random chance variations in modes that contribute few particles to the pack are avoided. The default is TRUE.

FINDLOW=A flag that orders find the lowest exposed north pole of placed particles within its drop cylinder and to drop immediately in its neighborhood. It is overridden by any instructions that may appear in the drop file. The default is TRUE.

NDROP=A positive integer that specifies the number of times a trial drop of each particle is to be made. The lowest final resting place is selected from among the trial drops. Higher values for NDROP means the pack will be more dense. The default is one.

ISEED=An integer specifying the random number seed. A non-positive integer will trigger to seed the random number generator from the system clock.

TUNNEL=A flag that gives permission to check for cavities underneath larger spheres when a smaller sphere is dropped. The small sphere "tunnels" through the large one and, if there are no overlaps in the southern or underneath side, is dropped again from that underneath position whereupon it searches for a final resting place in that cavity. The tunneling procedure seeks to mimic tamping or shaking a pack to fill in such cavities, thereby making the pack more dense.

THE SUBROUTINE SETOUTPUT

A particle pack is typically created so that the system or method user can obtain specific information about the actual particle pack the simulation is intended to simulate. The information required depends on the application. The subroutine SETOUTPUT in this implementation reads the flags and parameters that instruct other parts of the preferred implementation to create specific pack information. In this implementation, for example, if the instruction file for setting output flags and parameters does not exist, the code outputs a limited amount of information into a file called PACKDATA.OUT. Otherwise, this basic pack information is output to a file name specified in Subroutine INNAME. With no specifications, the following data is sent to the output file:

- an echo of the particle histogram;
- the packing fraction;
- the maximum and minimum positions of particles for each submode as well as overall maxima and minima; and
- the number of particles placed for each submode as well as total particles placed.

If the pack output file exists when using the preferred implementation, it preferably contains the following information. The first line contains a flag specifying whether the particle pack is to be written to a disk file. The default is FALSE. If the flag is TRUE, then the next set of lines specifies how the pack file is to be written. On the first subsequent line, the format of the pack (ASCII or binary) is written. On the second subsequent line, a flag is read that determines whether the material number and radius are written in the pack file in addition to the three coordinates and the mode number. On the third subsequent line, the output geometry (Cartesian or cylindrical coordinates) is written. The name of the file to which the pack is to be written is on the fourth line.

The next line contains a flag specifying whether radial distribution functions $g_{ij}(r)$ are to be generated. If it is TRUE, then the functions that are to be generated are specified in a list of integer pairs i and j on the subsequent lines, where the i and j represent modes or submodes. Each line also contains a $\Delta r$ which is the increment in terms of the j-th particle radius in which the number of particle centers are to be counted (default=0.1 radius) and $r_{max}$ which is the extent to which the radial distribution function extends in terms of j-th particle radius. Hence each radial distribution function requested is on a line with the format i j $\Delta r$ $r_{max}$.

The list ends when zeroes are read. Each radial distribution function is written to a file with the name g[i]_[j].dat where each set of square brackets indicates an actual specified integer to be used in the file name, e.g., g3_14.dat for the radial distribution function of Mode 14 spheres about Mode 3 spheres. The default for the radial distribution flag in this implementation is FALSE.

The next line in this implementation contains a flag specifying whether coordination numbers are to be generated. If it is TRUE, then the coordination numbers that are to be generated are read as a list of integer pairs i and j on subsequent lines. The list ends when zeroes are read. The coordination numbers preferably are all written to one disk file COORNUM.DAT. The default for the coordination number flag in this implementation is FALSE.

Radial distribution functions and coordination numbers and their calculation procedures are defined in the discussion of subroutine OUTSTAT, below.

In accordance with the apparatus aspect of the invention, the apparatus comprises means for defining a space, a plurality of subspaces within the space, and a central string within the space and within the subspace. In accordance with the method aspect of the invention, the method comprises defining a space, defining a plurality of subspaces within the space, and defining a central string within the space and within the subspaces.

The subspaces preferably comprise N concentric cylinders disposed about the central string and within the space. Each of the N cylinders corresponds to one of the N particle modes and has a cylinder radius corresponding to the particle radius of the particles of the corresponding particle mode. The means as implemented in the preferred embodiment comprises the processor.

Figure 2:
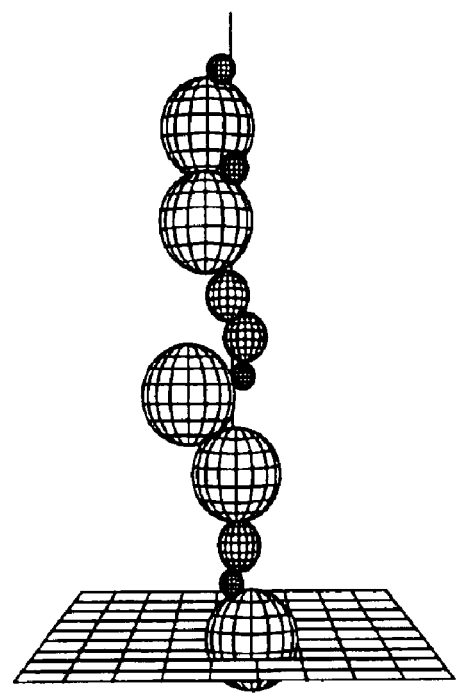
FIG. 2 is an illustrative example of a particle pack construction according to the preferred implementation, wherein spherical particles are placed along the central string.
Figure 3:
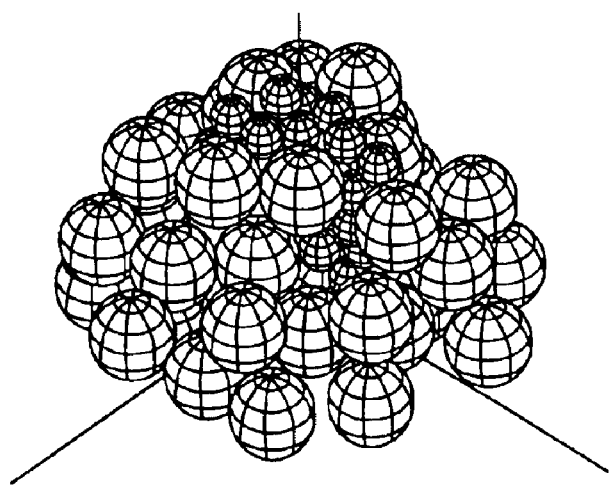
FIG. 3 shows another illustrative example of a particle pack construction accordind to the preferred implementation, wherein spherical particles are placed along the central string, but wherein the particles extend more several particle diameters out from the central string.
Figure 4:
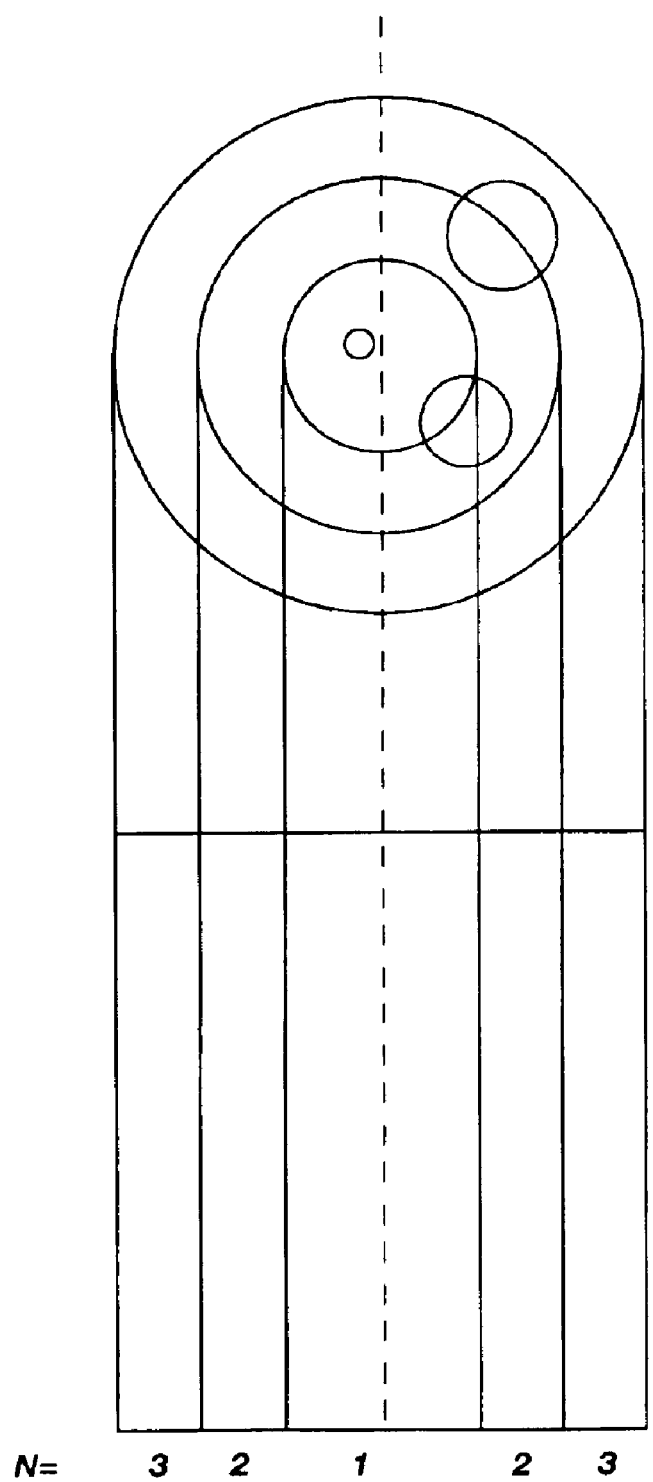
FIG. 4 shows a cylindrical space with cylindrical subspaces therein according to the preferred embodiment and the preferred method of the invention.
Figure 5:
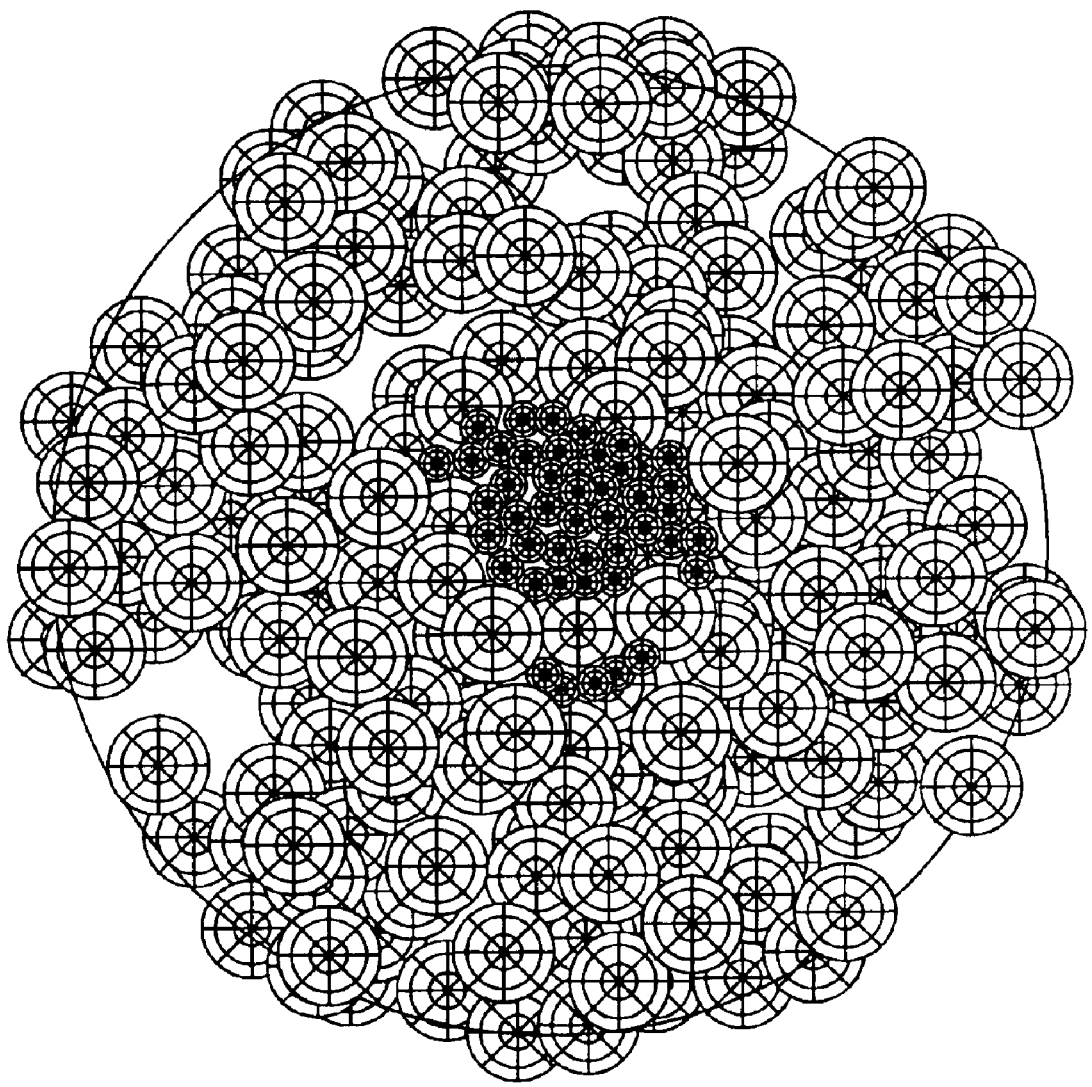
FIG. 5 shows an illustrative particle pack constructed using the preferred implementation.

The space and subspaces are constructions that define the regions or volumes into which the respective particles are to be placed. The space may comprise any contained geometric region, but preferably comprises a cylindrical construction. The subspaces also may comprise any contained geometric region, but preferably have a shape and configuration that corresponds to the overall space. In the preferred versions of the apparatus and method, the space comprises a cylindrical volume, and the subspaces comprise a plurality of concentric cylinders, disposed about a longitudinal or z axis, wherein sequential ones of the cylinders have a radius that is larger than the prior cylinders. An illustrative example of such a concentric cylinder configuration is shown in FIG. 2. The number of cylinders in the preferred implementation is equal to the number of particle categories, e.g., submodes, that will be present in the particle pack. The radius of each cylinder is selected to correspond to the radii of the particles. The radius of the first cylinder corresponds to or is a function of the particle radius of the smallest mode, the radius of the second cylinder is equal to the particle radius of the second smallest mode, and so on. The cylinder radius for a particular particle category preferably corresponds to or is a function of the radius or a representative radius of the corresponding particle for that mode or submode. The cylinder radius may be any positive number multiple of the particle radius. Preferably, but optionally, the cylinder radius is about 3 to 10 times the particle radius, and more preferably, about 5 to 10 times the particle radius.

The SUBROUTINE PPACK

Further in accordance with the method aspect of the invention, the method includes selecting a particle from the plurality of particles, and placing the selected particle in the corresponding subspace so that the selected particle becomes a placed particle at a particle location unique to that placed particle and is in non-overlapping relation with other placed particles.

In accordance with the preferred implementation, particles are selected randomly from the distribution of particles using a Monte Carlo method, although this is not necessarily limiting. In terms of the apparatus, this comprises a random number generator in computer system 100.

Regarding terminology, a "selected particle," also referred to herein as a "current particle," is a particle that has been selected for placement, but has not yet been placed (become a "placed particle") in a particle location in the particle pack. A "placed particle" is a particle that has been placed or fixed by assigning it a unique particle location in the particle pack.

In the preferred implementation, the software code subroutine selects particles and constructs the particle pack according to instructions read by the previous subroutines. Each time it is called to build a new pack, it initializes all variables and arrays so there will be no interfering data left over from a previous call. Code lines of PPACK and a brief explanation of each will now be provided.

CALL PREPAREPACK

Subroutine PREPAREPACK performs three functions in this implementation. First, it preplaces particles, if any, that have a position assigned by the user, such as would be desirable if semirandom packs were to be built. Secondly, it arranges histogram data such that particles can be chosen by the random number generator with probabilities appropriate for their abundance in the reduced dimension pack. Third, it initializes and sets parameters that will be used by the rest of the subroutines in PPACK.

DO icarus=1, stopbuild

This DO loop continues to cycle until either the user-specified number of particles has been placed in the pack or until a pack height has been reached.

CALL CHOOSE

Subroutine CHOOSE chooses the type, category, mode or submode of the next particle to be dropped. It drops the "current particle" according to user-specified instructions.

DO idrop=1, ndrop

The user may specify more than one drop at different drop sites for each particle so that the lowest final site can be selected. Multiple drops are equivalent to tamping the pack so the particles settle into lower sites resulting in a denser pack.

CALL DROPSITE

Subroutine DROPSITE selects an (X, Y) position from which the particle will be dropped. The site can be chosen randomly, or the user may ask the code to use a criterion to find potential sites where the particle is likely to settle to an especially low final resting place.

CALL PLACE

Subroutine PLACE finds the final resting place or "placed particle location" for the current particle, which is the site at which the current particle will ultimately be placed. The subroutine PLACE in this implementation contains all the instructions on how a particle drops, rolls, and encounters other objects in the pack as it moves toward its final resting place. It is where the machine spends the great majority of its processing time during pack construction.

END DO

CALL UPDATE

Subroutine UPDATE updates all the particle pack arrays and parameters with the position and additional data associated with the newly placed particle.

END DO

RETURN

END

In accordance with the preferred implementation, a particle pack is constructed by "dropping" the selected particles one at a time into the set of concentric cylinders. The dropping presumes a vertical orientation, which is not necessarily required. But regardless of the reference frame, the current particle is moved in the space until it encounters another object, as described in principle herein. Each particle mode is dropped somewhere within the cylinder radius of its corresponding cylinder. The radius of the cylinders in this preferred implementation is specified by the user, but preferably the small particles are dropped into a small-radius cylinder and the larger particles into a larger-radius cylinder or subspace. The large particles can therefore overlap the inner small-radius cylinders but the small particles do not have to fill the volume in the larger cylinders. The reduced dimension approach as described in Davis and Carter is used in this preferred implementation.

The reduced dimensional approach can make pack building tractable from a processing demand perspective when the particles comprising the pack have broad size ranges. Particle centers in this implementation cannot pass outside the radius of the cylinder wall to which they belong but can pass through any smaller cylinder walls. Because only the innermost cylinder can have all modes or submodes intersecting it, only there does the reduced dimension pack literally approximate the corresponding real three-dimensional pack. The remainder of the pack can however be simulated using this approach, for example, by assuming that the remainder of the space is statistically identically configured.

In the presently preferred implementation, the selection of particles to be placed and the placement of the particles in the particle pack are undertaken by the processor within the machine under the execution of the PPACK subroutine. In this implementation, there are four subroutines called by PPACK (PREPAREPACK, CHOOSE, PLACE, and UPDATE). Each of these subroutines and the functions they perform will now be described.

THE SUBROUTINE PREPAREPACK

As noted above, the PREPAREPACK subroutine has three functions: preplacing particles, setting cumulative arrays so the random number generator can readily choose the mode of the next particle to be placed, and initializing various parameters in preparation for building the pack. Each of these functions will now be described in turn.

Preplacing Particles

The first function of PREPAREPACK is to preplace any particles for which the user has specified a position. This option permits semirandom or fully ordered packs to be constructed. A filename is read in Subroutine INNAME that contains the global (X, Y, Z) position and the mode or submode number of each particle to be preplaced. If the filename is not read, the default filename for preplaced particles is PREPLACE.INP. If a filename of preplaced particles does not exist, the program assumes no particles are to be preplaced and this option is not exercised. The preplace file contains five numbers for each particle to be placed. In order, they are the X position, the Y position, the Z position, and the mode number, and the submode number. These are read into the surface arrays.

Setting Arrays for Choosing Particles

The second function of PREPAREPACK according to the preferred implementation is to make an array so that the random number generator can randomly choose, with the appropriate probability, the submode of the next particle to be placed in or on the pack. The relative fraction of particle numbers for each submode therefore should be calculated. The number of particles in each submode to be placed will depend on the submode mass, its mass density, its particle radius, and its cylinder radius, e.g., in the following manner.

In this implementation there are two options in setting up the weighting factors that govern how the random number generator will choose the next particle to be placed. The first option is to use the same weighting factors each time a particle is chosen for placement. This is referred to herein as the "unchanged-weighting option." The second option, referred to herein as a "pool option," creates a pool that has a set of bins with the appropriate number of particles placed into it. Each time a particle is drawn from one of the bins, the weighting factor of drawing from each bin is altered slightly. Creating a pool of particles from which to draw forces the right proportion (to within nearest integers) of particles from each submode to be placed. In the limit of an infinite number of particles in the pack, these two methods are identical. The pool option more closely resembles a very large pack. The unchanged-weighting option will be described first.

Unchanged-Weighting Pool Option

The total volume of k-th submode particles to be placed is $$\frac{m_k}{\rho_k \frac{4}{3}\pi a_k^3} \quad (1)$$

where $m_k$ is the submode mass, $\rho_k$ is the submode mass density, and $\alpha_k$ is the particle radius for that submode.

The relative number of submode k particles in this reduced dimension pack is also proportional to the area of the confining cylinder for that submode: $\pi R_k^2$ where $R_k$ is the radius of the cylinder. Therefore, the fraction $f_k$ of k-th submode spheres to be placed in a reduced dimension pack is proportional to $$\phi_k \equiv \frac{m_k R_k^2}{\rho_k a_k^3}. \quad (2)$$

To obtain the actual fraction $f_k$, the above expression can be normalized:

$$F = \sum_{k=1}^{N} \phi_k \quad (3)$$

where N is the total number of particle submodes. Then $$f_k = \phi_k / F. \quad (4)$$

These are the unchanged-weighting factors that determine which particle submode shall be chosen for the next placement.

These weighting factors are placed into a cumulative array so the random number generator can immediately choose the submode. In other words, the cumulative array is the sum of all weighting factors prior to it:

$$C_1 = f_1 \quad (5)$$

$$C_i = \sum_{k=1}^{i} f_i, 1 < i < N$$

$$C_N = 1.$$

When a uniform random number r is generated on [0, 1], a bisection search is made of the array $\{C_1, C_2, \ldots C_N\}$ to find which pair of numbers the random number lies between. The k-th submode is chosen if $C_{k-1} < r \leq C_k$. $C_0$ is defined to be zero.

Pool Option

The pool option is similar. As discussed before, the user can specify the number of particles to be placed in the pack or can specify a pack height in which case the program continues to add particles until the height is achieved (or until the array sizes are exhausted). The pool option in this implementation can only be used if the user has specified the total number of particles to be placed in the pack, say n. The number of submode k particles $n_k$ to be placed is $$n_k = \text{NINT}[nf_k] \quad (6)$$

where NINT indicates the integer nearest to its argument. Because of nearest integer roundoff, it is possible that the $n_k$ do not sum exactly to n. Then the $n_k$ quantities should be adjusted to compensate where the roundoff errors were the largest.

It is possible, especially for packs with very broad particle size distributions, that some $nf_k < \frac{1}{2}$ so that submode would not be represented at all in the pack. The preferred implementation issues a warning when that happens, or even when a particular $n_k$ is very small, so that the user is aware that the pack is too small to be able to sample enough different configurations to mimic a true three-dimensional particle pack. Changing cylinder sizes on some submodes can solve this situation, should it arise.

Initializing Various Parameters

The packing routine can be called many times, as when the user wishes to search for an optimum pack subject to some set of constraints. Some of the parameters and arrays from previous calls must not be carried into successive calls or they can taint the results. This portion of Subroutine PREPAREPACK initializes all necessary parameters, flags, and arrays for use in a new pack simulation.

THE SUBROUTINE CHOOSE

The CHOOSE subroutine uses the random number generator to choose the submode of the next particle to be added to the pack. The random number generator in this implementation generates a uniform distribution on [0, 1]. The cumulative array from the previous routine PREPAREPACK is a set of numbers such that $$C_0 = 0 < C_1 < C_2 < \ldots C_{N-1} < C_N = 1. \quad (7)$$

Because this cumulative array can be large, and because there is no restriction on the relative distances between successive array elements, in this implementation, a search by bisection is a preferred method to find two numbers between which a given random number lies.

When a random number r is chosen in [0, 1] we want to find the two array elements that bracket it such that $$C_{k-1} < r \leq C_k, 1 \leq k \leq N. \quad (8)$$

(In the unlikely event that r=0, it will be assumed to belong to the first bin, i.e., where k=1.) In preferred bisection methods, a check is made to determine on which side of $C_{N/2}$ the random number lies. Then attention is concentrated on that side and it is bisected again, continually narrowing the range of $\{Ck\}$ in which r lies until Eq. 8 is satisfied.

As noted above, the particle just chosen is referred to herein as the "current particle" or the "selected particle" in the discussion below.

THE SUBROUTINE DROPSITE

The DROPSITE subroutine chooses a drop site from which the current particle can be dropped. Actually, if the user so specifies, it chooses several drop sites and then keeps the site at which the particle came to the lowest possible final resting place, referred to herein as a "placed particle location." In a sense, this is the same as tamping the pack so that it settles into a denser configuration. The user specifies how many trial drops a particle is to undergo. The default in this implementation is one.

There are several options available to the user in this implementation when deciding where a new selected particle is to be dropped onto the pack.

1. Drop it randomly anywhere within its cylinder;
2. Drop it randomly anywhere within a user-specified circle that is contained within the cylinder;

3. Drop it from a user-specified (X, Y) position; and
4. Select the lowest exposed north pole among the placed pack spheres and drop it randomly within a short distance of that pack sphere's (X, Y) position. If dropping multiple times, it is preferable to select the several lowest exposed north poles and drop within a short distance of each of them.

Dropping Randomly Within the Cylinder

When dropping a sphere anywhere within a given cylinder, two random numbers are generated, $u_\phi$ and $u_p$. The azimuthal angle (in radians) of the drop position $\phi_c$ relative to the central string is chosen by $$\phi_c = 2\pi u_\phi. \quad (9)$$

The radial position is not chosen uniformly because there is more area for large radial positions in a circle than for small radial position. Because the area grows as the square of the radial size, all areas will be equally accessible if we take the square root of the random number generator and multiply it by the cylinder wall radius for the current sphere $W_c$:

$$\rho_c = W_c \sqrt{u_p}. \quad (10)$$

The (X, Y) drop site is found as follows:

$$X_c = \rho_c \cos \phi_c \quad (11a)$$

$$Y_c = \rho_c \sin \phi_c. \quad (11b)$$

Dropping Randomly Within a User-Specified Circle

Suppose the user specifies that the particles are to be dropped randomly within a circle of radius R centered at $(X_0, Y_0)$. In the preferred implementation it is required that the circle be contained within the cylinder of the current sphere, i.e., $$\sqrt{X_0^2 + Y_0^2} R \leq W_c. \quad (12)$$

Otherwise, the circle is an illegal specification because a particle cannot be dropped outside its cylinder wall. In that case, the preferred implementation will default to dropping randomly anywhere within the cylinder wall at $W_c$. A value of zero for R is permitted, meaning the particles are dropped from the position $(X_0, Y_0)$. If this condition is satisfied, then the drop site can be selected as follows. Two random numbers are generated, $u_\phi$ and $u_p$. Then $$\phi_c = 2\pi u_\phi \quad (13)$$

$$\rho_c = R\sqrt{u_p} \quad (14)$$

$$X_c = X_0 + \rho_c \cos \phi_c \quad (15a)$$

and $$Y_c = Y_0 + \rho_c \sin \phi_c. \quad (15b)$$

Dropping From a User-Specified XY Position

The condition of dropping a selected particle from a user-specified X-Y position is a subset of the previous discussion for the special case of R=0. The positions are stored in the pack surface arrays for that particle until it is placed, at which time the drop XY position is replaced by the XY position of the final resting location, or the placed particle location, for that particle.

Dropping Above Lowest Sites

In the preferred implementation, a running list is kept of all placed pack spheres whose north poles have not yet been covered by other pack spheres. These north poles are ordered according to their altitude (north pole altitude, not sphere center altitude). It is generally desirable for the current or selected sphere to find a final resting place with the lowest altitude. The lowest exposed north pole is a more likely candidate for a low final placed particle location. Therefore, if the current sphere is to be dropped m times ($m \geq 1$), then we choose the lowest m exposed north poles and drop randomly within a circle of radius $MIN(\alpha_c, \alpha_i)$ of that north pole's XY position, as long as it is within the current sphere's corresponding cylinder wall. The quantity $\alpha_c$ is the radius of the current sphere and $\alpha_i$ is the radius of the placed sphere above whose exposed north pole the current sphere is being dropped. Dropping randomly within this circle is done in the same manner as is described above. North poles outside $W_c$ are ineligible for dropping in this implementation. If there are less than m exposed north poles, the other sites are chosen randomly within the cylinder.

THE SUBROUTINE PLACE

The subroutine PLACE in this implementation takes the current particle from its initial drop site to the final resting place or placed particle location associated with that drop site. The dropping and rolling preferably is done without any dynamics. The particles in this implementation do not bounce, nor do they gain speed or shoot off the edge of another particle with a parabolic trajectory. It is as if the particles are being dropped in a highly viscous fluid so that all inertia is absent and the particle creeps to its final resting place.

There are four subroutines in the presently preferred implementation of the PLACE subroutine. They are referred to herein as FOBJ1, FOBJ2, FOBJ3 and STABLE. FOBJ1 finds the first object the descending current sphere encounters. FOJB2 finds the second. FOJB3 finds the third. STABLE determines which contacted objects the current sphere will stay in contact with and which it will roll away from. The term "object" is used instead of "sphere" because one of the objects of contact may be the cylinder base or wall.

A number of terms will now be defined for purposes of this discussion before describing the operation of the PLACE subroutine. The "roll corridor" is the path of descent of a sphere as it descends along its contacts with one or more spheres and/or the cylinder wall. A good share of the effort of subroutine PLACE is to find the objects that overlap the roll corridor. An "object" according to this implementation can be one of four things that the current sphere can encounter as it descends: (1) other pack spheres (placed particles), (2) the cylinder base or wall, (3) a "water level," or (4) a "catch net." The latter two are described more fully below. "Contact stability" refers to whether the current sphere is in compressive contact with an object or in tensile contact. If it is in compressive contact with another sphere or the cylinder wall, they are pushing against each other due to the weight of the current sphere when gravity is acting along the -z axis. The current sphere at this position stays in contact with an object it compressively touches. Usually if it touches three or more objects compressively, it is stable and is placed at that position. If there is a tensile contact, the object and current sphere are pulling away from each other. Therefore, the current sphere will roll away from the object unless it already has three or more compressive contacts. The first pack sphere touched by the current sphere is denoted as Sphere 1, the second as Sphere 2, and so forth. If a set or plurality of spheres is touched simultaneously, the numerical order can be arbitrarily selected.

Subroutine FOBJ1 searches for the first object of contact. If the current sphere simultaneously contacts more than one object, it checks them for stability through subroutine STABLE. Subroutine FOBJ2 searches for the second object of contact. If the current sphere simultaneously contacts two or more objects, it checks them for stability. Likewise, subroutine FOJB3 searches for the third object of contact. Again, if the current sphere simultaneously contacts three or more objects, it checks them for stability. The current sphere is placed if it is stably touching three or more objects or has hit the catch net or a water level.

We will now give an overview of each subroutine and how they interact, followed by a detailed discussion of each one.

Overview of Subroutine STABLE

Subroutine STABLE determines whether the current sphere is in compressive or tensile contact with all objects it is currently touching. It marks those objects in tensile contact so that the current sphere will roll away from them as it continues to descend.

Overview of Subroutine FOBJ1

The first subroutine for determining object contact is called FOBJ1 for "Find Object 1," object 1 being the first object the descending current sphere encounters. There are four possible outcomes of FOBJ1:

1. The current sphere encounters the catch net or a water level before encountering any other sphere. If it does, then it is placed at the position where such contact occurs.
2. The current sphere encounters a placed sphere of the pack. If it does, the index number of that sphere (hereafter denoted as Sphere 1) is recorded and FOBJ2 is called.
3. The current sphere simultaneously hits two placed spheres of the pack. If it compressively touches both of them, it will roll along the roll corridor defined by them and FOBJ3 is called to determine whether a third object is hit before it loses contact with one or both of the touched placed spheres.
4. The current sphere simultaneously hits three or more placed spheres of the pack. STABLE checks to see if any three of them provide a stable placement. If they do, the current sphere is placed there. If they do not, STABLE marks the objects from which the current sphere will roll away.

Overview of Subroutine FOBJ2

FOBJ2 searches for the second object to be encountered by the current sphere as it descends along the path of steepest descent on Sphere 1. There are four possible outcomes of FOJB2:

1. The current sphere hits the catch net or a water level before encountering any other object. If it does, it is placed there.
2. The current sphere loses contact with Sphere 1 by reaching its equator before encountering any other object. If it does, it is free falling again and FOBJ1 is called, and re-initialized.
3. The current sphere hits a second object, either another placed sphere or its cylinder wall. STABLE is then called to see if it is in compressive contact with both objects. If it is, FOBJ3 is called. If it loses contact with one object, FOBJ2 is recalled and re-initialized. If it loses contact with both objects, it is in free fall again and FOBJ1 is recalled and re-initialized.
4. The current sphere hits two or more additional objects simultaneously. STABLE is called to check for compressive contacts. If there are three or more compressive contacts, the particle is placed where it is. If there are two, FOBJ3 is recalled; if there is one, FOBJ2 is recalled; and if there are none, the current sphere is in free fall and FOBJ1 is recalled.

Overview of Subroutine FOBJ3

FOBJ3 searches for the third object the current sphere encounters as it descends along the roll corridor formed by the first two objects. There are four possible outcomes of FOBJ3:

1. The current sphere hits the catch net or a water level before encountering any other object. If it does, it is placed there.
2. The current sphere loses contact with one of its two contacts before encountering any other object. If it does, FOBJ2 is recalled.
3. The current sphere loses contact with both objects simultaneously before encountering any other object. If it does, it is in free fall and FOBJ1 is recalled.
4. The current sphere encounters one or more additional objects. If it does, STABLE is called to check whether three or more are in compressive contact. If they are, the current sphere is placed there. If not, contacts are lost with those objects in tensil contact. If two objects remain in tensile contact, FOBJ3 is recalled; if one object, then FOBJ2 is recalled; and if all contact is lost, the current sphere is in free fall and FOBJ1 is recalled again.

Detail of Subroutine STABLE

The structure and manner of operation of the STABLE subroutine according to the preferred implementation will now be addressed in greater detail. Particularly, the STABLE routine may consider the current sphere with weight W acting in the -z direction, if it is touching one or more objects, if it is compressively touching them, or if it would roll away from the one or more objects.

Index numbers of placed pack spheres being touched are passed to subroutine STABLE in an array called INDEX-TOUCH. A separate parameter called TOUCHWALL states whether the cylinder wall of the current sphere's submode is being touched. The manner in which the preferred implementation determines the compressive touching criteria when the current sphere touches (a) one sphere, (b) two spheres, (c) three spheres, (d) one sphere and the wall, or (e) two spheres and the wall will now be addressed. There is generally no need to consider compressive touching for more than three objects because the case for more than three objects can be broken into sets of three. At least three objects should be checked, however, because that is the minimum number needed for stable placement in the presently preferred implementation.

Compressive Touching of One Sphere

Determining compressive touching on one and only one pack sphere can be done as follows. If the current sphere is touching its northern hemisphere, it is compressive. Because current spheres are dropped from above, they cannot initially touch southern hemispheres and FOBJ1 rejects a sphere as a touching object if the current sphere only touches its equator.

Compressive Touching of Two Spheres

Consider a current sphere that has descended along a longitudinal line of Sphere 1 until it reaches Sphere 2. When it touches Sphere 2, there are only two possibilities: it will either roll along a roll corridor formed by compressively touching both Spheres 1 and 2 or it will over-roll Sphere 2 and lose contact with Sphere 1. To check for compressive contact with both Spheres 1 and 2, the preferred implementation checks whether the current sphere would contact Sphere 1 if it were to roll down the longitudinal line of Sphere 2 where the current sphere had just contacted Sphere 2. If the current sphere would contact Sphere 1, then it must be in compressive contact with Sphere 1. It is certainly in compressive contact with Sphere 2 because of the contact therewith. Therefore, it is in compressive contact with both spheres. If, on the other hand, the current sphere would roll away from Sphere 1 while rolling down the longitudinal line of Sphere 2, then it will leave Sphere 1 and is only in compressive contact with Sphere 2.

Consider the positions of the three spheres: $(X_1, Y_1, Z_1)$ for Sphere 1, $(X_2, Y_2, Z_2)$ for Sphere 2, and $(X_c, Y_c, Z_c)$ for the current sphere. The radii of these three spheres are $a_1$, $a_2$, and $a_c$, respectively. The Sphere 2 longitudinal line at which the current sphere is touching Sphere 2 is at azimuth $$\phi_{c2} = \tan^{-1}[(Y_c - Y_2)/(X_c - X_2)] \tag{16}$$

and it touches at latitude $$\theta_{c2} = \cos^{-1}[(Z_c - Z_2)/(a_c - a_2)]. \tag{17}$$

If $\theta_{c2} \geq \pi/2$, then the current sphere has rolled into the underside or southern hemisphere of Sphere 2. In this case, it will be in compressive contact with the two spheres. If $\theta_{c2} < \pi/2$, then we must see if it contacts Sphere 1 if it were to roll down the longitudinal line at $\phi_{c2}$.

Let the distance between the current sphere and Sphere 1 be denoted $D_{c1}$ which is a function of $\theta_{c2}$. Its square is given by $$D_{c1}^2 = (X_c - X_1)^2 + (Y_c - Y_1)^2$$
$$+ (Z_c - Z_1)^2 = [(a_c + a_2)\sin\theta_{c2}\cos\phi_{c2}$$
$$+ X_2 - X_1]^2 + [(a_c + a_2)\sin\theta_{c2}\sin\phi_{c2}$$
$$+ Y_2 - Y_1]^2 + [(a_c + a_2)\cos\theta_{c2}$$
$$+ Z_2 - Z_1]^2. \tag{18}$$

If $D_{c1}$ or its square increase as $\theta_{c2}$ increases (ie., as the current sphere rolls down Sphere 2's longitudinal line), then it has lost contact with Sphere 1. That is, if its derivative with respect to $\theta_{c2}$ is greater than or equal to zero, it is not in compressive contact with Sphere 1. If the derivative is negative, it is in compressive contact with both spheres. The expression below is the derivative to within a positive constant of $2(a_c + a_2)$, so if it is negative, the current sphere compressively touches both Spheres 1 and 2:

$$[(a_c + a_2)\sin\theta_{c2}\cos\phi_{c2}$$
$$+ X_2 - X_1]\cos\theta_{c2}\cos\phi_{c2}$$
$$+ [(a_c + a_2)\sin\theta_{c2}\sin\phi_{c2}$$
$$+ Y_2 - Y_1]\cos\theta_{c2}\sin\phi_{c2}$$
$$- [(a_c + a_2)\cos\theta_{c2} + Z_2$$
$$- Z_1]\sin\theta_{c2}. \tag{19}$$

These two-sphere calculations are done in this implementation by Subroutine ST2S.

Compressive Touching of Three Spheres

In the case of compressive touching of three spheres, the current sphere at position $(X_c, Y_c, Z_c)$ and with radius ac is in contact with three pack spheres at positions $(X_1, Y_1, Z_1)$, $(X_2, Y_2, Z_2)$, and $(X_3, Y_3, Z_3)$ and with radii $a_1$, $a_2$, and $a_3$. Let the current sphere have weight W due to gravity or similar force. Assume it is attached to the three spheres at the point of contact with them. The preferred implementation solves a force equation to determine whether the attachments are compressive or tensile. If an attachment is tensile, the current sphere will roll away from it.

Let the unit vectors pointing from the current sphere toward Sphere i where i is 1, 2, or 3, be denoted by $e_i$. Let the magnitude of the force applied on the current sphere by Sphere i be denoted by $f_i$. If $f_i$ is positive, the attachment is tensile; if negative, it is compressive. The three equations needed to solve for the three $f_i$ are given by the vector equation $$f_1 e_1 + f_2 e_2 + f_3 e_3 = (0, 0, -W). \tag{20}$$

Because in the implementation we are only interested in whether the fs are compressive ($f_i < 0$) or tensile ($f_i > 0$) and are not interested in their magnitudes, the preferred implementation simply sets W to unity and obtains for the f solutions $$f_1 = (e_{3x}e_{2y} - e_{2x}e_{3y})/\det E$$
$$f_2 = (e_{1x}e_{3y} - e_{3x}e_{1y})/\det E$$
$$f_3 = (e_{2x}e_{1y} - e_{1x}e_{2y})/\det E \tag{21}$$

where det E is the determinant of the 3×3 matrix whose columns are the unit vectors $e_1$, $e_2$, and $e_3$:

$$\det E = e_{1x}(e_{2y}e_{3x} - e_{3y}e_{2z}) + e_{2x}(e_{3y}e_{1z} - e_{1y}e_{3z}) + e_{3x}(e_{1y}e_{2z} - e_{2y}e_{1z}). \tag{22}$$

If the determinant is zero, the set of equations has no solution because the three placed pack spheres and the current sphere all lie in the same plane. In the unlikely event that this should happen in practice, the preferred implementation first sees if another set of three spheres gives stability if the current sphere is touching more than three placed pack spheres. If there is no stable triplet, then it enacts a subroutine to perturb the current sphere's position slightly in a downward direction such that it will not overlap any of the three spheres. If the perturbation causes contact to be lost with one or two of the touching spheres, it can proceed with FOJB2 or FOJB3. If no contact is lost, then at least the four spheres are no longer coplanar and it can redo the processing without a zero determinant.

These three-sphere calculations are done in the preferred implementation by Subroutine ST3S.

Compressive Touching of One Sphere and the Wall

In the case where there is compressive touching of one sphere and the wall, the wall cannot be the first object contacted because in this implementation, the current sphere drops parallel to it when free falling. Therefore, the only way the current sphere can be in contact with both its cylinder wall and one placed pack sphere is if it hits Sphere 1 and subsequently rolls into the wall. The current sphere is always in compressive contact when rolling on one sphere. Furthermore, because the current sphere must be in contact with Sphere 1's northern hemisphere when it contacts the wall, it must be in compressive contact with the wall because it just rolled into it. Therefore, any time the current sphere is in contact with one sphere and the wall, it is always in compressive contact with both and will descend along a roll corridor defined by both. In the unlikely event that the current sphere hits the cylinder wall and nothing else at the same time it reaches the equator of Sphere 1, it free falls from that point and FOBJ1 is recalled.

Compressive Touching of Two Spheres and the Wall

The case of compressive touching of two spheres and the wall is a simple offshoot of the three-sphere case. The cylinder wall will replace one of the spheres as a contact.

However, in the absence of friction, the wall can only apply a force to the current sphere directed radially inward.

Let $r_1$ and $r_2$ denote the positions of the two pack spheres and $r_c$ denote the position of the current sphere. The relative positions of the two pack spheres to the current sphere is $r_{ic}=r_i-r_c$, i=1 or 2. These relative vectors point from the current sphere center to the i-th pack sphere center. Let $e_{ic}$ be the unit vector pointing along $r_{ic}$. The force the current sphere applies to each pack sphere and the wall must sum to its weight W. That gives the equation $$F_1 e_{1c} + f_2 e_{2c} + f_w e_{wc} = (0, 0, -W). \quad (23)$$

The unit vector $e_{wc}$, which points radially outward from the cylinder center, is given by $$e_{wc} = (x_c i + r_c j)/(x_c^2 + y_c^2)^{1/2} \quad (24)$$

As before in the three sphere case, the preferred implementation solves for the fi, i=1, 2, or w, but actually only their sign is needed: positive, negative or zero. Hence W is set to unity. Let $e_{ix}$ be the x component of the vector $e_{ic}$, i=1, 2, or w, and similarly for the y and z components. Then the solutions for the fi are given by $$f_1 = (e_{2y} e_{wx} - e_{2x} e_{wy})/\det e$$

$$f_2 = (e_{1x} e_{wy} - e_{1y} e_{wx})/\det e$$

$$f_w = (e_{1x} e_{2y} - e_{1y} e_{2x})/\det e \quad (25)$$

where $$\det e = -e_{1x} e_{2z} e_{wy} + e_{1y} e_{2z} e_{wx} + e_{1z}(e_{2x} e_{wy} - e_{2y} e_{wx}). \quad (26)$$

If an $f_i$, i=1, 2, or w, is negative, the force between the current sphere and that object is compressive and they stay in contact. If it is positive, the force is tensile and the current sphere will roll away from that object. In the unlikely event that it is zero, the implementation considers it tensile and has the current sphere roll away from the object, thereby trying to find a point of stability at lower altitude. If all three $f_i$ are negative, the sphere is in stable contact and is placed at its current position.

These stability calculations for two spheres and a wall are performed in the preferred implementation by Subroutine ST2S1W.

Detail of Subroutine FOBJ1

Returning to the subroutine FOBJ1, it finds the first object the descending current sphere encounters as it is "dropped" from the position selected by subroutine DROPSITE. There are three possible objects the current or selected sphere can encounter: (1) an already-placed pack sphere, (2) a water level, or (3) the catch net. A fourth object that may be encountered later is the cylinder wall, but because the current sphere is assumed to drop parallel to the cylinder wall, it cannot contact the wall until it rolls off some placed pack sphere.

The Catch Net

In accordance with the method aspect of the invention, the selected particle placement includes defining a catch net representative of buoyancy of a portion of the placed particles and positioning the catch net within the space based upon the placement of the portion of the placed particles. The selected particle is placed in non-overlapping relation with respect to the catch net. Preferred versions of the method include defining a pack surface for the placed particle, and positioning the catch net relative to the pack surface. The pack surface may comprise a top layer of the placed particles within the space, or preferably, within each of the subspaces. The particle surface optionally may correspond to an average of the south poles or south pole positions of the top layer of placed particles. The catch net may be positioned at a distance from the pack surface based upon a selected particle radius, such as an average particle radius of the top layer or another subset of the placed particles at the pack surface.

In the way of background, when simulating a particle pack, particularly one with a wide particle size distribution, if the volume fraction of large particles is much larger than that of small particles, the small particles can rattle down through the pack by falling through the interstitial spaces of the large particles. In many particulate materials, there are buoyancy or suspension considerations that would keep the small particles more or less well distributed throughout the pack. Examples of such buoyancy or suspension factors may include the nature or properties of the binder or other inter-particle medium or media, the interaction of the particles with the inter-particle medium or media, interactions among the particles themselves (such as electrical or magnetic interactions), interactions with external forces or fields that tend to disperse or suspend the particles, and similar phenomena.

In accordance with this aspect of the present invention, this buoyancy or suspension phenomena is simulated using a "catch net." The catch net comprises an assumed surface or construct to catch the current or selected particle as it is placed and to prevent that particle from passing a defined location or level which theoretically represents space occupied by smaller ones of the previously placed particles.

In the presently preferred implementation, a catch net is incorporated into the space, below which the south pole of the falling particles cannot descend. When a particle's south pole hits the catch net belonging to its cylinder, it is placed in the pack at that point, even if it is not touching any other particle. Preferably there is a separate catch net for each particle submode, and thus for each subspace or cylinder. Each catch net preferably covers the entire cross section of that submode's cylinder. If the current sphere's south pole hits that catch net, it is placed there. It does not see or respond to any other submode's catch net. The altitude of the catch net preferably is determined dynamically, that is, it can depend on which placed particles are being contacted.

The use of a catch net is not necessarily limited to a specific type or size of particle, or a particular size or geometry of the space or subspaces. In accordance with the presently preferred implementation, however, as noted, the particles comprise spheres and the characteristic dimension of each of the particles comprises a radius. The central string comprises a line, preferably the z axis, within the space. The space comprises a cylinder, and the subspaces comprise concentric cylinders disposed about the central string, each of the cylinders defining one of the subspaces and having a radius that corresponds to the radius of the particles in the category corresponding to that cylinder.

In accordance with the presently preferred implementation, the method further includes defining a pack surface for the placed particles, and the catch net positioning comprises positioning the catch net relative to the pack surface. Also in accordance with this implementation, the catch net positioning comprises positioning the catch net a distance from the pack surface based upon a selected particle radius.

The placed particles may be assumed to comprise a top layer, and the pack surface optionally but preferably comprises an average of the particle locations of the placed particles in the top layer. In this implementation, the particle surface corresponds to the south poles of the top layer placed particles and more specifically corresponds to an average of the south pole positions of the top layer placed particles.

In the presently preferred implementation, the catch net extends across the cross-sectional area of the space, across the cross-sectional areas of each of the subspaces.

In this preferred implementation, the catch net comprises N subnets, one of the subnets corresponding to each of the subspaces. Each of the concentric cylinders 1, 2, 3, . . . N has a circular cross-section perpendicular to the central string. In the preferred implementation, the catch net comprises a plurality N of subnets, or individual catch nets, one for each of the cylinders. Each of the subnets preferably extends over the cross-sectional area of the corresponding subspace or cylinder. The position or level of the catch net or subnet for each of these subspaces can and typically will differ from one another, although in some instances they may be at the same or nearly the same level.

Preferably, the positioning of the catch net comprises setting the catch net or each of the subnets at a selected distance from the top surface. This selected distance may be a user-defined quantity, or it may be dictated by the material being simulated or other factors. The catch net preferably is positioned at an altitude along the z-axis that is a function of the particle radius of particles corresponding to the mode or submode of the cylinder in which the catch net or subnet resides. The catch net or subnet preferably, but optionally, is some multiple of the particle radius, preferably one or two ratio, below the top layer or pack surface. Adjustments or offsets, however, may be used.

When the pack is first being formed so that not enough particles have yet been placed to adequately define a pack surface, the catch net may be defined as the bottom of the cylinder into which the particles are being dropped. In some instances, however, particularly where the specific application involves simulating a very large three-dimensional pack, it is often advantageous or desirable to avoid the edge effects of the flat bottom of the cylinder. Accordingly, in some instances the positioning of the catch net may comprise spacing the catch net from the base surface of the space. The spacing from the base surface, for example, may simulate the positioning of the catch net for a top layer of the placed particles, for example, the positioning of the catch net off of the base of the space may be done in a way that the bottom layer of placed particles simulate the shape, configuration and appearance of the top layer of particles after the particle pack has been constructed to include multiple layers.

This may be implemented by assigning as an initial catch net position for a k-th one of the subspaces $Z_{init}(k)$, assigning as the characteristic dimension of the particles of a k-th one of the particle categories $a_k$, assigning as the characteristic dimension of a small one of the particles amin of the particles and assigning as the characteristic dimension of a large one of the particles $a_{max}$. Below a threshold level the catch net positioning further comprises positioning the catch net for a k-th one of the particle categories at a catch net position $Z_{net}(k)$ within a k-th one of the subspaces determined by $$Z_{net}(k) = Z_{init} + H\ r\ a_k\ a_{min}/a_{max} \qquad (27)$$

where r represents a weighting coefficient and H represents a switching coefficient. The weighting coefficient preferably, but optionally, is assigned a random number. Below the threshold value the switching coefficient preferably is assigned a value of one, and above the threshold value the switching coefficient preferably is assigned a value of zero.

In the presently preferred implementation, the switching coefficient mechanism is implemented by a switch called ROUGHNET which, when true, invokes the random number generator to slightly change the altitude of the catch net so that the first set or layer of placed particles do not all have the same altitude. If ROUGHNET is false, the south poles of the first set of placed particles do have the same altitude because they hit the same catch net.

Let $Z_{init}$ be the initial altitude above which the pack will be built. It is specified by the user in the preferred implementation but its default preferably is zero. The initial catch net altitude for the k-th mode is $$Z_{net}(k) = Z_{init} + H\ r\ a_k\ a_{min}/a_{max} \qquad (28)$$

where r is a random number in [0, 1] $a_{min}$ is the smallest particle radius of all submodes belonging to the pack, $a_{max}$ is the largest, and H is unity if the ROUGHNET switch is true and zero if it is false. This expression for the catch net altitude holds until enough particles have been placed to establish a pack surface, i.e., until m (which is greater than or equal to $m_{min}$) is reached. No part of any particle is permitted to descend below $Z_{init}$ in this implementation.

The catch net preferably is positioned relative to the pack surface. The pack surface can be determined in a number of ways. It may he determined, for example, based on the large particles in the top layer, or another subset of the placed particles, e.g., such as the last particles placed.

The particle surface may be ascertained in the following manner. For each particle category k of the placed particles in the top layer, the program defines a particle radius $a_i$ for the placed particles i of that category k. For the cylinder k corresponding to the particle category k, the program assigns a cylinder radius $W_k$. The program also assigns a top layer particle number m(k) and determines values for m(k) by evaluating $$\sum_{\substack{i=1 \\ \text{Submode}(i) \leq k}}^{m(k)-1} a_i^2 < W_k^2 \leq \sum_{\substack{i=1 \\ \text{Submode}(i) \leq k}}^{m(k)} a_i^2, k = 1, 2, \ldots, N \qquad (29)$$

where N is the number of particle categories, e.g., the number of submodes. The program then determines the pack surface location using $$S = \frac{1}{m} \sum_{i=1}^{m} (Z_i - a_i) \qquad (30)$$

where S represents the pack surface and $Z_i$ represents the position of a center of a center one of the placed spheres.

In accordance with the preferred implementation, the surface altitude S of the pack is defined as the average south pole altitude of the last m placed particles where m is a positive integer that will be discussed below. This surface altitude is given by $$S = \frac{1}{m} \sum_{i=1}^{m} (Z_i - a_i) \qquad (31)$$

where $Z_i$ is the altitude of the center of Sphere i which is one of the last m placed particles and $a_i$ is its radius. Instead of using a single i-th particle radius in Eq. 31, one may generalize the expression by permitting $(Z_i - a_i)$ to be written $(Z_i - f(a_i))$ where $f(a_i)$ is a function of particle radius $a_i$. The preferred value for $f(a_i) = a_i$, but $f(a_i)$ may assume other forms, for example, such as $f(a_i)=na_i$ where n is a positive real or integer number.

Although the "surface" of a random particle pack may be defined in a number of ways, the surface preferably is defined only after the integer m is large enough that the falling spheres have covered the cylinder area. The k-th cylinder with radius $W_k$ has area $\pi W_k^2$. Let m be defined as the number of most recently placed spheres whose submodes have cylinder radii less than or equal to $W_k$ and whose summed cross-sectional area just exceeds or equals the k-th cylinder area. For the k-th submode, m is taken from the following condition. Let m(k) be the number m for the k-th submode. It is found from $$\sum_{\substack{i=1 \\ Submode(i) \leq k}}^{m(k)-1} a_i^2 < W_k^2 \leq \sum_{\substack{i=1 \\ Submode(i) \leq k}}^{m(k)} a_i^2, k = 1, 2, \ldots, N \qquad (32)$$

where N is the total number of submodes. The submode k for which this condition is satisfied first, that is, has the lowest m(k) becomes the m for the pack:

$$m=\text{MIN}[m(k)]. \qquad (33)$$

In the preferred implementation there is a minimum number $m_{min}$ for those unused packs that defeat the reasoning leading to the value for m given in Eqs. 32 and 33. The default value of $m_{min}$ may be assigned to a value of 12 in the preferred implementation.

Once a surface is established, its altitude S is determined by using Eq. 31. As the current sphere descends, if it hits a pack sphere much larger than itself, and if the TUNNEL switch is true, it will tunnel through the large sphere to check for possible cavities under the large particle. Therefore the catch net should be placed quite low so the current sphere can investigate possible cavities. If TUNNEL is false, the catch net does not need to be that low.

If the current sphere hits a sphere somewhat bigger than itself, then it is unlikely to tunnel because the surface sphere is not large enough to accommodate it in a cavity. Then the catch net need not be as deep.

Finally, if the current sphere hits a sphere smaller than itself, then it cannot penetrate too deeply into the pack so the catch net can be rather shallow.

Letting the subscript i denote the first pack sphere contacted, the catch net criteria are quantitatively summarized as follows:

If $a_i/a_c<1$, then the catch net is shallow:

$$Z_{net}(k)=S-a_i. \qquad (34a)$$

If $1 \leq a_i/a_c<a_x$, where $a_x$ preferably is $\sqrt{6}+2$, then the catch net is moderate:

$$Z_{net}(k)=S-2a_c. \qquad (34b)$$

If $a_i/a_c \geq a_x$, where $a_x$ preferably is $\sqrt{6}+2$, then the catch net is deep:

$$Z_{net}(k)=-2a_c-a_i. \qquad (34c)$$

The value of $a_x$ represents the sizes required for a current sphere to fit into a cavity formed by larger spheres, which preferably assumes a value of ($\sqrt{6}+2$). If the centers of four identical larger spheres form a regular tetrahedron, and a smaller sphere just fits into the interstitial space of the tetrahedron, then the ratio of the smaller sphere to larger sphere diameter is $\sqrt{6}+2$ in preferred implementation.

Further in accordance with the preferred implementation, the code monitors the selected or current particle placement to identify the occurrence of the following sequence of events:

1. The catch net is set at an altitude when the current sphere hits the i-th pack sphere.
2. Then the current sphere rolls off the i-th sphere and loses contact with it.
3. When it hits another pack sphere, the catch net is set above the current altitude of the current sphere's south pole.

If this series of events is detected, the current sphere is raised (its position is adjusted upward) until its south pole is at the new catch net altitude, and it is then placed there.

The Water Level

In accordance with another aspect of the invention, the placement of the particles comprises defining a water level representative of a level of a portion of the placed particles that are smaller than the selected particle and represent a surface of the smaller placed particles, and positioning the water level within the space based upon the smaller particle surface. The current or selected particle is then placed in non-overlapping relation with respect to the water level.

The water level serves a different purpose than the catch net. Recall that the particle pack according to the preferred implementation is constructed using a series of concentric cylinders, one cylinder defined for each particle category or submode. Recall further that the centers of particles in this implementation cannot pass outside their own corresponding and constraining cylinder into which they are dropped. Large cylinders are used for large particles and small cylinders for small particles, unless the user for some reason designates otherwise. The cylinder construct facilitates or permits use of the reduced dimension approach to particle pack construction. Its purpose is to prevent the program code from having to fill large cylinder volumes with potentially very large numbers of small particles.

This approach, however, creates the problem that the large cylinders will contain empty space into which large spheres can roll during simulated particle placement where, in a corresponding physical particle pack such as the one being simulated, this would not occur. In the actual pack, the smaller particles would be included even in the regions comprising the larger cylinders, and these smaller particles would be encountered to prevent such rolling.

The water level simulates this presence in the larger cylinder areas of smaller particles that, according to the presently preferred implementation, have not been placed in the larger cylinders.

There are a number of methods or approaches for selecting or setting the water level. According to one such approach, the water level positioning comprises determining an average location of the particle locations along the central string of the particles of the portion of placed particles that are smaller than the current or selected particle, and positioning the water level at the average location. The water level may be set at the average altitude of the small particle "surface" as if the outside cylinders were filled with small particles. Then when a large particle or sphere descends onto the water level, the particle, and preferably its south pole, is stopped there as it would be if that volume had been filled with the smaller particles.

In the presently preferred implementation, wherein the plurality of subspaces (here concentric cylinders) is used, the water level comprises a plurality of subspace water levels, preferably one subspace water level for each subspace or cylinder. These water level positions may and typically will differ from one another as the particle pack is constructed. The water level positioning optionally, but preferably, comprises assigning a subspace water level position to a portion of the subspace water levels. The portion of the subspace water levels preferably correspond to one water level for each cylinder except the first cylinder. In the preferred implementation, all of the cylinders except the first or central one, containing the smallest particles, has a subspace water level and corresponding subspace water level position.

In the presently preferred implementations, the water level positioning comprises using an offset to position the water level, or an offset relative to the average location of the particle locations. Preferably, the water level positioning comprises using an offset for each of the subspace water level positions. The water level positioning similarly may comprise using an offset for each of the subspace water level positions.

In the presently preferred implementation, the water level altitude for the i-th cylinder (i>1) is defined as the average exposed north pole altitude of all particles with radius less than ai. The user may raise or lower this level by adding a user-defined offset, but the default for this offset in this implementation is zero. This water level exists between the i-th cylinder wall of radius Wi and the next smaller cylinder wall of radius $W_{i-1}$. Thus, the spaces between different cylinder walls have different water levels. The cylinder corresponding to the smallest particle's submode has no water level, only a catch net.

If a larger sphere is descending onto the pack near the center cylinder, it may hit the center cylinder's pack of small particles and tend to roll off its edge and fall to the floor of the pack or fall until it hits another large sphere. Thus, the pack would segregate with larger particles outside smaller particles. With the water level in place, however, if the larger sphere rolls off the pack in the central cylinder, it simply "floats" on the water level which is at the same level as the "surface" of the central cylinder pack. Thus, any time a descending sphere hits a water level, it is placed where it is, just as was done with the catch net. Ordinarily, water levels will be higher than catch nets, although this is not always true.

Search for the First Object Encountered

A free-falling current sphere can encounter the following situations. It might hit a single pack sphere. If so, FOJB2 is called. It can hit two pack spheres simultaneously. If so, FOBJ3 is called. It can hit three or more pack spheres simultaneously. If so STABLE is called to see if it is in stable contact with any triplet of these spheres. Hitting two or more pack spheres simultaneously is highly improbable in a double precision random code but not so improbable if the pack is semi-ordered, and hence these scenarios are included in the preferred implementation.

In addition, the south pole of the current sphere may hit the catch net or a water level before it hits any other sphere. In either case, it is placed where it is.

A pack sphere, e.g., the j-th sphere, is a candidate for being the first object encountered by the descending current sphere if their two radii overlap, i.e., if $$(X_c - X_j)^2 + (Y_c - Y_j)^2 < (a_c + a_j)^2 \quad (35)$$

If there were no other obstacles in the way, the current sphere would strike Sphere j at an altitude of $$Z_c(j) = Z_j + [(a_c + a_j)^2 - (X_c - X_j)^2 - (Y_c - Y_j)^2]^{1/2}. \quad (36)$$

Once the pack has grown to many spheres, efficiency can be greatly enhanced to the extent that as many spheres as possible be excluded from the detailed considerations of the above two equations, while not unduly adversely affecting the accuracy of the simulation in representing the physical particle pack being simulated. For example, if $|x_c - x_j|$ or $|y_c - y_j|$ alone were greater than $(a_c + a_j)$, then there is no need to check the square of their sums as above.

The processing demands are reduced in the preferred implementation because all spheres whose north poles have submerged beneath the catch net are off limits and need not be included. Simply flagging them by putting a minus sign in front of their mode or submode number indicates that no calculations are to be done to see if they are in range of the descending current sphere. Furthermore, in this implementation the program keeps track of the lowest index number for any sphere whose north pole protrudes above that mode's catch net so that the eventually large list of particles beneath the catch net are not searched at all.

Submergence of a placed pack sphere beneath the water level, however, is not necessarily grounds for dismissing it from consideration. The current sphere may roll into a cylinder for which the water level is different and the pack sphere may again become a candidate for contact.

If the current sphere is dropped far enough outside a set of cylinders that there is no chance for a first contact with the spheres belonging to those cylinders, then in the preferred implementation such sphere(s) are dismissed from further consideration. If the submode number of a sphere belongs to an out-of-range cylinder, no further processing is required in the preferred implementation. Let $W_k$ be the cylinder wall radius for the k-th particle submode. If $$(W_k + a_k)^2 \leq X_c^2 + Y_c^2 \quad (37)$$

then no k-th mode sphere is a candidate for first contact with the descending current sphere in this implementation.

In summary then, FOBJ1 searches the list of all placed pack spheres above the catch net for the submode to which the current sphere belongs, excluding all placed spheres that may be in interior cylinders that the current sphere cannot contact or overlap. The possibility of overlap in the x directions is checked, followed by the possibility of overlap in the y directions, followed by a direct calculation of overlap. The altitude $z_c(j)$ at which the current sphere would contact Sphere j is stored and that sphere is rejected if other placed pack spheres have a higher contact altitude. Again, if no pack spheres make contact before the current sphere reaches the catch net or water level, it stops and is placed there.

Detail of Subroutine FOBJ2

Subroutine FOBJ2 finds the second object to be contacted by the descending current sphere. FOBJ2 would only have been called if the current sphere had first contacted a single pack sphere that has been denoted Sphere 1. If it had contacted the catch net or water level, the current sphere would have been placed there and FOBJ2 would never have been called. If it had contacted more than one sphere simultaneously, FOBJ3 and/or STABLE would have been called. FOBJ2 is called only if a single pack sphere's northern hemisphere has been touched.

When the current sphere touches the northern hemisphere of Sphere 1, it begins to roll down the path of steepest descent which is Sphere 1's longitudinal line passing through the point of contact. The volume swept out as the current sphere descends along this path toward the equator is called the roll corridor. The end of the roll corridor is either where the current sphere's center reaches the equatorial plane of the Sphere 1, reaches its cylinder wall, or reaches the catch net or water level, whichever is higher. The preferred implementation identifies all other pack spheres that protrude into the roll corridor.

Processing can be somewhat simplified if the cylinder wall is assumed to be the boundary that the center of the current sphere cannot pass, rather than the boundary through which its leading edge equator cannot pass.

If the center of the current sphere intersects the cylinder wall during descent, then that point is the end of the roll corridor because it will at least have found the wall as its second object if no other pack sphere has been contacted first.

The beginning of the roll corridor is then the place of initial contact between the current sphere and Sphere 1. The current sphere's polar angle at that initial contact is given by $$\theta_{ci} = \cos^{-1}[(Z_c - Z_1)/(a_c + a_1)]. \tag{38}$$

The end of the roll corridor $\theta_{cf}$ will either be at the equatorial plane of Sphere 1 or where the center of the current sphere intersects the catch net, the water level, or the cylinder wall. If it is at the equatorial plane, then $$\theta_{cf} = \pi/2. \tag{39}$$

If the altitude of the catch net $Z_{net} \geq Z_1 - a_c$, then $$\theta_{cf} = \cos^{-1}[(Z_{net} + a_c - Z_1)/(a_c + a_1)]. \tag{40}$$

If the altitude of the water level $Z_w \geq Z_1 - a_c$, then $$\theta_{cf} = \cos^{-1}[(Z_w + a_c - Z_1)/(a_c + a_1)]. \tag{41}$$

The last possibility is that the roll corridor ends with an intersection of the cylinder wall. Let $\phi_c$ be the azimuthal position at which the current sphere has touched Sphere 1. It is given by $$\phi_c = \tan^{-1}[(Y_c - Y_1)/(X_c - X_1)]. \tag{42}$$

The radial position of the current sphere as it descends Sphere 1 as a function of $\theta_c$ is given by $$\{[X_1 + (a_c + a_1)\sin\theta_c \cos\phi_c]^2 + [Y_1 + (a_c + a_1)\sin\theta_c \sin\phi_c]^2\}^{1/2}. \tag{43}$$

If this radial position is equal to the cylinder radius W for some value of $\theta_c$ between 0 and $\pi/2$, then the roll corridor intersects the cylinder wall. Setting this expression equal to W, squaring both sides, and solving the quadratic equation for $\sin\theta_c$ gives $$\sin\theta_{cf} = \frac{-(X_1\cos\varphi_c + Y_1\sin\varphi_c) \pm \sqrt{(X_1\cos\varphi_c + Y_1\sin\varphi_c)^2 + W^2 - X_1^2 - Y_1^2}}{a_c + a_1} \tag{44}$$

Because $\theta_{cf}$ is a polar angle, it lies in the range $[0, \pi]$. Therefore, $\sin\theta_{cf}$ can never be negative. If both right-hand side solutions of Eq. 44 are greater than unity, there is no solution and the current sphere does not intersect the cylinder wall. If both are less than or equal to unity, then we choose the larger one.

The presently preferred implementation conducts appropriate processing to evaluate each of these possible circumstances. Before evaluating Eq. 44, the program code according to this implementation adds the global radial position of Sphere 1 to the sum of the radii of Sphere 1 and the current sphere. If this sum is less than or equal to W, then the sphere cannot hit the cylinder wall in any case so the more involved evaluation above is unnecessary and preferably is not performed.

The end of the roll corridor is the minimum $\theta_{cf}$ of Eqs. 39, 40, 41, and 44. If the current sphere encounters the catch net or water level, it is placed there.

The preferred implementation also checks for all pack spheres whose volumes intrude upon the roll corridor swept out by the current sphere which covers the are from $\theta_{ci}$ to $\theta_{cf}$ and azimuth $\phi_c$ on Sphere 1. If there is a $\theta_c$ with smaller value than the end of the roll corridor $\theta_{cf}$ at which the current sphere encounters one or more pack spheres, then the sphere or spheres touched are noted. Program control is then passed to subroutines that deal with simultaneous contact of two or more spheres, as described herein.

If no pack spheres overlap the roll corridor, then the current sphere is placed if it hits the catch net or water level. If it hits neither of these, then it rolls to the equator and drops from there. At that point it is a free falling sphere again so FOBJ1 is recalled.

We now turn our attention to finding which placed pack spheres overlap the roll corridor and at what point the current sphere would strike them as it descends from $\theta_{ci}$. The term "global coordinate system" is used herein when discussing a single coordinate system in which the entire pack is defined. Capital letters are used when referring to a global coordinate system, e.g., $\vec{R}_i = (X_i, Y_i, Z_i)$ for the Cartesian position of the i-th sphere.

A local coordinate system, on the other hand, is one whose origin is at the center of one of the spheres and whose axes are parallel to the global axes. We use small letters to define it, e.g., $\vec{r}_i = (x_i, y_i, z_i)$ for a position relative to the center of the i-th sphere.

Consider the j-th pack sphere. Its center is at global position $R_j = (X_j, Y_j, Z_j)$ and its radius is $a_j$. In the global coordinate system, the position of the current sphere as it descends along Sphere i is $$\vec{R}_c = \vec{R}_i + (a_c + a_i)(\sin\theta_c \cos\phi_c \hat{i} + \sin\theta_c \sin\phi_c \hat{j} + \cos\theta_c \hat{k}). \tag{45}$$

The current sphere rolls into Sphere j if there is a solution $\theta_c$ that lies in the interval $\theta_{ci} < \theta_c < \theta_{cf}$ to the equation $$|\vec{R}_c - \vec{R}_j| = a_c + a_j. \tag{46}$$

If this equation can be satisfied at all, it will have two solutions: one where the current sphere touches Sphere j from above and another where the current sphere touches Sphere j from below. (If it just nicks Sphere j, these two solutions can be at the same $\theta_c$, but if Sphere j is just nicked, the preferred implementation considers that a miss.) We are only interested in the top or smaller $\theta_c$ solution, and then only if the top $\theta_c$ lies in the roll corridor range.

Explicitly, the equation to be solved is $$[X_i - X_j + (a_c + a_i)\sin\theta_c \cos\phi_c]^2 + [Y_i - Y_j + (a_c + a_i)\sin\theta_c \sin\phi_c]^2 + [Z_i - Z_j + (a_c + a_i)\cos\theta_c]^2 = (a_c + a_j)^2 \tag{47}$$

which, defining $X_{ij} \equiv X_i - X_j$, $Y_{ij} \equiv Y_i - Y_j$, and $Z_{ij} \equiv Z_i - Z_j$, can be rewritten $$(X_{ij}\cos\phi_c + Y_{ij}\sin\phi_c)\sin\theta_c + Z_{ij}\cos\theta_c = [(a_{j-ai})(a_j + a_i + 2a_c) - R_{ij}^2]/[2(a_c + a_i)] \tag{48}$$

where $$R_{ij}^2 = X_{ij}^2 + Y_{ij}^2 + Z_{ij}^2. \tag{49}$$

This equation has the form $$A \sin\theta_c + B \cos\theta_c = C \tag{50}$$

where $$A = X_{ij} \cos \phi_c + Y_{ij} \sin \phi_c \quad (51)$$

$$B = Z_{ij} \quad (52)$$

$$C = [(a_j - a_i)(a_j + a_i + 2a_c) - R_{ij}^2]/[2(a_c + a_i)]. \quad (53)$$

Dividing through by $\sqrt{(A^2 + B^2)}$, we obtain $$\cos \alpha \sin \theta_c + \sin \alpha \cos \theta_c = C/\sqrt{(A^2 + B^2)} \quad (54)$$

where $$\cos \alpha = A/\sqrt{(A^2 + B^2)} \quad (55)$$

and $$\sin \alpha = B/\sqrt{(A^2 + B^2)}. \quad (56)$$

A common trigonometric identity turns Eq. 54 into $$\sin(\theta_c + \alpha) = C/\sqrt{(A^2 + B^2)} \quad (57)$$

which has solution $$\theta_c = \sin^{-1}[C/\sqrt{(A^2 + B^2)}] - \alpha \quad (58)$$

where $$\alpha = \tan^{-1}[A/B]. \quad (59)$$

If $|C/\sqrt{(A^2+B^2)}| > 1$, then there is no solution and the j-th sphere does not overlap the roll corridor.

The FORTRAN function ATAN2 (A, B) or its equivalent in other programming languages uses information on the signs of A and B to determine in which quadrant α lies so it is uniquely defined. The arcsine, however, has two solutions. One solution is the principal value which lies in $[-\pi/2, \pi/2]$ and is found by the standard FORTRAN function ASIN or its equivalent. The other solution is π minus this principal value. These two solutions comprise the two solutions for the current sphere contacting Sphere j on either side along the longitudinal line defined by azimuthal angle $\phi_c$. Denoting the principal value by capitalizing the arcsine, the two solutions are $$\theta_{c1} = \text{Sin}^{-1}[C/\sqrt{(A^2+B^2)}] - \alpha \quad (60a)$$

and $$\theta_{c2} = \pi - \text{Sin}^{-1}[C/\sqrt{(A^2+B^2)}] - \alpha. \quad (60b)$$

If either of these θ lie outside $[0, 2\pi]$, then $2\pi$ must be added or subtracted enough times to bring the solutions back into $[0, 2\pi]$. If neither of these solutions lie in the open interval $(\theta_{ci}, \theta_{cf})$, then the current sphere does not contact Sphere j. If one solution does lie in $(\theta_{ci}, \theta_{cf})$, that is the position at which the second contact is made. If both do, the lesser of the two solutions is the position of second contact.

Finally, whichever pack sphere has the smallest $\theta_c$ is Sphere 2. That point of contact is denoted $\theta_{cf}$. If two or more pack spheres are contacted simultaneously, then all their index numbers are returned by FOBJ2. If the cylinder wall and one or more pack spheres are contacted simultaneously, their index numbers are returned and the flag indicating a wall contact is activated.

As the preferred implementation searches through the pack spheres to find which is touched first, there are several efficiency criteria that can be used to eliminate most spheres from the detailed consideration of the above equations.

First, if the roll corridor is far enough away from the global Z axis, then the current sphere may not be able to approach some inner cylinders closely enough to touch their spheres. Therefore, those pack spheres whose mode number indicates they belong to the inner cylinders need not be considered further. The preferred implementation can determine which cylinder's spheres can never intersect the current sphere's roll corridor.

Because the current sphere rolls down a longitudinal line on Sphere i, when viewed from above, its projection is a straight line segment on the XY plane with beginning point $(X_{ci}, Y_{ci})$ and ending point $(X_{cf}, Y_{cf})$ where $$X_{ci} = X_i + (a_c + a_i) \sin \theta_{ci} \cos \phi_c \quad (61a)$$

$$Y_{ci} = Y_i + (a_c + a_i) \sin \theta_{ci} \cos \phi_c \quad (61b)$$

$$X_{cf} = X_i + (a_c + a_i) \sin \theta_{cf} \cos \phi_c \quad (61c)$$

$$Y_{cf} = Y_i + (a_c + a_i) \sin \theta_{cf} \cos \phi_c. \quad (61d)$$

To find whether this line segment comes close enough to the l-th cylinder to touch any of its spheres, the preferred implementation turns the current sphere's position into a pair of parametric equations:

$$X_c = X_{ci} + (X_{cf} - X_{ci})s \quad (62a)$$

$$Y_c = Y_{ci} + (Y_{cf} - Y_{ci})s \quad (62b)$$

where s is a dimensionless parameter that is zero at the beginning of the roll corridor and unity at the end. In order for the current sphere to have any chance of touching an l-th mode sphere, it must come closer than the sum of its radius plus an l-th sphere's radius from the l-th cylinder wall which has radius $W_l$. In other words, some portion of the roll corridor must come within $W_l + \alpha_l + \alpha_c$ of the global Z axis. This condition is expressed by $$X_c^2 + Y_c^2 = (W_l + a_l + a_c)^2 \quad (63)$$

for a value s somewhere in the open interval $[0, 1]$. If Eq. 63 is never satisfied, then the current sphere cannot touch any of the l-th mode spheres. Explicitly written, Eq. 63 is a quadratic equation in s:

$$As^2 + 2Bs + C = 0 \quad (64)$$

where $$A = (X_{cf} - X_{ci})^2 + (Y_{cf} - Y_{ci})^2 \quad (65)$$

$$B = X_{ci}(X_{cf} - X_{ci}) + Y_{ci}(Y_{cf} - Y_{ci}) \quad (66)$$

$$C = X_{ci}^2 + Y_{ci}^2 - (W_l + \alpha_l + \alpha_c)^2. \quad (67)$$

The solutions are $$s = \frac{-B \pm \sqrt{B^2 - AC}}{A} \quad (68)$$

If $B^2 - AC$ is negative, there is no solution. If it is zero, there is only one real solution which means the roll corridor just grazes the l-th cylinder, in which case it is considered a miss. If it is positive, there are two real solutions. The preferred implementation solves for both of them, and checks to determine whether either one lies in the open interval $[0, 1]$. If one or both lie in this interval, the l-th mode spheres are candidates for touching the descending current sphere.

To find which cylinders are inaccessible to the current sphere, the preferred implementation starts with the innermost cylinder (l=1) and continues outwardly until it reaches a cylinder that is big enough that it is accessible. All larger cylinders also will be accessible.

There also is a simple altitude criteria to delimit detailed consideration of pack spheres as candidates for touching the current sphere. The global altitudes of the beginning and end of the roll corridor are $$Z_{ci} = Z_i + (a_c + a_i) \cos \theta_{ci} \quad (69a)$$

$$Z_{cf} = Z_i + (a_c + a_i) \cos \theta_{cf}, \quad (69b)$$

respectively. Therefore, if a j-th pack sphere lies below the end of the roll corridor by the amount $$Z_j < Z_{cf} - a_c - a_j \quad (70a)$$

or lies above the top of the roll corridor by the amount $$Z_j \geq Z_{ci} + \alpha_c + \alpha_j, \quad (70b)$$

then it is not a candidate for touching the current sphere.

Likewise, spheres lying beyond the roll corridor in the x and y directions need not be further considered, i.e., if $$X_j \leq X_{cf} - \alpha_c - \alpha_j \quad (70c)$$

$$Y_j \leq Y_{cf} - \alpha_c - \alpha_j \quad (70d)$$

or $$X_j \geq X_{ci} + \alpha_c + \alpha_j \quad (70e)$$

$$Y_j \geq Y_{ci} + \alpha_c + \alpha_j, \quad (70f)$$

then the j-th sphere lies beyond the roll corridor in the horizontal plane and is not a candidate for touching the current sphere.

Detail of Subroutine FOBJ3

Subroutine FOBJ3 finds the third object to be contacted by the descending current sphere when it is already in contact with two and only two other objects. There are only two possibilities for the two initial contacts: (1) both are placed pack spheres or (2) one is a placed pack sphere and the other is the cylinder wall for the submode of the current sphere. Each of these possibilities will now be addressed in turn.

Touching Two Spheres

It is presumed at the outset of this discussion that the two touching spheres, i and j, are in stable (compressive) contact, subroutine STABLE already having been called to remove them if they are not. A roll corridor follows a circle defined where the current sphere is in contact with both Spheres i and j. Of course, the current sphere cannot touch both spheres unless the condition $r_{ji} < \alpha_i + \alpha_j + 2\alpha_c$ is satisfied where $r_{ji}$ is the center-to-center distance between Spheres i and j.

The current sphere's descent along this roll corridor will be defined by a single variable $\phi_c'$. This variable is the azimuthal angle of a local tilted coordinate system whose origin is in the center of Sphere i, with z axis tilted so it passes through the center of Sphere j, and with x axis swung upward so that it lies in a vertical plane. In that coordinate system (which is denoted herein by primes), $\phi_c'$ alone describes the current sphere's position along the roll corridor. In the unlikely event that the current sphere finds itself perfectly balanced on Spheres i and j so that $\phi_c'=0$, then a random number generator determines in which direction the current sphere will roll—toward negative $\phi_c'$ or toward positive $\phi_c'$.

To find the coordinates of a pack sphere, say the k-th sphere, in this primed coordinate system, the preferred implementation first translates the global sphere positions to the unprimed local coordinate system whose origin is at the center of Sphere i but whose axes are parallel to the global axes:

$$\vec{r}_{ki} = \vec{R}_k - \vec{R}_i. \quad (71)$$

Capital letters are used herein to denote coordinates in the global coordinate system, small letters in the unprimed local system (local to Sphere i), and primed small letters in the local tilted coordinate system.

The Euler matrix used to rotate the unprimed into the primed coordinate system is given by $$A = \begin{pmatrix} -\cos\theta_{ji}\cos\varphi_{ji} & -\cos\theta_{ji}\sin\varphi_{ji} & \sin\theta_{ji} \\ \sin\varphi_{ji} & -\cos\varphi_{ji} & 0 \\ \sin\theta_{ji}\cos\varphi_{ji} & \sin\theta_{ji}\sin\varphi_{ji} & \cos\theta_{ji} \end{pmatrix} \quad (72)$$

where $\theta_{ji}$ and $\phi_{ji}$ are the polar and azimuthal angles of Sphere j relative to Sphere i and are given by $$\cos \theta_{ji} = (Z_j - Z_i)/r_{ji} \quad (73a)$$

and $$\phi_{ji} = \tan^{-1}[(Y_j - Y_i)/(X_j - X_i)]. \quad (73b)$$

This Euler matrix allows the preferred implementation to obtain the k-th sphere's position in the primed coordinate system as $$\vec{r}_{ki}' = A \cdot \vec{r}_{ki}. \quad (74)$$

The current sphere's initial position in the primed coordinate system is given in like manner:

$$\vec{r}_{ci} = \vec{R}_c - \vec{R}_i \quad (75)$$

$$\vec{r}_{ci}' = A \cdot \vec{r}_{ci}. \quad (76)$$

Now that the three components of the vector $\vec{r}_{ci}'$ have been obtained, the preferred implementation can find the initial azimuthal position $$\phi_{ci}' = \tan^{-1}(y_{ci}'/x_{ci}'). \quad (77)$$

If $\phi_{ci}'$ is positive, the current sphere will roll toward higher positive values. If it is negative, it will roll toward more negative values (higher in magnitude). In the unlikely case that it is zero, a random number generator chooses which direction it will roll.

The polar angle of the center of the current spheres in the primed coordinate system is constant as long as it is in the roll corridor. It is obtained from the law of cosines as $$\cos \theta_c' = [r_{ji}^2 + (\alpha_c + \alpha_i)^2 - (\alpha_c + \alpha_j)^2][2\, r_{ji}(\alpha_c + \alpha_i)]^{-1} \quad (78)$$

with $$\sin \theta_c' = +[1 - \cos^2\theta_c']^{1/2}. \quad (79)$$

There are several possible outcomes as the current sphere descends its roll corridor. It can hit the catch net or water level;

lose contact with Sphere i or Sphere j or both simultaneously;

hit the cylinder wall; or hit another pack sphere or several pack spheres simultaneously.

The roll corridor ends when the current sphere encounters the first of these situations. The preferred implementation then finds the $\phi_c'$ at which one of these events happens. The event with the smallest magnitude for $\phi_c'$ will be the bottom of the roll corridor and will be denoted $\phi_{cf}'$.

Hitting the Catch Net or Water Level

First, the preferred implementation finds the global altitude of the current sphere as a function of $\phi_c'$:

$$\vec{R}_c = \vec{R}_i + A^{-1} \cdot \vec{r}_c' \tag{80}$$

where the inverse Euler matrix is equal to its transpose $A^{-1} = A^T$ because of its orthogonality. The current sphere's global Z component is given by $$Z_c = Z_i + (\alpha_c + \alpha_i)(\sin \theta_{ji} \sin \theta_c' \cos \phi_c' + \cos \theta_{ji} \cos \theta_c'). \tag{81}$$

Its south pole hits the catch net if $Z_c = Z_{net} + \alpha_c$. Solving for the primed azimuthal angle $\phi_c'$ at which this equation may be satisfied, we have $$\cos\phi_c' = \frac{\dfrac{Z_{net} + a_c - Z_i}{a_c + a_i} - \cos\theta_{ji}\cos\theta_c'}{\sin\theta_{ji}\sin\theta_c'} \tag{82}$$

where the sign of $\phi_c'$ is the same as the sign of $\phi_{ct}'$, the angle at the top of the roll corridor. If this equation does not have a real solution in $[0, \pi/2]$, then the current sphere does not reach the catch net in this roll corridor. If $\phi_c'$ is outside the range $[0, \pi/2]$, then units of $2\pi$ are either added or subtracted from $\phi_c'$ until it does lie within that range. Because neither $\theta_{ji}$ nor $\theta_c'$ can ever be zero or $\pi$, Eq. 82 is never singular.

The preferred implementation also can find which water level the current sphere might hit. Water level altitudes between adjacent cylinder walls are generally different as the pack is constructed. The only condition under which the current sphere might contact the k-th water level $Z_w(k)$ is if and only if the distance $P_c$ of the current sphere from the global Z axis lies between cylinder wall radii $W_{k-1}$ and $W_k$ at the point of contact. $P_c$ is given by $$P_c = (X_c^2 + Y_c^2)^{1/2} \tag{83}$$

where $X_c$ and $Y_c$ can be obtained from Eq. 80 as $$X_c = X_i + (a_c + a_i)(-\cos\theta_{ji}\cos\phi_{ji}\sin\theta_c'\cos\phi_c' + \sin\phi_{ji}\sin\theta_c'\sin\phi_c' + \sin\theta_{ji}\cos\phi_{ji}\cos\theta_c') \tag{84a}$$

and $$Y_c = Y_i + (\alpha_c + \alpha_i)(-\cos\theta_{ji}\sin\phi_{ji}\sin\theta_c'\cos\phi_c' - \cos\phi_{ji}\sin\theta_c'\sin\phi_c' + \sin\theta_{ji}\sin\phi_{ji}\cos\theta_c') \tag{84b}$$

Using the square of $P_c$ rather than Eq. 83, the water level checked for contact is $Z_w(k)$ if $W_{k-1}^2 < P_c^2 \leq W_k^2$. Actually, each annular region between the (k−1)-th and k-th cylinder walls is checked to see if the roll corridor has a possibility of contacting the water level there.

The expression for the $\phi_c'$ at which the south pole of the current sphere touches the k-th water level is the same as Eq. 82 with $Z_{net}$ replaced by $Z_w(k)$. Then the end of the roll corridor $\phi_{cf}'$ is either $\pm \pi/2$ or a contact point with the catch net or a water level as given by Eq. 82.

Losing Contact with One or Both Spheres

The preferred implementation also can determine the $\phi_c'$ at which the current sphere will lose contact with either Sphere i or j or both if it encounters nothing else as it descends its roll corridor.

Of the two spheres, i and j, the one whose center is higher by the subscript u and the one whose center is lower is denoted by 1. Their global positions are $(X_u, Y_u, Z_u)$ and $(X_l, Y_l, Z_l)$ and their radii are $\alpha u$ and $a_l$, respectively. We always have that $Z_u \geq Z_l$. Consider the unprimed coordinate system whose origin is in the center of the lower sphere and whose axes are parallel to the global axes. Let $\theta_c$ and $\phi_c$ be the polar and azimuthal angular position of the current sphere in the unprimed local coordinate system centered in the lower sphere.

As before, the primed coordinate system is the system obtained by tilting the unprimed z axis into the center of the upper sphere and then rotating the xy axes of that tilted coordinate system about its z' axis until its x' axis is pointing as steeply upward as possible, i.e., has a maximum positive projection onto the unprimed z axis. This rotation is what Eq. 72 does if i is replaced by l and j by u. The polar and azimuthal angular positions of the current sphere in the tilted coordinate system are $\theta c'$ and $\phi c'$, respectively where $\cos \theta_c'$ is given by Eq. 78 with the same change in indices mentioned in the previous sentence.

The current sphere will lose contact with the upper sphere first. If both lower and upper spheres are at the same altitude, it will lose contact with them both simultaneously. To find the $\phi c'$ position at which the current sphere loses contact with the upper sphere, the preferred implementation finds the two longitudinal lines of the lower sphere in the unprimed coordinate system along which the current sphere would just nick the upper sphere if it were descending along those longitudinal lines. The two $\phi_c$ at which that happens are the ends of the roll corridor at which the current sphere would lose contact with the upper sphere and roll on the lower alone. Because the current sphere is rolling down only one side of the roll corridor, only that side's $\phi_c$ is of interest.

In the unprimed local coordinate system, the current sphere is at $$\vec{r}_c = (a_c + a_l)(\hat{i} \sin \theta_c \cos \theta_c + \hat{j} \sin \theta_c \sin \phi_c + \hat{k} \cos \theta_c) \tag{85}$$

and the upper sphere is at $$\vec{r}_u = r_u(\hat{i} \sin \theta_u \cos \theta_u + \hat{j} \sin \theta_u \sin \phi_u + \hat{k} \cos \theta_u). \tag{86}$$

Consider the equation $$|\vec{r}_c - \vec{r}_u| = a_c + a_u. \tag{87}$$

If both sides are squared and written explicitly, we obtain $$[(a_c + a_l)^2 \sin \theta_c \cos \phi_c - x_u]^2 + [(a_c + a_l)^2 \sin \theta_c \sin \phi_c - y_u]^2 + [(a_c + a_l)^2 \cos \theta_c - z_u]^2 = (a_c + a_u)^2 \tag{88a}$$

which can be rewritten $$\frac{r_u^2 + (a_c + a_l)^2 - (a_c + a_u)^2}{2(a_c + a_l)} = \tag{88b}$$

$$x_u \sin\theta_c \cos\varphi_c + y_u \sin\theta_c \sin\varphi_c + z_u \cos\theta_c.$$

The components $x_u$, $y_u$, and $z_u$ are given in Eq. 86. If they are substituted into Eq. 88b and both sides are divided by $r_u$, we obtain $$\frac{r_u^2 + (a_c + a_l)^2 - (a_c + a_u)^2}{2(a_c + a_l)r_u} = \tag{89}$$

$$\sin\theta_u \cos\varphi_u \sin\theta_c \cos\varphi_c + \sin\theta_u \sin\varphi_u \sin\theta_c \sin\varphi_c + \cos\theta_u \cos\theta_c$$

where we recognize the left-hand side as $\cos\theta_c'$, the polar angle in the primed coordinate system which is constant as the current sphere descends the roll corridor. Now Eq. 89 can be written as $$\cos\theta_c' = \sin\theta_u \sin\theta_c(\cos\phi_u \cos\phi_c + \sin\phi_u \sin\phi_c) + \cos\theta_u \cos\theta_c \quad (90a)$$

which through a trigonometric identity can be written $$\cos\theta_c' = \sin\theta_u \sin\theta_c \cos(\phi_c - \phi_u) + \cos\theta_u \cos\theta_c. \quad (90b)$$

We wish to solve for $\theta^c$ from this equation. For a given $\phi_c$, the $\theta_c$ solution has three possibilities:

1. There are two $\theta_c$ solutions if the current sphere hits the upper sphere as it rolls down the $\phi_c$ longitudinal line of the lower sphere—one solution where it touches the upper sphere from above and the other where it touches from below;
2. There is one solution (the two solutions having become degenerate) where the current sphere just nicks the upper sphere while rolling along the $\phi_c$ longitudinal line; and
3. There are no real solutions, meaning the current sphere altogether misses the upper sphere while rolling along the $\phi_c$ longitudinal line.

The second possibility is the one of current interest because that is the point at which the current sphere can lose contact with the upper sphere and roll on the longitudinal line of the lower sphere. We will call that point the "departure point." Therefore, the preferred implementation first finds the angular position ($\theta_c$, $\phi_c$) of the departure point and then finds the azimuthal angle $\phi_c'$ in the primed coordinate system to which this angular position corresponds.

To solve for $\theta_c$, given a particular $\phi_c$, the preferred implementation recasts Eq. 90b into the form $$\frac{\cos\theta_c'}{\sqrt{\sin^2\theta_u \cos^2(\varphi_c - \varphi_u) + \cos^2\theta_u}} = \sin\alpha \sin\theta_c + \cos\alpha \cos\theta_c \quad (91)$$

where $$\sin\alpha = \frac{\sin\theta_u \cos(\varphi_c - \varphi_u)}{\sqrt{\sin^2\theta_u \cos^2(\varphi_c - \varphi_u) + \cos^2\theta_u}} \quad (92a)$$

and $$\cos\alpha = \frac{\cos\theta_u}{\sqrt{\sin^2\theta_u \cos^2(\varphi_c - \varphi_u) + \cos^2\theta_u}}. \quad (92b)$$

Applying our trigonometric identity to the right-hand side of Eq. 91, we obtain $$\cos(\theta_c - \alpha) = \frac{\cos\theta_c'}{\sqrt{\sin^2\theta_u \cos^2(\varphi_c - \varphi_u) + \cos^2\theta_u}} \quad (93)$$

which gives the solution $$\theta_c = \alpha + \cos^{-1}\left[\frac{\cos\theta_c'}{\sqrt{\sin^2\theta_u \cos^2(\varphi_c - \varphi_u) + \cos^2\theta_u}}\right]. \quad (94)$$

The arccosine generally has two distinct solutions: (1) the principal value which lies in the interval $[0, \pi]$ and which is denoted by capitalizing the function as $\text{Cos}^{-1}$ and (2) the negative of the principal value. We are interested in the case where these two solutions are degenerate. That can only be so if the arccosine and its negative are the same value, i.e., zero. Therefore $\theta_c = \alpha$ at the departure point, and the argument of the arccosine in Eq. 94 must be unity:

$$\frac{\cos\theta_c'}{\sqrt{\sin^2\theta_u \cos^2(\varphi_c - \varphi_u) + \cos^2\theta_u}} = 1. \quad (95)$$

This equation is the condition used in the preferred implementation to find the unprimed azimuthal position of the departure point. Squaring both sides gives $$\cos^2\theta_c' = \sin^2\theta_u \cos^2(\phi_c - \phi_u) + \cos^2\theta_u \quad (96)$$

which can be $\phi_c$ to yield $$\varphi_c = \varphi_u + \cos^{-1}\left[\sqrt{\frac{\cos^2\theta_c' - \cos^2\theta_u}{\sin^2\theta_u}}\right]. \quad (97)$$

The square root has a positive sign because the difference between $\phi_c$ and $\phi_u$ can be no greater in magnitude than $\pi/2$. Again, the arccosine has two solutions: the principal value $\text{Cos}^{-1}$ and its negative $-\text{Cos}^{-1}$. The current sphere would lose contact with the upper sphere if it is at azimuthal position $\phi_u \pm \text{Cos}^{-1}$. Its true position depends on where it was initially. If its initial position $\phi_{ci} > \phi_u$, then the principal value $\text{Cos}^{-1}$ is used. If its initial position is $\phi_{ci} < \phi_u$, then the negative of the principal value is used $-\text{Cos}^{-1}$. In the unlikely case that the initial position equals $\phi_u$, then the current sphere is balanced on the upper and lower sphere and a direction is randomly chosen by the random number generator. The preferred implementation using these relationships is to determine where contact is lost.

The preferred implementation also determines ($\theta_c$, $\phi_c$) of the departure point. It then finds the departure point in the primed coordinate system by use of the Euler transformation of Eqs. 72 and 76.

The first component of the primed vector is given by $$\sin\theta_c' \cos\phi_c' = -\cos\theta_u \sin\theta_c(\cos\phi_u \cos\phi c + \sin\phi_u \sin\phi_c) + \sin\theta_u \cos\theta_c \quad (98)$$

where the expression in parentheses can be written $\cos(\phi_c - \phi_u)$. Eq. 97 can substitute for $\cos(\phi_c - \phi_u)$. Also because $\theta_c$ is equal to $\alpha$ of Eqs. 92a and 92b, we have $$\sin\theta_c = \frac{\sqrt{\sin^2\theta_u - \sin^2\theta_c'}}{\cos\theta_c'} \quad (99a)$$

$$\cos\theta_c = \frac{\cos\theta_u}{\cos\theta_c'}. \quad (99b)$$

Substituting Eqs. 97 and 99a/99b into 98, we obtain for the end of the roll corridor due to departure $$\cos\varphi_{cf}' = \frac{\cos\theta_u \sin\theta_c'}{\sin\theta_u \cos\theta_c'} = \frac{\tan\theta_c'}{\tan\theta_u}. \quad (100)$$

The preferred implementation uses this relationship to obtain $\theta_c$ and $\phi_c$. Notice that the current sphere cannot be in stable contact with two pack spheres unless $\theta_c' < \theta_u$. Therefore $\phi cf$ always lies between 0 and $\pi/2$. Also, remember that $\cos \theta_c'$ is given by the left-hand side of Eq. 89 and that $\sin \theta c' = +[1 - \cos^2 \theta_c']^{1/2}$.

The second component of the primed vector is given by $$\sin \theta_c' \sin\phi_c' = (\sin \phi_u \cos \phi_c - \cos \phi_u \sin \phi_c)\sin \theta_c \quad (101)$$

and the same set of substitutions leads to $$\sin\varphi'_{cf} = \frac{\sqrt{\sin^2\theta_u - \sin^2\theta'_c}}{\cos\theta'_c \sin\theta_u}. \quad (102)$$

The $\phi_{cf}'$ defined by Eqs. 100 and 102 is the departure point and is the end of the roll corridor. At this position, the current sphere loses contact with the upper sphere (or both if their centers are the same altitude). These relationships also are used in the preferred implementation to determine $\theta_c$ and $\phi_c$.

Hitting the Cylinder Wall

The cylinder wall for the current sphere is located at global radius W. The preferred implementation can find whether the roll corridor of the current sphere on the two pack spheres is such that the current sphere's center can intersect the cylinder wall. If it does, then the $\phi_c'$ of intersection is found.

We need the global position of the current sphere as a function of $\phi_c'$. Again, the global position of the current sphere is $$\vec{R}_c = \vec{R}_i + \vec{r}_c \quad (103)$$

where $\vec{R}_i$ is the global position of one of the contact spheres and $\vec{r}_c$ is the current sphere's position in the unprimed local coordinate system. (Remember the unprimed coordinate system is centered in Sphere i and has axes parallel to the global axes.) The unprimed vector is given in terms of the primed vector (that contains $\phi_c'$) by the inverse Euler matrix equation $$\vec{r}_c = A^{-1} \cdot \vec{r}_c' \quad (104)$$

where $A^{-1}$ is the transpose of the Euler matrix in Eq. 72 and $r_c' = (x_c', y_c', z_c')$ is given by $$x_c' = (\alpha_c + \alpha_i)\sin \theta_c' \cos \phi_c' \quad (105a)$$

$$y_c' = (\alpha_c + \alpha_i)\sin \theta_c' \sin \phi_c' \quad (105b)$$

$$z_c' = (\alpha_c + \alpha_i)\cos \theta_c'. \quad (105c)$$

The preferred implementation therefore finds the global position $R_c = (X_c, Y_c, Z_c)$ in terms of the single variable $\phi_c'$ describing the descent down the roll corridor. If the lateral global position of the current sphere reaches the cylinder wall radius W for a value of $\phi_c'$ in the interval $(\phi_{ci}', \phi_{cf}')$, then the current sphere can reach the cylinder wall if it does not encounter another object first. In other words, if there is a solution of $$X_c^2 + Y_c^2 = W^2 \quad (106)$$

for $\phi_c'$ in the interval $(\phi_{ci}', \phi_{cf}')$, then the current sphere reaches the wall. Written explicitly, Eq. 106 has the form $$A_0 + A_1 \cos \phi_c' + A_2 \cos^2\phi_c' + B_1 \sin \phi_c' + B_2 \sin^2\phi_c' = 0 \quad (107)$$

where $$A_0 = (X_i^2 + Y_i^2 - W^2)/(\alpha_c + \alpha_i) + \sin \theta_{ji} \cos \theta_c'[2X_i \cos \phi_{ji} + 2Y_i \sin \phi_{ji} + (\alpha_c + \alpha_i)\sin \theta_{ji} \cos \theta_c'] \quad (108a)$$

$$A_1 = -2 \sin \theta_c' \cos \theta_{ji}[X_i \cos \phi_{ji} + Y_i \sin \phi_{ji} + (\alpha_c + \alpha_i)\sin \theta_{ji} \cos \theta_c'] \quad (108b)$$

$$A_2 = (\alpha_c + \alpha_i)\cos^2\theta_{ji} \sin^2\theta_c' \quad (108c)$$

$$B_1 = 2 \sin \theta_c'[X_i \sin \phi_{ji} - Y_i \cos \phi_{ji}] \quad (108d)$$

$$B_2 = (\alpha_c + \alpha_i)\sin^2\theta_c'. \quad (108e)$$

Eq. 107 can be converted into a quartic equation in $\sin \phi_c'$ by changing the $\cos^2\phi_c'$ term into $1 - \sin^2\phi_c'$ and the $\cos \phi_c'$ term into $+[1 - \sin^2\phi_c']^{1/2}$. (The plus sign is used only because $\phi_c'$ cannot exceed $\pm \pi/2$.) We then have $$(A_0 + A_2) + B_1 \sin \phi_c' + (B_2 - A_2)\sin^2\phi_c' = -A_1[1 - \sin^2\phi_c']^{1/2}. \quad (109)$$

Squaring both sides gives $$(A_2 - B_2)^2 \sin^4\phi_c' - 2B_1$$

$$(A_2 - B_2)\sin^3\phi_c' + (A_1^2 - 2$$

$$A_0 A_2 - 2A_2^2 + B_1^2 + 2A_0 B_2 + 2$$

$$A_2 B_2)\sin^2\phi_c' + 2(A_0 + A_2)B_1$$

$$\sin \phi_c' + (A_0 - A_1 + A_2)(A_0 + A_1 + A_2) = 0 \quad (110)$$

If this equation has any real roots in the interval $(\phi_{ci}', \phi_{cf}')$, then the smallest in magnitude of these that satisfies the original Eq. 107 is the point at which the roll corridor intersects the cylinder wall. The preferred implementation can check the roots in the original equation because squaring can give extraneous roots.

Hitting One or More Spheres Simultaneously

The preferred implementation has now defined a roll corridor in the primed coordinate system beginning at $\phi_{ci}'$ and ending at $\phi_{cf}'$. The end of the roll corridor is where the current sphere either lost contact with one or both of its contact spheres, when its south pole encountered either a catch net or a water level, or when its center encountered its cylinder wall. The preferred implementation can check all spheres that can intersect this roll corridor to find the sphere(s) encountered first as the current sphere descends along its roll corridor, i.e., as $\phi_{c'}$ moves from $\phi_{ci}'$ to $\phi_{cf}'$.

The global position of the current sphere as a function of $\phi_c'$ is given by Eqs. 80, 81, and 84. If some other pack spheres, say the k-th sphere is to intersect the roll corridor, then the following equation must have a solution in the range $(\phi_{ci}', \phi_{cf}')$:

$$|\vec{R}_c(\phi_c') - \vec{R}_k| = a_c + a_k. \quad (111)$$

Squaring this equation gives $$R_c^2 - 2\vec{R}_c \cdot \vec{R}_k + R_k^2 = (a_c + a_k)^2 \quad (112)$$

which becomes the following equation in $\phi_c'$:

$$A \cos \phi_c' + B \sin \phi_c' = C \quad (113)$$

where $$A = -X_{ik} \cos \phi_{ji} \cos \theta_c' -$$

$$Y_{ik} \cos \theta_{ji} \sin \phi_{ji} \sin \theta_c' + Z_{ik} \sin$$

$$\theta_c' \sin \theta_{ji} \quad (114)$$

$$B = X_{ik} \sin \phi_{ji} \sin \theta_c' - Y_{ik} \cos \phi$$

$$_{ji}\sin\theta_c' \quad (115)$$

$$C = -X_{ik}\cos\varphi_{ji}\cos\theta_c'\sin\theta_{ji} - Y_{ik}\cos\theta_c'\sin\varphi_{ji}\sin\theta_{ji} - \quad (116)$$
$$Z_{ik}\cos\theta_c'\cos\theta_{ji} + \frac{(2a_c + a_i + a_k)(a_k - a_i) - R_{ik}^2}{2(a_c + a_i)}.$$

The global coordinates of Sphere k relative to Sphere i are given by $$X_{ik}=X_i-X_k, \ Y_{ik}=Y_i-Y_k, \ Z_{ik}=Z_i-Z_k, \quad (117a)$$

and the square of the distance between the two sphere centers is $$R_{ik}^2 = X_{ik}^2 + Y_{ik}^2 + Z_{ik}^2. \quad (117b)$$

The solution procedure of Eq. 113 is similar to that given in Section VII.D.7. The preferred implementation finds $\phi_c'$ to be $$\varphi_c' = a \pm \cos^{-1}\frac{C}{\sqrt{A^2 + B^2}} \quad (118a)$$

where $$a = \tan^{-1}\frac{B}{A} \quad (118b)$$

If any of the $\phi_c'$ solutions are outside the range [0, 2π], units of 2π are added or subtracted until they are inside that range. Then if any solutions lie within $(\phi_{ci}', \phi_{cf}')$ the smallest in magnitude of these is the position of first contact between the current sphere and Sphere k. If there is no solution, then Sphere k intersects no part of the roll corridor.

The preferred implementation has now performed an exact solution to find whether and where Sphere k intersects the current sphere's roll corridor. In most packs, the vast majority of the pack spheres are out of range of the roll corridor and so do not need the detailed calculations of Eqs. 118a and 118b. There are a few much simpler checks that can be performed by the preferred implementation to immediately determine whether a pack sphere is out of range and so is not a contact candidate.

First, the roll corridor's highest global altitude is at $\phi_{ci}'$ which, from Eq. 81 is found to be $$Z_{c,max}=Z_i+(\alpha_c+\alpha_i)(\sin\theta_{ji}\sin\theta_c'\cos\phi_{ci}'+\cos\theta_{ji}\cos\theta_c'). \quad (119)$$

Therefore, the k-th pack sphere whose center lies a distance $\alpha_c+\alpha k$ above $Z_{c,max}$ cannot overlap the roll corridor. Likewise, the lowest global altitude is at $\phi_{cf}'$ and is given by $$Z_{c,min}=Z_i+(\alpha_c+\alpha_i)(\sin\theta_{ji}\sin\theta_c'\cos\phi_{cf}'+\cos\theta_{ji}\cos\theta_c'). \quad (120)$$

The k-th pack sphere whose center lies a distance $\alpha_c+\alpha k$ below $Z_{c,min}$ also cannot overlap the roll corridor. Therefore, the preferred implementation can immediately exclude from consideration all spheres whose global altitudes $Z_k$ satisfy the following:

k-th sphere does not overlap if $$Z_k \geq Z_{c,max} + \alpha_c + \alpha_k \quad (121a)$$

or $$Z_k \leq Z_{c,min} - \alpha_c - \alpha_k. \quad (121b)$$

Roll corridor extrema in the X and Y directions do not necessarily lie at the beginning and end of the roll corridor. Eqs. 84a and 84b give the global X and Y coordinates of the current sphere as a function of $\phi_c'$. If we differentiate $X_c(\phi_c')$ with respect to $\phi_c'$ and set the derivative equal to zero, we have an equation whose solution gives us the extrema in X. If either of those extrema lie in $(\phi_{ci}', \phi_{cf}')$ then that position is either the minimum or maximum X value the current sphere assumes as it descends the roll corridor. The same is true for the derivative of $Y(\phi_c')$ with respect to $\phi_c'$. The derivatives followed by the extrema solutions are $$\frac{dX_c}{d\varphi_c'} = (a_c + a_i)(\cos\theta_{ji}\cos\varphi_{ji}\sin\theta_c'\sin\varphi_c' + \sin\varphi_{ji}\sin\theta_c'\cos\varphi_c') = 0 \quad (122)$$

$$\tan\varphi_{cx}' = -\frac{\tan\varphi_{ji}}{\cos\theta_{ji}} \quad (123)$$

for the two X extrema (the above equation has two solutions for $\phi_{cx}'$), and $$\frac{dY_c}{d\varphi_c'} = (a_c + a_i)(\cos\theta_{ji}\sin\varphi_{ji}\sin\theta_c'\sin\varphi_c' - \cos\varphi_{ji}\sin\theta_c'\cos\varphi_c') = 0 \quad (124)$$

$$\tan\varphi_{cy}' = -\frac{\cot\varphi_{ji}}{\cos\theta_{ji}} \quad (125)$$

for the two Y extrema.

Finally then, the X and Y extrema of the roll corridor in the global coordinates are $$X_{c,min}=\text{MIN}[X_c(\phi_{ci}'), X_c(\phi_{cf}'), X_c(\phi_{cx}')] \quad (126a)$$

$$X_{c,max}=\text{MAX}[X_c(\phi_{ci}'), X_c(\phi_{cf}'), X_c(\phi_{cx}')] \quad (126b)$$

with the $X_c(\phi_{cx}')$ omitted if neither $\phi_{cx}'$ lies in $(\phi_{ci}', \phi_{cf}')$. Similarly, $$Y_{c,min}=\text{MIN}[Y_c(\phi_{ci}'), Y_c(\phi_{cf}'), Y_c(\phi_{cy}')] \quad (127a)$$

$$Y_{c,max}=\text{MAX}[Y_c(\phi_{ci}'), Y_c(\phi_{cf}'), Y_c(\phi_{cy}')], \quad (127b)$$

again with the $Y_c(\phi_{cy}')$ omitted if neither $\phi_{cy}'$ lies in $(\phi_{ci}', \phi_{cf}')$.

Then the k-th sphere cannot overlap the roll corridor if $$X_k \leq X_{c,min} - \alpha_c - \alpha_k \quad (128a)$$

or $$X_k \geq X_{c,max} + \alpha_c + \alpha_k \quad (128b)$$

or $$Y_k \leq Y_{c,min} - \alpha_c\ \alpha_k \quad (128c)$$

or $$Y_k \geq Y_{c,max} + a_c + \alpha_k. \quad (128d)$$

Another discriminator that can be used by the preferred implementation to immediately exclude a large number of pack spheres from detailed examination is to consider whether the roll corridor is far enough from the central Z axis that it cannot overlap all the spheres within a given inner cylinder. To find this, the preferred implementation uses the closest radial approach $P_{c,min}$ of the roll corridor to the central axis. The square of the radial distance $[P_c(\phi_c')]^2$ is given by $$[P_c(\phi_c')]^2 = [X_c(\phi_c')]^2 + [Y_c(\phi_c')]^2 \quad (129)$$

where we obtain the explicit expression by substituting Eqs. 84a and 84b into Eq. 129:

$$P_c(\phi_c')]^2 = [X_i + (\alpha_c + \alpha_i)(-\cos\theta_{ji}\cos\phi_{ji}\sin\theta_c'\cos\phi_c' + \sin\phi_{ji}\sin\theta_c'\sin\phi_c' + \sin\theta_{ji}\cos\phi_{ji}\cos\phi_c')]^2$$
$$+ [Y_i + (a_c + a_i)(-\cos\theta_{ji}\sin\phi_{ji}\sin\theta_c'\cos\phi_c' - \cos\phi_{ji}\sin\theta_c'\sin\phi_c' + \sin\theta_{ji}\sin\phi_{ji}\cos\theta_c')]^2. \quad (130)$$

Setting the derivative of $[P_c(\phi_c')]^2$ with respect to $\phi_c'$ equal to zero yields the equation whose solution $\phi_{cp}'$ gives the closest approach of the roll corridor to the global Z axis:

$$[X_i + (\alpha_c + a_i)(-\cos\theta_{ji}\cos\phi_{ji}\sin\theta c'\cos\phi_c' + \sin\phi_{ji}\sin\theta_c'\sin\phi_c' + \sin\theta_{ji}\cos\phi_{ji}\cos\theta_c')](\cos\theta_{ji}\cos\phi_{ji}\sin\theta_c'\sin\phi_c' + \sin\phi_{ji}\sin\theta_c'\cos\phi_c') + [Y_i + (\alpha_c + a_i)(-\cos\theta_{ji}\sin\phi_{ji}\sin\theta_c'\cos\phi_c' - \cos\phi_{ji}\sin\theta c'\sin\phi_c' + \sin\theta_{ji}\sin\phi_{ji}\cos\theta_c')](\cos\theta_{ji}\sin\phi_{ji}\sin\theta c'\sin\phi_c' - \cos\phi_{ji}\sin\theta_c'\cos\phi_c') = 0. \quad (131)$$

This equation is of the form $$A_0 + A_1\cos\phi_c' + A_2\cos^2\phi_c' + B_1\sin\phi_c' + B_2\sin^2\phi_c' = 0 \quad (132)$$

where in this case, the coefficients are given by $$A_0 = X_i^2 + Y_i^2 + 2(a_c + a_i)\cos\theta_c'(X_i\sin\theta_{ji}\cos\phi_{ji} + Y_i\sin\theta_{ji}\sin\phi_{ji}) + (a_c + a_i)^2\cos^2\theta_c'\sin^2\theta_{ji} \quad (133a)$$

$$A_1 = -2(a_c + a_i)\cos\theta_{ji}\sin\theta_c'[X_i\cos\phi_{ji} + Y_i\sin\phi_{ji} + (a_c + a_i)\cos\theta_c'\sin\theta_{ji}] \quad (133b)$$

$$A_2 = (a_c + a_i)^2\cos^2\theta_{ji}\sin^2\theta_c' \quad (133c)$$

$$B_1 = 2(a_c + a_i)\sin\theta_c'\{\sin\theta_{ji}[X_i + (a_c + a_i)\cos\theta_c'\sin\theta_{ji}\cos\phi_{ji}] - \cos\theta_{ji}[Y_i + (a_c + a_i)\cos\theta_c'\sin\theta_{ji}\sin\phi_{ji}]\} \quad (133d)$$

$$B_2 = (a_c + a_i)^2\sin^2\theta_c' \quad (133e)$$

Eq. 132 can be converted into a quartic equation by changing the cosines into sines in the same fashion as led up to Eq. 110:

$$(A_2 - B_2)^2\sin^4\phi_c' - 2B_1(A_2 - B_2)\sin^3\phi_c' + (A_1^2 - 2A_0A_2 - 2A_2^2 +$$
$$B_1^2 + 2A_0B_2 + 2A_2B_2)\sin^2\phi_c' + 2$$
$$(A_0 + A_2)B_1\sin\phi_c' + (A_0 - A_1 + A_2)$$
$$(A_0 + A_1 + A_2) = 0 \quad (134)$$

There are four $\sin\phi_c'$ solutions to this quartic equation and for a given $\sin\phi_c'$ there are two $\phi_c'$ solutions. Complex solutions and real solutions lying outside $[1, 1]$ are immediately discarded in the preferred implementation. Furthermore, we are only interested in those solutions with the same sign as $\sin\phi_{ci}'$ and that lie in $(\phi_{ci}', \phi_{cf}')$ because that is the direction the current sphere will roll. The preferred implementation checks any remaining solution $\phi_{cp}'$ by ensuring it satisfies the original Eq. 132. If there is no solution in $(\phi_{ci}', \phi_{cf}')$ then one or the other of the end points is the closest approach to the global Z axis and both must be substituted into Eq. 130 to find the smaller $P_c$.

Once the $P_{c,min}$ of closest approach is found, the preferred implementation checks to see if there are any mode's cylinder radii $W_k$ that lie completely inside $P_{c,min}$ by more than the sum of the mode sphere's radius plus the current sphere's radius. If $$P_c \geq W_k + a_1 + a_c \quad (135)$$

then none of the Mode k particles can touch the current sphere as it descends its current roll corridor and so may immediately be excluded as candidates for contact.

All spheres whose north poles have sunk beneath the catch net or water level are not candidates for contact with the current sphere. The preferred implementation continually or periodically monitors the lowest index number of the sphere whose north pole is still above the catch net so that no time is wasted looking at spheres with lower index numbers as candidates for contact.

Touching One Sphere and the Cylinder Wall

Remember that in the preferred implementation it is the center of the current sphere constrained by the cylinder wall, not its edge. When in stable contact with both a pack sphere and the cylinder wall, the roll corridor lies on the wall and descends toward the equatorial plane of the contacted pack sphere. If the contacted sphere (denote it Sphere i) is as large as the cylinder, then the current sphere moves toward the lowest point on a roll corridor that spans the entire $2\pi$ radians of the cylinder.

The roll corridor will be denoted by the global azimuthal position $\Phi_c$. Its initial position is given by $$\Phi_{c0} = \tan^{-1}(Y_c/X_c). \quad (136)$$

The preferred implementation uses the range $[0, 2\pi]$ rather than $[-\pi, \pi]$ for the range of the global azimuthal position. The global azimuthal position of the Sphere i is $$\Phi_i = \tan^{-1}(Y_i/X_i) \quad (137)$$

which also lies in $[0, 2\pi]$. If $\Phi_{c0} > \Phi_i$ the current sphere rolls toward higher $\Phi$. If $\Phi_{c0} < \Phi_i$, it rolls toward lower $\Phi$. In the unlikely event that $\Phi_{c0} = \Phi_i$, the random number generator chooses a roll direction.

If it encounters nothing else, the current sphere will roll until it reaches:
1. the equatorial plane of Sphere i where it will fall away from Sphere i; or
2. the lowest azimuthal point in its cylinder permitted by Sphere i.

The azimuthal position at which it will reach the equatorial plane of Sphere i is found by the law of cosines as $$\Phi_{cf} = \Phi_i \pm \Delta\Phi_c \quad (138)$$

where $$\Delta\Phi_c = \cos^{-1}\left(\frac{W_c^2 + P_i^2 - (a_c + a_i)^2}{2W_c P_i}\right). \quad (139)$$

In this expression, $W_c$ is the radius of the cylinder wall, $P_i = \sqrt{X_i^2 + Y_i^2}$ is the radial position of Sphere i from the global Z axis, and $\alpha_c$ and $\alpha_i$ are the radii of the current sphere and Sphere i, respectively. The plus sign is used in Eq. 138 if the current sphere is rolling toward increasing $\Phi$, the minus sign is used if the current sphere is rolling toward decreasing $\Phi$. If the absolute value of the quantity in the parentheses of Eq. 139 is greater than unity, then there is no solution and the current sphere simply rolls around the perimeter of the cylinder until it reaches the lowest point it can. This lowest point is opposite the azimuthal position of Sphere i. Hence, if $$\left|\frac{W_c^2 + P_i^2 - (a_c + a_i)^2}{2W_c P_i}\right| > 1 \quad (140)$$

then $$\Delta\Phi_c = \pm\pi. \quad (141)$$

In the unlikely event that $P_i = 0$, i.e., Sphere i is centered on the global Z axis, then there is no downward direction. The roll corridor is horizontal and the current sphere is placed where it is.

In this analysis, if the addition or subtraction of $\Delta\Phi_c$ causes $\Phi_{cf}$ to lie outside $[0, 2\pi]$, then units of $2\pi$ are added or subtracted until $\Phi_{cf}$ again lies in $[0, 2\pi]$.

The preferred implementation also determines what placed pack spheres might intersect the roll corridor in the range $(\Phi_{c0}, \Phi_{cf})$.

The current sphere will impact a placed pack sphere, say the j-th sphere, if there is a solution to $$|\vec{R}_c(\Phi_c) - \vec{R}_j| = a_c + a_j \quad (142)$$

anywhere in the range $(\Phi_{c0}, \Phi_{cf})$. The Cartesian components of the vector $\vec{R}_c(\Phi_c) = X_c, Y_c, Z_c$ are given by $$X_c(\Phi_c) = W_c \cos\Phi_c \quad (143)$$

$$Y_c(\Phi_c) = W_c \sin\Phi_c \quad (144)$$

The $Z_c$ component can be found by inserting the $X_c$ and $Y_c$ component into the condition $$|\vec{R} - \vec{R}_j| = a_c + a_i. \quad (145)$$

Squaring both sides, we obtain $$W_c^2 + Z_c^2 + R_i^2 - 2W_c(X_i \cos\Phi_c + Y_i \sin\Phi_c) - 2Z_i Z_c = (a_c + a_i)^2 \quad (146)$$

which is quadratic in $Z_c$. One of the solutions is when the current sphere is above Sphere i and the other when it is below. In the preferred implementation, we are only interested in the solution above Sphere i, which is $$Z_c(\Phi_c) = Z_i + [Z_i^2 + (\alpha_c + \alpha_i)^2 - W_c^2 - R_i^2 + 2W_c(X_i \cos\Phi + Y_i \sin\Phi_c)]^{1/2} \quad (147)$$

Now, inserting Eqs. 143, 144, 147 in Eq. 142, we obtain an equation to solve for the $\Phi_c$ at which the current sphere contacts the j-th pack sphere:

$$A_0 + A_1 \cos\Phi_c + B_1 \sin\Phi_c + (A_2 \cos\Phi_c + B_2 \sin\Phi_c)^2 = 0 \quad (148)$$

where the coefficients are given by $$A_0 = G^2 - 4(Z_i - Z_j)^2[Z_i^2 - W_c^2 - R_i^2 + (a_c + a_i)^2] \quad (149a)$$

$$A_1 = 4G\, W_c(X_i - X_j) - 8(Z_i - Z_j)^2 W_c X_i \quad (149b)$$

$$A_2 = 2W_c(X_i - X_j) \quad (149c)$$

$$B_1 = 4GW_c(Y_i - Y_j) - 8(Z_i - Z_j)^2 W_c Y_i \quad (149d)$$

$$B_2 = 2W_c(Y_i - Y_j) \quad (149e)$$

and G is given by $$G = (a_i - a_j)(2a_c + a_i + a_j) - R_i^2 + R_j^2 + 2Z_i^2 - 2Z_i Z_j. \quad (150)$$

Eq. 148 can be converted into a quartic polynomial in $\cos\Phi_c$:

$$(A_2^2 + B_2^2)^2 \cos^4\Phi_c + 2$$
$$(A_1 A_2^2 + 2A_2 B_1 B_2 - A_1 B_2^2)$$
$$\cos^3\Phi_c + (A_1^2 + 2A_0 A_2^2 + B_1^2$$
$$-2A_0 B_2^2 - 2A_2^2 B_2^2 - 2B_2^4)$$
$$\cos^2\Phi_c + 2(A_0 A_1 - 2A_2 B_1 B_2 + A_1$$
$$B_2^2)\cos\Phi_c + (A_0 - B_1 + B_2^2)(A_0 + B_1 + B_2^2) = 0 \quad (151)$$

whose solutions are candidates for contact of the j-th pack sphere. The preferred implementation uses this expression as part of its determination. There are four solutions of the quartic equation and each $\cos\Phi_c$ solution has two $\Phi_c$ solutions—eight in all. Of the four quartic solutions, the preferred implementation can eliminate complex solutions or solutions whose magnitude is greater than unity. Of the remaining solutions, if there are any that satisfy the original Eq. 148 and that lie in the range of the roll corridor ($\Phi_{c0}$, $\Phi_{cf}$), they are contact points. Of the contact point(s), the value of $\Phi_c$ that lies closest to $\Phi_{c0}$ is the point at which the current sphere touches the j-th sphere. $W_c$ will denote that point by $\Phi_{cj}$. If there are no solutions that satisfy the above conditions, the current sphere cannot contact the j-th sphere.

As the preferred implementation checks the candidate spheres in the pack for contact with the current sphere, that sphere with $\Phi_{cj}$ closest to $\Phi_{c0}$, if any, is the next sphere contacted. In the unlikely case that two or more pack spheres have the same $\Phi_{cj}$, then it checks the stability of each trio of contacts to see if the current sphere is to be placed there. If it is not stable, then the stability routine determines which sphere(s) the current sphere will roll away from.

As an efficiency measure, the preferred implementation can eliminate from consideration any modes or categories that are sufficiently far inside the cylinder wall of the current sphere that they cannot touch it. All mode k spheres are out of range if $$W_k + a_k \leq W_c - a_c. \quad (152)$$

Any other sphere j is a candidate for being in range only if $$W_c - a_c - a_j < P_j < W_c + a_c + a_j \quad (153)$$

where $P_j$ is the global radial distance of Sphere j from the Z axis.

THE SUBROUTINE UPDATE

The UPDATE subroutine of the preferred implementation updates all parameters and arrays that change as a result of the placement of the current particle. These changes include the following.

1. The Pool Switch

If the pool switch is true, then the placement of the current particle means the bin from which it was chosen should be diminished by one. This adjustment is performed in Subroutine UPDATE.

The Catch Net

The catch net belonging to the mode, submode or category current sphere also generally ratchets upward. The prescription for determining how much it ascends will now be addressed.

A sense of pack surface must be established. With a variety of particles being dropped into a variety of cylinders, the pack surface must be defined. This can be done in a number of ways, as noted above. For purposes of the preferred implementation, let us consider the altitude of the south poles of the last m placed spheres of any and all modes. As explained above, the average of those altitudes is defined for present purposes as the pack "surface":

$$Z_{surface} = \frac{1}{m}\sum_{j=1}^{m}(Z_j - a_j) \quad (154)$$

where m is the number of most recently placed pack sphere equatorial cross-sections that would just cover the outermost cylinder n with cross-sectional area $\pi W_n^2$. The value for m is found from the inequality $$\sum_{j=1}^{m-1} a_j^2 < W_n^2 \leq \sum_{j=1}^{m} a_j^2. \quad (155)$$

If the size of the last placed set of spheres is very large so that m is very small, then we have a minimum required value for m which can be user-defined but for which the default value in this implementation is $m_{min}=12$. Only when the pack is just starting so that 12 particles have not yet been dropped is m smaller for this implementation. Preplaced particles do not count in assessing the pack "surface."

The k-th mode catch net is then defined as $$Z_{net}(k) = Z_{surface} - \gamma a_k \quad (156)$$

where $\gamma$ is the number of k-th mode radii beneath the surface that the k-th mode catch net lies. Here it is a user-defined number which has a default of $\gamma=2$.

Subroutine UPDATE readjusts all the above parameters so that the catch net for every mode has a proper value after the current sphere is placed.

When the pack is still small enough that an insufficient number of particles have been placed to satisfactorily define a surface, the catch net may be ratcheted up a little after the placement of each particle so that the particles on the bottom of the cylinders do not all have the same altitude. If the switch ROUGHNET is true, then the current sphere's catch net moves upward by a small random amount $$ra_{min}/N_{cs} \quad (157)$$

where r is a uniformly generated random number in [0, 1] and $N_{cs}$ is the total number of sphere cross-sections required to cover all the cylinders:

$$N_{cs} = \sum_{k=1}^{n} \frac{W_k^2 - W_{k-1}^2}{a_k^2} \quad (158)$$

where n is the number of modes, $W_k$ is the cylinder wall of the k-th mode, and $W_0 \equiv 0$. If ROUGHNET is false, then the catch net stays where it is until enough particles have been defined to make a surface and until the surface is more than $Z_{surface} - \gamma a_k$ above the starting place.

The starting place for the k-th mode catch net is $Z_{init} - a_k$. A k-th sphere radius is subtracted from the overall pack starting altitude $Z_{init}$ because the catch net stops south poles and $Z_{init}$ is the starting place for sphere centers. The default for $Z_{init}$ is zero in this implementation.

The Water Levels

The water level also is modified when the current sphere is placed according to the preferred implementation. Recall that the water level only exists beyond the innermost cylinder. Its altitude tracks the pack surface and is at a user-specified distance $\beta$ in terms of the smallest sphere radius $a_{min}$ beneath the surface defined by Eqs. 154 and 155. The default for $\beta$ is unity. Hence $$Z_w = Z_{surface} - \beta a_{min}. \quad (159)$$

If $\beta$ is negative, the water level lies above the pack surface.

The smallest cylinder in this implementation has no water level, only a catch net. It does not need a water level because water levels are designed to simulate the surface of the innermost cylinder and the innermost cylinder has its own particle surface potentially containing all the particles of the pack.

Current Sphere History Parameters

The preferred implementation uses are parameters that monitor the number of times the current sphere tunneled, the number of distinct roll corridors it underwent (not counting free-fall drops), and the number of free-fall drops it underwent. All these are reset to zero in this implementation.

The arrays indicating which pack spheres the current sphere is touching and which spheres it just rolled away from are also zeroed out along with the total number of such spheres.

The array keeping track of the lowest index number above catch net for each mode is adjusted if necessary.

The array monitoring the index numbers of all pack spheres with exposed north poles also is updated if the current sphere covered one or more exposed north poles.

In addition, the pack sphere position arrays have the current sphere's (X, Y, Z) position added to them along with the array specifying its mode number. The counter monitoring the total number of spheres placed so far in the pack is also incremented by one.

THE SUBROUTINE OUTSTAT

There are a number of important pack statistics and features that the user may need or want to calculate. In this implementation, subroutine OUTSTAT calculates the output statistics that the user specifies. These output statistics include:

A. The volume fraction of the pack.

B. The radial distribution functions $g_{ij}(r)dr$ which is the mean number of Mode j particle centers that lie between r and r+dr from a Mode i particle center.

C. Coordination numbers $\Omega_{ij}$ which represent the mean number of Mode j particles touching a Mode i particle.

D. Detailed pack statistics for each particle mode such as that mode's minimum and maximum positions, number of its particles in the pack, radial and axial density functions for each requested mode, as well as other information. Each of these output data will now be addressed.

Finding the Volume Fraction

To determine the packing fraction, the program finds the total volume of the innermost cylinder occupied by spheres. Recall that the cylinder walls are boundaries to the centers of the spheres, not their edges. Hence, many spheres will be overlapping the cylinder walls. The preferred implementation has a general expression for determining how much volume of a sphere of radius $a_s$ located at position $(x_s, y_s, z_s)$ lies inside a cylinder which is concentric to the z axis with radius $a_c$, bottom cylinder altitude $z_b$, and top cylinder altitude $z_t$. The sphere volume inside the cylinder will be denoted $V_{in}$. Here the sphere and cylinder geometric parameters have no restrictions except:

$$a_s > 0,\ a_c > 0,\ \text{and}\ z_t > z_b. \tag{160}$$

The radial distance of the sphere center from the z axis is defined here by $$\rho_s = [x_s^2 + y_s^2]^{1/2}. \tag{161}$$

There are four possible cases for this overlap problem. In Case 1, the sphere is completely outside the cylinder so $V_{in} = 0$. In Case 2, the sphere is completely inside the cylinder so $V_{in} = (4/3)\pi a_s^3$. In Case 3, the cylinder is completely inside the sphere so $V_{in} = \pi a_c^2(z_t - z_b)$. In Case 4, the sphere and cylinder intersect each other and the expression for $V_{in}$ is more complex. In the preferred implementation, processing is performed to identify and address these cases using the following approach.

Case 1: Sphere Completely Outside Cylinder

The sphere is completely outside the cylinder $$V_{in} = 0 \tag{162}$$

only if one of the following conditions are met:

If the sphere's north pole is lower than the cylinder bottom . . .

$$z_s + a_s \leq z_b \tag{163a}$$

or if the sphere's south pole is above the cylinder top . . .

$$z_s - a_s \geq z_t \tag{163b}$$

or if the sphere is more than its radius away from the cylinder side . . .

$$\rho_s - a_s \geq a_c \tag{163c}$$

or if the sphere center is above the cylinder top and is more than its radius away from the upper cylinder edge . . .

$$(\rho_s - a_c)^2 + (z_s - z_t)^2 \geq a_s^2\ \text{and}\ z_s > z_t \tag{163d}$$

or if the sphere center is below the cylinder bottom and is more than its radius away from the lower cylinder edge . . .

$$(\rho_s - a_c)^2 + (z_b - z_s)^2 \geq a_s^2\ \text{and}\ z_s < z_b. \tag{163e}$$

Case 2: Sphere Completely Inside Cylinder

The sphere is completely inside the cylinder $$V_{in} = (4/3)\pi a_s^3 \tag{164}$$

only if all three of the following conditions are simultaneously met:

If the sphere's north pole is no higher than the cylinder top . . .

$$z_s + a_s \leq z_t \tag{165a}$$

And if the sphere's south pole is no lower than the cylinder bottom . . .

$$z_s - a_s \geq z_b \tag{165b}$$

and if the sphere's equator nowhere exceeds the cylinder radius . . .

$$\rho_s + a_s \leq a_c. \tag{165c}$$

Case 3: Cylinder Completely Inside Sphere

The cylinder is completely inside the sphere $$V_{in} = \pi a_c^2(z_t - z_b) \tag{166}$$

if both the following two conditions are met:

If the upper edge of the cylinder is inside the sphere . . .

$$(\rho_s + a_c)^2 + (z_t - z_s)^2 \leq a_s^2 \tag{167a}$$

and if the lower edge of the cylinder is inside the sphere . . .

$$(\rho_s + a_c)^2 + (z_s - z_b)^2 \leq a_s^2. \tag{167b}$$

Case 4: Cylinder and Sphere Intersect

There are several subsets of Case 4. To efficiently organize them, we define two circles: the sphere circle and the cylinder circle. The sphere circle is the perimeter of the sphere's cross-section at a given z altitude. Its radius is $$r_s = [a_s^2 - (z - z_s)^2]^{1/2},\ z_s - a_s \leq z \leq z_s + a_s \tag{168}$$

and its radial position $\rho_s$ is given by Eq. 161. Likewise, the cylinder circle is the perimeter of the cylinder's cross-section which has constant radius $\alpha_c$ at any z altitude between $z_b$ and $z_t$ and is centered on the z axis.

To describe the intersection of sphere and cylinder, four subcases for the relationship of the sphere circle and the cylinder circle at a particular altitude z are defined:

Subcase 4.1: The two circles do not overlap or one or both are nonexistent.

Subcase 4.2: The sphere circle is completely enclosed in the cylinder circle.

Subcase 4.3: The cylinder circle is completely enclosed in the sphere circle.

Subcase 4.4: The two circles intersect.

To find $V_{in}$, the preferred implementation integrates in z the overlap areas of the two circles $A_{in}$ from the altitude where one subcase holds to the altitude where another subcase holds.

For Subcase 4.1, $A_{in} = 0$. (169a)

For Subcase 4.2, $A_{in} = \pi \alpha_s^2$. (169b)

For Subcase 4.3, $A_{in} = \pi \alpha_c^2$. (169c)

For Subcase 4.4, $A_{in} = \alpha_c^2(\alpha - \cos\alpha \sin\alpha) + r_s^2(\beta - \cos\beta \sin\beta)$ (169d)

where $r_s$ is given by Eq. 168 and $$\cos\alpha = \frac{\rho_s^2 + a_c^2 - r_s^2}{2\rho_s a_c} \tag{170a}$$

$$\sin\alpha = \frac{\sqrt{[r_s^2 - (a_c - \rho_s)^2][(a_c + \rho_s)^2 - r_s^2]}}{2\rho_s a_c} \tag{170b}$$

$$\cos\beta = \frac{\rho_s^2 + r_s^2 - a_c^2}{2\rho_s r_s} \tag{171a}$$

$$\sin\beta = \frac{\sqrt{[r_s^2 - (a_c - \rho_s)^2][(a_c + \rho_s)^2 - r_s^2]}}{2\rho_s r_s}. \tag{171b}$$

The implementation now constructs a series of altitudes at which the cylinder circle and the sphere circle change from one subcase to another in Case 4.

A sphere and a cylinder side can intersect each other at either 0, 2, or 4 altitudes. Pairs of altitudes may be degenerate (two solutions having the same altitude) if the sphere just nicks the cylinder wall. The preferred implementation determines these altitudes using the following equation:

$$[r_s(z)]^2 = [a_c \pm \rho_s]^2 \tag{172a}$$

or $$a_s^2 - (z - z_s)^2 = [a_c \pm \rho_s]^2 \tag{172b}$$

which, using Eq. 176, has the four solutions $$z = z_s \pm \sqrt{a_s^2 - (a_c \pm \rho_s)^2}. \tag{173}$$

The + sign in the first ± of Eq. 173 denotes the upper or northern hemisphere intersection altitude; the − sign denotes the lower or southern hemisphere intersection altitude. The + sign in the second ± of Eq. 173 denotes intersection with the far cylinder wall, on the opposite side of the z axis from the sphere's side; the − sign denotes intersection with the near cylinder wall, on the same side of the z axis as the sphere.

Armed with these four solutions, the implementation can effectively address each of the four subcases of Case 4. In this illustrative implementation, it separately addresses whether the sphere circle lies in the southern hemisphere of the sphere or whether it is in the equatorial plane or in the northern hemisphere. The four subcases are considered separately for the two hemispheres making eight situations in all. The hemispheres are considered separately because if the sphere circle is in the southern hemisphere, it is increasing in size as z increases. Hence the altitude at which we will change subcases can be determined. If the sphere circle is the equatorial plane or in the northern hemisphere, it is decreasing in size as z increases and again the altitude at which subcases will change can be determined.

Finding Upper and Lower Boundaries of Subcases for Case 4

The logic used in the preferred implementation to find the altitudes at which subcases change will now be described. Let $z_{low}$ be the lower altitude of the subcase currently being examined and $z_{high}$ be its upper altitude. The function $r_s(z)$ is given in Eq. 168.

Initially, let $z_{low} = z_b$, the bottom of the cylinder. After each DO WHILE cycle, $z_{low}$ is set to the previous cycle's $z_{high}$ and a new $z_{high}$ is sought. To illustrate using pseudocode expression:

```
V_in = 0                    ! Initialize V_in to zero.
z_low = z_b                 ! Initialize z_low to the bottom of the cylinder.
keepGoing = TRUE            ! Do Loop flag.
DO WHILE (keepGoing)
    IF (z_s > z_low) THEN                       ! Southern hemisphere subcases
        IF (ρ_s − r_s(z_low) > a_c) THEN        ! Subcase 4.1
```

$$z_{high} = z_s - \sqrt{a_s^2 - (a_c - \rho_c)^2}$$

```
        IF (z_high ≥ z_t) keepGoing = FALSE
            (There is no addition to V_in in this subcase.)
        ELSE IF (ρ_s + r_s(z_low) < a_c) THEN    ! Subcase 4.2
```

$$z_{high} = \mathrm{MIN}\left[z_s - \sqrt{a_s^2 - (a_c - \rho_s)^2},\ z_t,\ z_s + a_s\right]$$

$$V_{in} = V_{in} + \pi(z_{high} - z_{low})[a_s^2 - z_s^2 + z_s(z_{high} + z_{low}) - (z_{high}^2 + z_{high} z_{low} + z_{low}^2 / 3]$$

```
        IF (z_high = z_t OR z_high = z_s + a_s) keepGoing = FALSE
        ELSE IF (r_s(z_low) − ρ_s ≥ a_c) THEN    ! Subcase 4.3
```

$$z_{high} = \mathrm{MIN}\left[z_s + \sqrt{a_s^2 - (a_c + \rho_s)^2},\ z_t\right]$$

$$V_{in} = V_{in} + \pi a_c^2 (z_{high} - z_{low})$$

```
        IF (z_high = z_t) keepGoing = FALSE
        ELSE IF ((r_s(z_low) > ρ_s AND r_s(z_low) − ρ_s < a_c AND a_c ≤ r_s(z_low) + ρ_s)
              OR (ρ_s ≥ r_s(z_low) AND ρ_s − r_s(z_low) ≤ a_c AND a_c ≤ ρ_s + r_s(z_low)))
        THEN                                    ! Subcase 4.4
            IF (a_s > a_c + ρ_s) THEN
```

-continued $$z_{high} = MIN\left[z_s - \sqrt{a_s^2 - (a_c + \rho_s)^2}, z_t\right]$$

$$V_{in} = V_{in} + \int_{z_{low}}^{z_{high}} dz A_{in} = V_{in} + \Delta V_1 \quad (174)$$

where $\Delta V_1$ is given in the next section below.
    IF ($z_{high} = z_t$) keepGoing = FALSE
ELSE $$z_{high} = MIN\left[z_s + \sqrt{a_s^2 - (a_c - \rho_s)^2}, z_t\right]$$

$$V_{in} = V_{in} + \int_{z_{low}}^{z_{high}} dz\, A_{in} = V_{in} + \Delta V_2 \quad (175)$$

where $\Delta V_2$ is given in the next section below.
    END IF    ! End two Subcase 4.4 situations
  END IF    ! End Subcase 4.4
ELSE    ! Equatorial plane & northern hemisphere subcases
  IF ($\rho_s - r_s(z_{low}) \geq a_c$) THEN    ! Subcase 4.1
    keepGoing = FALSE
    (Because the sphere circle is shrinking away from the
cylinder circle, there is no chance for additional overlap.)
  ELSE IF ($\rho_s + r_s(z_{low}) \leq a_c$) THEN    ! Subcase 4.2

$$z_{high} = MIN[z_t, z_s + a_s]$$
$$V_{in} = V_{in} + \pi(z_{high} - z_{low})[a_s^2 - z_s^2 + z_s(z_{high} + Z_{low}) -$$
$$(z_{high}^2 + z_{high}z_{low} + z_{low}^2)/3]$$

keepGoing = FALSE
  ELSE IF ($r_s(z_{low}) - \rho_s > a_c$) THEN    ! Subcase 4.3

$$z_{high} = MIN\left[z_s + \sqrt{a_s^2 - (a_c + \rho_s)^2}, z_t\right]$$
$$V_{in} = V_{in} + \pi a_c^2(z_{high} - z_{low})$$

IF ($z_{high} = z_t$) keepGoing = FALSE
  ELSE IF (($r_s(z_{low}) > \rho_s$ AND $r_s(z_{low}) - \rho_s \leq a_c$ AND $a_c < r_s(z_{low}) + \rho_s$)
OR ($\rho_s \geq r_s(z_{low})$ AND $\rho_s - r_s(z_{low}) < a_c$ AND $a_c < \rho_s + r_s(z_{low})$))
THEN    ! Subcase 4.4

$$z_{high} = MIN\left[z_s + \sqrt{a_s^2 - (a_c - \rho_s)^2}, z_t\right]$$

IF ($a_s > a_c + \rho_s$) THEN $$V_{in} = V_{in} + \int_{z_{low}}^{z_{high}} dz A_{in} = V_{in} + \Delta V_3 \quad (176)$$

where $\Delta V_3$ is given in the next section below.
    ELSE $$V_{in} = V_{in} + \int_{z_{low}}^{z_{high}} dz\, A_{in} = V_{in} + \Delta V_4 \quad (177)$$

where $\Delta V_4$ is given in the next section below.
    END IF
    IF ($z_{high} = z_t$) keepGoing = FALSE
  END IF    ! End Subcase 4.4
  END IF    ! End Subcases
END IF    ! End hemisphere IF's
$z_{low} = z_{high}$    ! Prepare for next z interval
END DO    ! End DO WHILE loop $$\int_{z_{low}}^{z_{high}} dz A_{in}$$

$$\int_{z_{low}}^{z_{high}} dz A_{in} \qquad (178)$$

where $A_{in}$ is given by Eqs. 169d, 170a, 170b, 171a, and 171b as $$A_{in} = a_c^2 \cos^{-1}\left(\frac{\rho_s^2 + a_c^2 - a_s^2 + \zeta^2}{2\rho_s a_c}\right) + \qquad (179)$$

$$(a_s^2 - \zeta^2)\cos^{-1}\left(\frac{\rho_s^2 - a_c^2 + a_s^2 - \zeta^2}{2\rho_s\sqrt{a_s^2 - \zeta^2}}\right) -$$

$$\frac{1}{2}\sqrt{[\zeta^2 + (\rho_s + a_c)^2 - a_s^2][a_s^2 - (\rho_s - a_c)^2 - \zeta^2]}$$

with $$\zeta = z - z_s. \qquad (180)$$

This integral will involve elliptic integrals of the first, second, and third kinds which for present purpose are defined as in Abramowitz and Stegun. The incomplete elliptic integral of the first kind is given by $$F(\varphi, k) \equiv \int_0^\varphi d\theta \frac{1}{\sqrt{1 - k^2 \sin^2 \theta}}. \qquad (181)$$

The complete elliptic integral of the first kind is denoted by $K(k)$ and is equal to $F(\pi/2,k)$. Similarly, the incomplete elliptic integral of the second kind is given by $$E(\varphi, k) \equiv \int_0^\varphi d\theta \sqrt{1 - k^2 \sin^2 \theta}. \qquad (182)$$

with the complete elliptic integral of the second kind denoted by $E(k)$ and equal to $E(\pi/2,k)$. Finally, the incomplete elliptic integral of the third kind is given by $$\prod(\varphi, n, k) \equiv \int_0^\varphi d\theta \frac{1}{(1 - n\sin^2\theta)\sqrt{1 - k^2 \sin^2 \theta}}. \qquad (183)$$

with the complete elliptic integral of the third kind denoted by $\Pi(n,k)$ and equal to $\Pi(\pi/2,n,k)$. Various efficient routines for the evaluation of these special functions can be found in the literature.

Focusing on the integral of each of the three terms in Eq. 179, it is possible to perform an integration by parts of the first term of Eq. 179 to dispatch the inverse cosine term.

$$a_c^2 \int_{\zeta_1}^{\zeta_2} d\zeta \cos^{-1}\left(\frac{\rho_s^2 + a_c^2 - a_s^2 + \zeta^2}{2\rho_s a_c}\right) = \qquad (184)$$

$$a_c^2 \zeta \cos^{-1}\left(\frac{\rho_s^2 + a_c^2 - a_s^2 + \zeta^2}{2\rho_s a_c}\right)\bigg|_{\zeta_1}^{\zeta_2} + 2a_c^2 \int_{\zeta_1}^{\zeta_2} d\zeta \frac{\zeta^2}{R^{1/2}}$$

where $$R^{1/2} = \sqrt{[a_s^2 - (a_c - \rho_s)^2 - \zeta^2][\zeta^2 + (a_c + \rho_s)^2 - a_s^2]}. \qquad (185)$$

The right-most integral of Eq. 184 is an elliptic integral.

An integration by parts also may be used for beginning the integration of the second term of Eq. 179.

$$\int_{\zeta_1}^{\zeta_2} d\zeta (a_s^2 - \zeta^2)\cos^{-1}\left(\frac{\rho_s^2 - a_c^2 + a_s^2 - \zeta^2}{2\rho_s\sqrt{a_s^2 - \zeta^2}}\right) = \qquad (186)$$

$$\zeta\left(a_s^2 - \frac{\zeta^2}{3}\right)\cos^{-1}\left(\frac{\rho_s^2 - a_c^2 + a_s^2 - \zeta^2}{2\rho_s\sqrt{a_s^2 - \zeta^2}}\right)\bigg|_{\zeta_1}^{\zeta_2} -$$

$$\int_{\zeta_1}^{\zeta_2} d\zeta \zeta (3a_s^2 - \zeta^2) \frac{(a_c^2 + a_s^2 - \rho_s^2 - \zeta^2)}{3(a_s^2 - \zeta^2)R^{1/2}}$$

$$= \zeta\left(a_s^2 - \frac{\zeta^2}{3}\right)\cos^{-1}\left(\frac{\rho_s^2 - a_c^2 + a_s^2 - \zeta^2}{2\rho_s\sqrt{a_s^2 - \zeta^2}}\right)\bigg|_{\zeta_1}^{\zeta_2} +$$

$$\frac{2}{3}a_s^2(a_c^2 - \rho_s^2)\int_{\zeta_1}^{\zeta_2} d\zeta \frac{1}{R^{1/2}} -$$

$$\frac{1}{3}(a_c^2 + 3a_s^2 - \rho_s^2)\int_{\zeta_1}^{\zeta_2} d\zeta \frac{\zeta^2}{R^{1/2}} + \frac{1}{3}\int_{\zeta_1}^{\zeta_2} d\zeta \frac{\zeta^4}{R^{1/2}} -$$

$$\frac{1}{3}a_s^3(a_c^2 - \rho_s^2)\int_{\zeta_1}^{\zeta_2} d\zeta \frac{1}{(a_s^2 - \zeta^2)R^{1/2}}$$

where the integrals after the second equal sign in Eq. 186 come from partial fraction separation of the integrand after the first equal sign. Each of the integrals involves one or more elliptic integrals.

The third term of Eq. 179 is already in a form amenable to solution by elliptic integrals:

$$-\frac{1}{2}\int_{\zeta_1}^{\zeta_2} d\zeta R^{1/2}. \qquad (187)$$

Combining these three expressions in Eqs. 184, 186, and 187 yields the general expression for the $\Delta V$ used in Eqs. 174 to 177:

$$\Delta V = a_c^2 \zeta^2)\cos^{-1}\left(\frac{\rho_s^2 + a_c^2 - a_s^2 + \zeta^2}{2\rho_s a_c}\right) \qquad (188)$$

$$\bigg|_{\zeta_1}^{\zeta_2} + \zeta\left(a_s^2 - \frac{1}{3}\zeta^2\right)\cos^{-1}\left(\frac{\rho_s^2 - a_c^2 + a_s^2 - \zeta^2}{2\rho_s\sqrt{a_s^2 - \zeta^2}}\right)\bigg|_{\zeta_1}^{\zeta_2} + \frac{2}{3}a_s^2(a_c^2 - \rho_s^2)L_0 +$$

$$\left(\frac{5}{3}a_c^2 - a_s^2 + \frac{1}{3}\rho_s^2\right)L_2 + \frac{1}{3}L_4 - \frac{1}{3}a_s^3(a_c^2 - \rho_s^2)P - \frac{1}{2}E$$

where $$L_0 = \int_{\zeta_1}^{\zeta_2} d\zeta \frac{1}{R^{1/2}}, \qquad (189)$$

$$L_2 = \int_{\zeta_1}^{\zeta_2} d\zeta \frac{\zeta^2}{R^{1/2}}, \qquad (190)$$

$$L_4 = \int_{\zeta_1}^{\zeta_2} d\zeta \frac{\zeta^4}{R^{1/2}}, \qquad (191)$$

$$P = \int_{\zeta_1}^{\zeta_2} d\zeta \frac{1}{(a_s^2 - \zeta^2)R^{1/2}}, \qquad (192)$$

and $$E = \int_{\zeta_1}^{\zeta_2} d\zeta R^{1/2} \qquad (193)$$

with $R^{1/2}$ given by Eq. 185. The explicit solutions to the L, P, and E integrals of Eqs. 189 to 193 depend on the values of $\zeta_1$, $\zeta_2$, $a_s$, and $(a_c - \rho_s)$. These expressions are used in the preferred implementation.

Explicit Solution for Interior Volume $V_{in}$ when $a_s > a_c - \rho_s$

In the case where $a_s^2 > (a_c + \rho_s)^2$, the preferred implementation follows the $\zeta$ integration up the z axis, the southern hemisphere's sphere circle eventually circumscribes the cylinder circle unless it hits the top of the cylinder first. The limits of integration are therefore given by $$\zeta_1 = \text{MAX}[B, -(z_t - z_s)] \text{ and } \zeta_2 = \text{MIN}[A, -(z_b - z_s)] \qquad (194)$$

where A and B are given below. If $a_s^2 > (a_c + \rho_s)^2$, then it follows that $a_s^2 > (a_c - \rho_s)^2$. Therefore, we define $$A = \sqrt{a_s^2 - (a_c - \rho_s)^2} \qquad (195a)$$

and $$B = \sqrt{a_s^2 - (a_c + \rho_s)^2} \qquad (195b)$$

and note that A>B>0. Then $$R^{1/2} = \sqrt{(A^2 - \zeta^2)(\zeta^2 - B^2)}. \qquad (196)$$

The integrals for this form of $R^{1/2}$ are readily found in references such as Gradshteyn and Ryzhik. Define $$\lambda_1 = \sin^{-1}\sqrt{\frac{A^2 - \zeta_1^2}{A^2 - B^2}}, \qquad (197a)$$

$$\lambda_2 = \sin^{-1}\sqrt{\frac{A^2 - \zeta_2^2}{A^2 - B^2}}, \qquad (197b)$$

and $$q = \frac{\sqrt{A^2 - B^2}}{A}. \qquad (197c)$$

Then, recalling the definitions for the elliptic integrals of Eqs. 181 to 183, the following expressions for the integrals are obtained:

$$L_0 = A^{-1}[F(\lambda_1, q) - F(\lambda_2, q)], \quad \zeta_2 \leq A \qquad (198)$$

Note that $F(\lambda_2, q) = 0$ if $\zeta_2 = A$.

$$L_2 = A[E(\lambda_1, q) - E(\lambda_2, q)], \quad \zeta_2 \leq A \qquad (199)$$

Again, $E(\lambda_2, q) = 0$ if $\zeta_2 = A$.

$$L_4 = A/3[2(A^2 + B^2)E(\lambda_1, q) - B^2 F(\lambda_1, q)]$$
$$+ \zeta_1/3[(A^2 - \zeta_1^2)(\zeta_1^2 - B^2)]^{1/2} -$$
$$A/3[2(A^2 + B^2)E(\lambda_2, q) - B^2 F(\lambda_2, q)] +$$
$$\zeta_2/3[(A^2 - \zeta_2^2)(\zeta_2^2 - B^2)]^{1/2}, \quad \zeta_2 \leq A \qquad (200)$$

Note that the entire second line is zero if $\zeta_2 = A$.

$$P = \frac{1}{A(a_s^2 - A^2)}\left[\Pi\left(\lambda_1, \frac{A^2 - B^2}{A^2 - a_s^2}, q\right) - \Pi\left(\lambda_2, \frac{A^2 - B^2}{A^2 - a_s^2}, q\right)\right] \qquad (201)$$

The second elliptic integral with $\lambda_2$ as its first argument is zero if $\zeta_2 = A$.

Lastly, $$E = A/3[(A^2 + B^2)E(\lambda_1, q) - 2B^2 F(\lambda_1, q)] - \zeta_1/3$$
$$[(A^2 - \zeta_1^2)(\zeta_1^2 - B^2)]^{1/2} - A/3[(A^2 + B^2)E$$
$$(\lambda_2, q) - 2B^2 F(\lambda_2, q)] - \zeta_2/3[(A^2 - \zeta_2^2)$$
$$(\zeta_2^2 - B^2)]^{1/2}, \quad \zeta_2 \leq A \qquad (202)$$

Again, the entire second line of this expression is zero if $\zeta_2 = A$.

Explicit Solution for Interior Volume $V_{in}$ When $a_s \leq a_c + \rho_s$

In the case where $a_s^2 \leq (a_c + \rho_s)^2$, $A^2$ is still defined as it was before, $A^2 = a_s^2 - (a_c - \rho_s)^2$, but $B^2$ becomes the negative of its previous definition:

$$B^2 = (a_c + \rho_s)^2 - a_s^2. \qquad (203)$$

Although $A^2$ is always greater than zero, we simply have that $B^2 \geq 0$.

The radical is defined differently as $$R^{1/2} = \sqrt{(A^2 - \zeta^2)(\zeta^2 + B^2)} \qquad (204)$$

and that changes the elliptic integral solutions of $L_0$, $L_2$, $L_4$, P, and E. Defining $$\gamma_1 = \sin^{-1}\left(\frac{|\zeta_1|}{A}\sqrt{\frac{A^2 + B^2}{B^2 + \zeta_1^2}}\right) \qquad (205a)$$

$$\gamma_2 = \sin^{-1}\left(\frac{\zeta_2}{A}\sqrt{\frac{A^2 + B^2}{B^2 + \zeta_2^2}}\right) \qquad (205b)$$

$$r = \frac{A}{\sqrt{A^2 + B^2}} \qquad (205c)$$

the following expressions are obtained for the integrals. Note that $\zeta_1$ is inside absolute value signs so that only its magnitude is used. The upper limit $\zeta_2$, however, may be positive, negative, or zero. A negative $\zeta_2$ results in a change in sign for all terms in the integrals involving $\zeta_2$. All the integrands are even in $\zeta$ so that all the integrals are odd. The elliptic integrals are also odd in their first argument. The expressions for the desired integrals are now $$L_0 = \frac{1}{\sqrt{A^2+B^2}}[F(\gamma_1, r) + F(\gamma_2, r)] \quad (206)$$

$$L_2 = \sqrt{A^2+B^2}\, E(\gamma_1, r) - \frac{B^2}{\sqrt{A^2+B^2}} F(\gamma_1, r) - |\zeta_1|\sqrt{\frac{A^2-\zeta_1^2}{B^2+\zeta_1^2}} + \quad (207)$$
$$\sqrt{A^2+B^2}\, E(\gamma_2, r) - \frac{B^2}{\sqrt{A^2+B^2}} F(\gamma_2, r) - \zeta_2\sqrt{\frac{A^2-\zeta_2^2}{B^2+\zeta_2^2}}$$

$$L_4 = \frac{1}{3\sqrt{A^2+B^2}}[(2B^2-A^2)B^2 F(\gamma_1, r) - 2(B^4-A^4)E(\gamma_1, r)] - \quad (208)$$
$$\frac{|\zeta_1|}{3}(2A^2-B^2+\zeta_1^2)\sqrt{\frac{A^2-\zeta_1^2}{B^2+\zeta_1^2}} +$$
$$\frac{1}{3\sqrt{A^2+B^2}}[(2B^2-A^2)B^2 F(\gamma_2, r) - 2(B^4-A^4)E(\gamma_2, r)] -$$
$$\frac{\zeta_2}{3}(2A^2-B^2+\zeta_2^2)\sqrt{\frac{A^2-\zeta_2^2}{B^2+\zeta_2^2}}$$

$$P = \frac{1}{a_s^2(a_s^2+B^2)\sqrt{A^2+B^2}} \quad (209a)$$
$$[B^2\Pi(\gamma_1, n, r) + a_s^2 F(\gamma_1, r) + B^2\Pi(\gamma_2, n, r) + a_s^2 F(\gamma_2, r)]$$

where $$n = \frac{A^2(a_s^2+B^2)}{a_s^2(A^2+B^2)} \quad (209b)$$

and $$E = \frac{1}{3}\sqrt{A^2+B^2}\,[B^2 F(\gamma_1, r) - (B^2-A^2)E(\gamma_1, r)] + \quad (210)$$
$$\frac{|\zeta_1|}{3}(\zeta_1^2+2B^2-A^2)\sqrt{\frac{A^2-\zeta_1^2}{B^2+\zeta_1^2}} +$$
$$\frac{1}{3}\sqrt{A^2+B^2}\,[B^2 F(\gamma_2, r) - (B^2-A^2)E(\gamma_2, r)] +$$
$$\frac{|\zeta_2|}{3}(\zeta_2^2+2B^2-A^2)\sqrt{\frac{A^2-\zeta_2^2}{B^2+\zeta_2^2}}$$

which completes the solutions for the intersection of a sphere and cylinder. The explicit expressions for $\zeta_1$ and $\zeta_2$ are given earlier. These expressions are used in the preferred implementation to determine the intersection.

The task of determining the packing fraction also may be accomplished according to an aspect of the invention using a modified approach.

Recall that the radial distance of the sphere center from the z axis by $$\rho_s = [x_s^2 + y_s^2]^{1/2}. \quad (211)$$

Also recall that there are four possible cases for this overlap problem. In Case 1, the sphere is completely outside the cylinder so $V_{in}=0$. In Case 2, the sphere is completely inside the cylinder so $V_{in}=(4/3)\pi\alpha_s^3$. In Case 3, the cylinder is completely inside the sphere so $V_{in}=\pi\alpha_c^2(z_t-z_b)$. In Case 4, the sphere and cylinder intersect each other and the expression for $V_{in}$ is more complex as will be derived below.

Case 1: Sphere Completely Outside Cylinder

The sphere is completely outside the cylinder $$V_{in}=0 \quad (212)$$

only if one of the following conditions a re met:

If the sphere's north pole is lower than the cylinder bottom . . .

$$z_s+\alpha_s \leq z_b \quad (213a)$$

or if the sphere's south pl e is above the cylinder top . . .

$$z_s-\alpha_s \geq z_t \quad (213b)$$

or if the sphere is more than its radius away from the cylinder side . . .

$$\rho_s-\alpha_s \geq \alpha_c \quad (213c)$$

or if the sphere center is above the cylinder top and is more than its radius away from the upper cylinder edge . . .

$$(\rho_s-\alpha_c)^2+(z_s-z_t)^2 \geq \alpha_s^2 \text{ and } z_s>z_t \text{ and } \rho_s>\alpha_c \quad (213d)$$

or if the sphere center is below the cylinder bottom and is more than its radius away from the lower cylinder edge . . .

$$(\rho_s-\alpha_c)^2+(z_b-z_s)^2 \geq \alpha_s^2 \text{ and } z_s<z_b \text{ and } \rho_s>\alpha_c. \quad (213e)$$

Case 2: Sphere Completely Inside Cylinder

The sphere is completely inside the cylinder $$V_{in}=(4/3)\pi\alpha_s^3 \quad (214)$$

only if all three of the following conditions are simultaneously met:

if the sphere's north pole is no higher than the cylinder top . . .

$$z_s+\alpha_s \leq z_t \quad (215a)$$

and if the sphere's south pole is no lower than the cylinder bottom . . .

$$z_s-\alpha_s \geq z_b \quad (215b)$$

and if the sphere's equator nowhere exceeds the cylinder radius . . .

$$\rho_s+\alpha_s \leq \alpha_c. \quad (215c)$$

Case 3: Cylinder Completely Inside Sphere

The cylinder is completely inside the sphere $$V_{in}=\pi\alpha_c^2(z_t-z_b) \quad (216)$$

if both the following two conditions are met:

if the upper edge of the cylinder is inside the sphere . . .

$$(\rho_s+\alpha_c)^2+(z_t-z_s)^2 \leq \alpha_s^2 \quad (217a)$$

and if the lower edge of the cylinder is inside the sphere . . .

$$(\rho_s + \alpha_c)^2 + (z_s - z_b)^2 \leq \alpha_s^2. \quad (217b)$$

Case 4: Cylinder and Sphere Intersect

Again, there are several subsets of Case 4. To efficiently organize them, we define two circles: the sphere circle and the cylinder circle. The sphere circle is the perimeter of the sphere's cross-section at a given z altitude. Its radius is $$r_s = [\alpha_s^2 - (z-z_s)^2]^{1/2}, \; z_s - \alpha_s \leq z \leq z_s + \alpha_s \quad (218)$$

and its radial position $\rho_s$ is given by Eq. 211. Likewise, the cylinder circle is the perimeter of the cylinder's cross-section which has constant radius $\alpha_c$ at any z altitude between $z_b$ and $z_t$ and is centered on the z axis.

To describe the intersection of the sphere and cylinder, we define four subcases for the relationship of the sphere circle and the cylinder circle at a particular altitude z:

Subcase 4.1: The sphere circle is completely enclosed in the cylinder circle.

Subcase 4.2: The two circles do not overlap or one or both are nonexistent.

Subcase 4.3: The cylinder circle is completely enclosed in the sphere circle.

Subcase 4.4: The two circles intersect.

To find $V_{in}$, our task is reduced to integrating in z the overlap areas of the two circles $A_{in}$ from the altitude where one subcase holds to the altitude where another subcase holds.

For Subcase 4.1, $A_{in} = \pi \alpha_s^2$. (219a)

For Subcase 4.2, $A_{in} = 0$. (219b)

For Subcase 4.3, $A_{in} = \pi \alpha_c^2$. (219c)

For Subcase 4.4, $A_{in} = \alpha_c^2(\alpha - \cos\alpha \sin\alpha) + r_s^2(\beta - \cos\beta \sin\beta)$ (219d)

where $r_s$ is given by Eq. 218 and $$\cos\alpha = \frac{\rho_s^2 + a_c^2 - r_s^2}{2\rho_s a_c} \quad (220a)$$

$$\sin\alpha = \frac{\sqrt{[r_s^2 - (a_c - \rho_s)^2][(a_c + \rho_s)^2 - r_s^2]}}{2\rho_s a_c} \quad (220b)$$

$$\cos\beta = \frac{\rho_s^2 + r_s^2 - a_c^2}{2\rho_s r_s} \quad (221a)$$

$$\sin\beta = \frac{\sqrt{[r_s^2 - (a_c - \rho_s)^2][(a_c + \rho_s)^2 - r_s^2]}}{2\rho_s r_s}. \quad (221b)$$

It is now necessary to determine a series of altitudes at which the cylinder circle and the sphere circle change from one subcase to another in Case 4.

A sphere and a cylinder side can intersect each other at either 0, 2, or 4 altitudes. Pairs of altitudes may be degenerate (two solutions having the same altitude) if the sphere just nicks the cylinder wall. The solutions for these altitudes come from solving the following equation:

$$[r_s(z)]^2 = [\alpha_c \pm \rho_s]^2 \quad (222a)$$

or $$\alpha_s^2 - (z-z_s)^2 = [\alpha_c \pm \rho_s]^2 \quad (222b)$$

which, using Eq. 218, has the four solutions $$z = z_s \pm \sqrt{\alpha_s^2 - (\alpha_c \pm \rho_s)^2}. \quad (223)$$

The + sign in the first ± of Eq. 223 denotes the upper or northern hemisphere intersection altitude; the − sign denotes the lower or southern hemisphere intersection altitude. The + sign in the second ± of Eq. 223 denotes intersection with the far cylinder wall, on the opposite side of the z axis from the sphere's side; the − sign denotes intersection with the near cylinder wall, on the same side of the z axis as the sphere.

Armed with these four solutions, we will now consider each of the four subcases of Case 4, but we will consider separately whether the sphere circle lies in the southern hemisphere of the sphere or whether it is the equatorial plane or northern hemisphere. We consider the four subcases separately for the two hemispheres making eight situations in all. We consider the hemispheres separately because if the sphere circle is in the southern hemisphere, it is increasing in size as z increases. Hence, the preferred implementation can determine the altitude at which subcases change. If the sphere circle is its equatorial plane or is its northern hemisphere, it is decreasing in size as z decreases, and the altitude at which subcases will change again can be determined.

We now outline the overall logic used in the preferred implementation to find the altitudes at which the subcases for Case 4 change. Let $z_{low}$ be the lower altitude of the subcase region currently being examined and $z_{high}$ be its upper altitude.

The absolute boundary below or above, with never any overlap between sphere and cylinder, is given by $$z_0 = \text{MAX}[z_b, z_s - \alpha_s] \quad (224)$$

for the lower boundary and $$z_5 = \text{MIN}[z_t, z_s + \alpha_s] \quad (225)$$

for the upper boundary. The altitudes $z_1$ through $z_4$ correspond to the different intersection altitudes (if they exist) of the sphere's polar plane that is perpendicular to the cylinder axis. A sphere's polar plane is the plane which intersects the sphere in a great circle perpendicular to the equatorial plane. It can be oriented at any azimuthal angle. The polar plane of interest to us is the one passing through the cylinder axis.

In ascending order (again, if they exist) the intersection altitudes are:

Southern hemisphere intersection with cylinder wall closest to sphere center:

$$z_1 = z_s - \sqrt{\alpha_s^2 - (a_c - \rho_s)^2} \quad (226)$$

Southern hemisphere intersection with cylinder wall furthest from sphere center:

$$z_2 = z_s - \sqrt{\alpha_s^2 - (a_c + \rho_s)^2} \quad (227)$$

Northern hemisphere intersection with cylinder wall furthest from sphere center:

$$z_3 = z_s + \sqrt{\alpha_s^2 - (a_c + \rho_s)^2} \quad (228)$$

Northern hemisphere intersection with cylinder wall closest to sphere center:

$$z_4 = z_s + \sqrt{a_s^2 - (a_c - \rho_s)^2}. \qquad (229)$$

In all four of these solutions, if the argument of the square root is negative, the square root is replaced by zero. If the sphere intersects both sides of the cylinder, there are four real solutions; if only one side, there are two real solutions; if not at all, there are no real solutions of Eqs. 226 through 229. The figure below shows the two real solutions for a sphere that intersects only one side of the cylinder.

The method used in the preferred implementation for finding the volume $V_{in}$ of a sphere that lies inside a cylinder will now be discussed. The method is divided into two DO WHILE loops, one for the southern hemisphere and one for the northern hemisphere (which includes the sphere's equatorial plane). This is convenient because for the southern hemisphere the sphere circle is always increasing with increasing z while for the northern hemisphere it is always decreasing. The method as specifically implemented here has a number of comments so that the reader can follow the reasoning guiding it.

```
V_in = 0          ! V_in is the volume of this sphere lying inside the
                  ! cylinder. Initialize it to zero.
z_0 = MAX[z_b, z_s - a_s]    ! z_0 and z_5 are the absolute lower and upper
z_5 = MIN[z_t, z_s + a_s]    ! limits of possible sphere-cylinder overlap.
IF (z_s > z_b) THEN ! The southern hemisphere can contribute to V_in if and
                    ! only if this statement is true. Otherwise it lies
                    ! beneath the cylinder bottom and cannot contribute.
                    ! (It might not contribute even when the above
                    ! statement is true but that is checked below.)
    z_low = z_0         ! Initialize z_low to smallest possible value.
    r_s(z_low) = [a_s^2 - [z_low - z_s]^2]^{1/2}   ! Find initial sphere circle
                                                  ! radius. It is 0 if square
                                                  ! root argument ≦ 0.
! Find the initial southern hemisphere subcase.
    IF (ρ_s + r_s(z_low) < a_c) THEN
        subcase = 1      ! Sphere circle inside cylinder circle.
    ELSE IF (ρ_s - r_s(z_low) > a_c) THEN
        subcase = 2      ! Sphere circle outside cylinder circle.
    ELSE IF (r_s(z_low) - ρ_s ≧ a_c) THEN
        subcase = 3      ! Cylinder circle inside sphere circle.
    ELSE
        subcase = 4      ! Sphere circle intersects cylinder circle.
    END IF
! We exit the DO WHILE loop when the subcase is no longer a positive
! integer. Remember that since we are in the southern hemisphere, the
! sphere circles are expanding with increasing z.
    DO WHILE (subcase > 0) ! Southern hemisphere loop.
        IF (subcase = 1) THEN
            ! The sphere circle lies inside the cylinder circle.
            ! It expands with increasing z until one of three
            ! things happen:
            ! (1) It hits the top of the cylinder.
            ! (2) It intersects the cylinder circle.
            ! (3) It reaches its equatorial plane.
            ! Numbers (2) and (3) can be combined if we agree to
            ! define z_1 with the square root replaced by zero if
            ! its argument is negative.
            w = a_s^2 - (a_c - ρ_s)^2
            IF (w > 0) THEN
                z_1 = z_s - w^{1/2}
            ELSE
                z_1 = z_s
            END IF
            z_high = MIN[z_t, z_1]
            V_in = V_in + V_1(z_low, z_high)   ! We'll derive an explicit
                                               ! expression for this V_1 later.
! Now we must find the next subcase.
            IF (z_high < MIN[z_s, z_1]) THEN     ! There is another
                                                 ! subcase to be
                                                 ! addressed in the
                                                 ! southern hemisphere.
                IF (ρ_s > 0) THEN                ! Sphere is not concentric with
                    subcase = 4                  ! the cylinder so it will
                                                 ! expand until it intersects.
                ELSE                             ! Here, the sphere is concen-
                    subcase = 3                  ! tric so it will expand
                END IF                           ! until it perfectly circum-
                                                 ! scribes the cylinder
                                                 ! circle.
            ELSE                                 ! You reached the end of southern
                subcase = 0                      ! hemisphere contribution. End the
            END IF                               ! S. hemisphere's DO WHILE loop.
        ELSE IF (subcase = 2) THEN
```

-continued

```
            ! The sphere circle lies outside the cylinder circle
            ! until it expands to the point where it intersects
            ! the cylinder. This intersection must happen or we
            ! wouldn't be here in Case 4. The intersection
            ! happens at z₁. There is no contribution to V_in from
            ! this region. We only need to find z_high = z₁.
            w = a_s² − (a_c − ρ_s)²
            IF (w > 0) THEN
                    z_high = z_s − w^(1/2)
                    subcase = 4  ! Not done yet with S. hemisphere.
            ELSE
                    z_high = z_s
                    subcase = 0      ! Reached equatorial plane. Now
            END IF                   ! we're done with S. hemisphere.
        ELSE IF (subcase = 3) THEN
            ! The cylinder circle lies inside the sphere circle.
            ! Since the sphere circle is expanding, it will
            ! remain inside until it reaches the first of either
            ! the top of the cylinder or its equatorial plane.
            z_high = MIN[z_t, z_s]
            V_in = V_in + V₂(z_low, z_high)       ! We'll derive an explicit
                                                  ! expression for this V₂ later.
            subcase = 0
        ELSE IF (subcase = 4) THEN
            ! The only possibility left is that sphere and
            ! cylinder circles initially intersect. This region
            ! extends upward until one of three things happen:
            ! (1) We reach the top of the cylinder.
            ! (2) We reach the sphere's equatorial plane.
            ! (3) We reach a point at which the sphere circle
            !     completely circumscribes the cylinder circle.
            ! We cannot reach the top of the sphere in this case
            ! because we are only dealing with the southern
            ! hemisphere. (Remember z₂ = z_s if the argument of
            ! the square root is negative.)
            w = a_s² − (a_c + ρ_s)²
            IF (w > 0) THEN
                    z₂ = z_s − w^(1/2)
                    subcase = 3
            ELSE
                    z₂ = z_s
                    subcase = 0
            END IF
            z_high = MIN[z_t, z_s, z₂]
            V_in = V_in + V₃(z_low, z_high)       ! We'll derive a numerical
                                                  ! integration for this V₃ later.
        END IF
        ! If you have reached either the cylinder top or the
        ! sphere's equatorial plane, you are done with the southern
        ! hemisphere's contribution to V_in. Go to the northern
        ! hemisphere next. (We use ≧ signs below in case of round-
        ! off error. With infinite precision, z_high could never be
        ! greater than z_t or z_s.)
        IF (z_high ≧ z_t OR z_high ≧ z_s) THEN ! Redundant check saying
                subcase = 0        ! we're done with the southern hemisphere.
        ELSE
                z_low = z_high     ! Cycle back through the DO WHILE loop
        END IF                     ! for the next region in the southern
                                   ! hemisphere contributing to V_in.
    END DO    ! End of southern hemisphere DO WHILE loop.
END IF        ! End of southern hemisphere overall IF statement.
IF (z_s < z_t) THEN   ! The northern hemisphere can contribute to V_in if and
                      ! only if this statement is true. Otherwise it lies
                      ! above the cylinder top and cannot contribute. (It
                      ! might not contribute even when the above statement
                      is true.)
    z_low = MAX[z_b, z_s]
    r_s(z_low) = [a_s² − (z_low − z_s)²]^(1/2)   ! Find initial sphere circle radius in
                                                  ! N. hemisphere. It is 0 if square root
                                                  ! argument ≦ 0.
! Find the initial northern hemisphere subcase.
    IF (ρ_s + r_s(z_low) ≦ a_c) THEN
            subcase = 1        ! Sphere circle inside cylinder circle.
    ELSE IF (ρ_s − r_s(z_low) ≧ a_c) THEN
            subcase = 0        ! Sphere circle outside cylinder circle.
                               ! Although this is actually subcase 2, since
                               ! N. hemisphere sphere circle can only contract
                               ! it will never intersect the cylinder
                               ! circle if it does not initially intersect it.
```

-continued

```
                          ! Therefore, we set the subcase to zero so the
                          ! N. hemisphere's DO WHILE loop will end.
     ELSE IF (ρ_s + a_c < r_s(z_low)) THEN
          subcase = 3         ! Cylinder circle inside sphere circle.
     ELSE
          subcase = 4         ! Sphere circle intersects cylinder circle.
     END IF
     DO WHILE (subcase > 0) ! Begin northern hemisphere loop.
          IF (subcase = 1) THEN
               ! The sphere circle lies inside the cylinder circle.
               ! Since the sphere circle shrinks as z increases, it
               ! cannot ever intersect the cylinder circle. It can
               ! only end at its north pole or at the top of the
               ! cylinder. That ending position is z_5.
               z_high = z_5
               V_in = V_in + V_1(z_low,z_high)    ! We'll derive an explicit
                                                  ! expression for V_1 later.
               subcase = 0
          ELSE IF (subcase = 2) THEN
               ! The sphere circle is inside the cylinder circle.
               ! In the northern hemisphere this means they will
               ! never intersect more so there will be no more
               ! contribution to V_in.
               subcase = 0
          ELSE IF (subcase = 3) THEN
               ! The cylinder circle lies inside the sphere circle.
               ! The sphere circle will contract until we hit top
               ! of the cylinder or until we reach z_3 which is the
          ! point at which the two circles will intersect.
               w = a_s^2 − (a_c + ρ_s)^2         ! w is non-negative or we
                                                  ! couldn't be here.
               z_3 = z_s + w^{1/2}
               z_high = MIN[z_t, z_3]
               V_in = V_in + V_2(z_low,z_high)    ! We'll derive an explicit
                                                  ! expression for V_2 later.
               IF (z_high < z_t) THEN
                         IF (ρ_s > 0) THEN         ! Sphere is not concentric
                              subcase = 4          ! with cylinder so it will
                                                   ! contract until it inter-
                                                   ! sects the cylinder circle.
                         ELSE                      ! The sphere is concentric so
                              subcase = 1          ! it will contract until it
                         END IF                    ! suddenly lies completely
                                                   ! inside the cylinder circle.
               ELSE                                ! If we're here, we reached
                         subcase = 0               ! top of the cylinder; we're
               END IF                              ! done with N. hemisphere.
          ELSE IF (subcase = 4) THEN
               ! The only possibility left is that sphere and
               ! cylinder circles initially intersect. This region
               ! extends upward until one of two things happen:
               ! (1) We reach the top of the cylinder before
               !     reaching the north pole.
               ! (2) The intersection stops with the sphere circle
               !     now either completely inside or completely
               !     outside the cylinder circle. This happens at
               !     z_4.
               w = a_s^2 − (a_c − ρ_s)^2         ! w is never negative or we
                                                  ! wouldn't be here.
               z_4 = z_s + w^{1/2}
               z_high = MIN[z_t, z_4]
               V_in = V_in + V_3(z_low,z_high)    ! We'll derive a numerical
                                                  ! solution for V_3 later.
               IF (ρ_s < a_c) THEN
                         subcase = 1               ! Next, sphere circle will lie
                                                   ! inside cylinder circle.
               ELSE
                         subcase = 0               ! Next, sphere circle will lie
                                                   ! outside cylinder circle.
               END IF
          END IF
! (Note the second logical expression in the IF statement below is z_5,
! not z_s.)
          IF (z_high ≥ z_t OR z_high ≥ z_5) THEN   ! Redundant check saying
                    subcase = 0                     ! we're done with northern hemisphere.
          ELSE
                    z_low = z_high                  ! Cycle back through the DO WHILE loop
```

-continued

```
         END IF              ! for the next region in the northern
                             ! hemisphere's contribution to V_in.
    END DO       ! End of northern hemisphere DO WHILE loop.
END IF           ! End of northern hemisphere overall IF statement.
```

Expressions for the three volume expressions $V_i(z_{low}, z_{high})$, i=1, 2, or 3 will now be addressed. Remember in the following that $\alpha_c$ is the cylinder radius, $\alpha_s$ is the sphere radius, $(x_s, y_s, z_s)$ is the position of the sphere's center, and $\rho_s = \sqrt{x_s^2 + y_s^2}$ is the radial distance of the sphere center from the cylinder axis.

DERIVATION OF $V_1$

The volume $V_1$ is an integral of full sphere circles from $z_{low}$ to $z_{high}$ because the sphere circles lie entirely within the cylinder circle.

$$V_1 = \pi \int_{z_{low}}^{z_{high}} dz [r_s(z)]^2 = \pi \int_{z_{low}}^{z_{high}} dz [a_s^2 - (z - z_s)^2] \quad (230)$$

or $$V_1 = \frac{\pi}{3}(z_{high} - z_{low})[3a_s^2 - z_{high}^2 - z_{low}^2 + z_{high}(3z_s - z_{low}) - 3z_s(z_s - z_{low})] \quad (231)$$

where $z_{low}$ and $z_{high}$ depend on where we are in the above method. Their values are given in the implementation shown above.

DERIVATION OF $V_2$

The volume $V_2$ is the integral of the cylinder circle from $z_{low}$ to $z_{high}$ because the cylinder circle lies entirely within the sphere circle. It is given simply as $$V_2 = \pi \alpha_c^2 (z_{high} - z_{low}). \quad (232)$$

DERIVATION OF $V_3$

The volume $V_3$ is the integral of intersecting sphere and cylinder circles from $z_{low}$ to $z_{high}$. The limits are always given in the method as described above. The intersect area is given by Eqs. 219, 220, and 221 which we must integrate in z.

$$V_3 = \int_{z_{low}}^{z_{high}} dz \{a_c^2 [\alpha - \cos\alpha \sin\alpha] + [a_s^2 - (z - z_s)^2][\beta - \cos\beta \sin\beta]\} \quad (233)$$

where $$\cos\alpha = \frac{\rho_s^2 + a_c^2 - a_s^2 + (z - z_s)^2}{2\rho_s a_c} \quad (234)$$

$$\sin\alpha = \frac{\sqrt{[a_s^2 - (a_c - \rho_s)^2 - (z - z_s)^2][(a_c + \rho_s)^2 - a_s^2 + (z - z_s)^2]}}{2\rho_s a_c} \quad (235)$$

$$\alpha = \arccos\left[\frac{\rho_s^2 + a_c^2 - a_s^2 + (z - z_s)^2}{2\rho_s a_c}\right] \quad (236)$$

and $$\cos\beta = \frac{\rho_s^2 - a_c^2 + a_s^2 + (z - z_s)^2}{2\rho_s \sqrt{a_s^2 - (z - z_s)^2}} \quad (237)$$

$$\sin\beta = \frac{\sqrt{[a_s^2 - (a_c - \rho_s)^2 - (z - z_s)^2][(a_c + \rho_s)^2 - a_s^2 - (z - z_s)^2]}}{2\rho_s \sqrt{a_s^2 - (z - z_s)^2}} \quad (238)$$

$$\beta = \arccos\left[\frac{\rho_s^2 - a_c^2 + a_s^2 + (z - z_s)^2}{2\rho_s \sqrt{a_s^2 - (z - z_s)^2}}\right]. \quad (239)$$

The integral of Eq. 233 could be done analytically in terms of complete and incomplete elliptic integrals of the first, second, and third kinds. However, this solution is so cumbersome that it is more efficient to perform it numerically, especially because the integrand is quite smooth and well-behaved so that a Romberg integration is very efficient and contains an accurate error assessment.

Calculating the Total Volume Fraction for a Pack

The preferred implementation also can determine the volume fraction $\phi$ of the pack. Only the innermost cylinder contains particles that look like a full three-dimensional pack. The outer cylinders do not contain the particles the inner cylinders contain. However, it would be unfortunate to throw away all the pack information the outer cylinders contain. They do perturb the pack of the innermost cylinder correctly and their correct geometry for the particles they contain should somehow be used in estimating the volume fraction of the pack.

The preferred implementation determines the volume fraction $\phi$ in the following way. The j-th cylinder can contain all particle modes whose cylinder radii are less than or equal to its cylinder radius $\alpha_c(j)$. As long as the water level option of pack building is operating, the j-th mode particles are distributed approximately as they would be in a truly three-dimensional pack. The preferred implementation therefore calculates the volume fraction $\phi_j$ of Mode j particles within the j-th cylinder and calls it the j-th partial volume fraction. It does likewise for all the other modes, e.g., J of them. Then the total volume fraction is simply the sum of all the partial volume fractions:

$$\phi = \sum_{j=1}^{J} \phi_j. \tag{240}$$

If desired, the user can specify that only the volume fraction of the innermost cylinder, where the pack is three dimensional, will be calculated.

To calculate the partial volume fraction $\phi_j$ in the j-th cylinder, the preferred implementation sums the interior volume of each Mode j sphere inside the j-th cylinder. Let $n_j$ be the number of Mode j spheres in the j-th cylinder. Let $V_j(k)$ be the volume inside the cylinder of the k-th sphere of Mode j. Then $$V_{tot}(j) = \sum_{k=1}^{n_j} V_j(k). \tag{241}$$

Dividing this total interior partial volume by the volume of the j-th cylinder $V_{cyl}(j)$ gives the partial volume fraction $\phi_j$ for the pack:

$$\phi_j = V_{tot}(j)/V_{cyl}(j) \tag{242}$$

where $$V_{cyl}(j) = \pi [a_c(j)]^2 [z_{top}(j) - z_{bot}(j)]. \tag{243}$$

The user has the option of making calculating volume fractions in cylinders that are a little smaller than the actual cylinders used in making the pack so that possible wall effects can be eliminated from the calculation. Remember, however, that the cylinder walls are barriers to the particle centers, not their leading edges so that disturbances to the pack from wall effects normally will be small.

Finding the Radial Distribution Functions

The radial distribution functions, denoted by $g_{ij}(r)dr$, are probability distribution functions denoting the mean number of Mode or Submode j particles whose centers are between r and r+dr from the centers of Mode or Submode i particles throughout the pack. They can be important in establishing many properties of random packs. Because the packs here are assumed random, only the scalar radial distance r is used rather than vector r in this implementation.

Reduced dimension packs do not extend equally in all directions. They are a series of concentric cylinders. Therefore, for a given Mode or Submode i particle, the preferred implementation calculates the volume of the spherical shell segment centered on Particle i and lying between r and r+dr, that lies inside the j-th cylinder. Then it counts all Mode j particles lying in that shell segment. Dividing the number of Mode j particles by the volume of the shell segment gives an approximation to $g_{ij}(r)dr$ at that position r.

Finding the volume of this spherical shell segment is not a trivial procedure. Fortunately, a means to calculate the total sphere volume lying inside any cylinder is described above. Therefore, the preferred implementation can calculate the total volume of an imaginary sphere of radius r+dr, centered at Particle i, that lies inside the j-th cylinder, and subtract from it the total volume of the concentric sphere of radius r to obtain the volume of the spherical shell segment between r and r+dr lying in the j-th cylinder.

The user specifies the maximum radial distance $r_{max}(i,j)$ for which $g_{ij}$ is desired and the number of bins $m_{ij}$ into which it divided $r_{max}(i,j)$. Then the bin widths have finite width $$\Delta r_{ij} = r_{max}(i,j)/m_{ij} \tag{244}$$

rather than infinitesimal width dr. Then the gy are determined as follows.

First, note that the $g_{ij}(r)$ are zero for $r < \alpha_i + \alpha_j$. Then, consider a particular Mode i particle with index number $i_h$. Denote the number of Mode j particles in the first bin from Particle $i_h$ particle by $N_j(i_h; \alpha_i + \alpha_j)$. The first bin lies between $(\alpha_i + \alpha_j)$ and $(\alpha_i + \alpha_j) + \Delta r_{ij}$. In general, the number of Mode j particles lying in the k-th bin from Particle $i_h$ is denoted by $N_j(i_h; r_k)$ where $r_k = \alpha_i + \alpha_j + (k-1)\Delta r_{ij}$, $k=1, 2, \ldots, m_{ij}$.

Now consider the volume of the k-th bin from Particle $i_h$ that lies inside the j-th cylinder. This can be obtained from the volumes $V_{in}$ of previous sections where $V_{in} = V_{in}(x_s, y_s, z_s, \alpha_s; \alpha_c, z_{bot}, z_{top})$. The argument list contains the position of the sphere center $(x_s, y_s, z_s)$, the sphere radius $\alpha_s$, the cylinder radius $\alpha_c$, and the cylinder's bottom and top altitudes $(z_{bot}, z_{top})$. The volume for the k-th bin about Particle $i_h$ is then given by $$V_{in}(i_h,j;k) = V_{in}(x_{ih}, y_{jh}, z_{ih}, r_{k+1}; a_{cj}, z_{botj}, z_{topj}) - V_{in}(x_{ih}, y_{ih}, z_{ih}, r_k; a_{cj}, z_{botj}, z_{topj}) \tag{245}$$

and the number density of Mode j particles in this volume is $$\sigma(i_h,j; k) = N_j(i_h; r_k)/V_{in}(i_h,j; k). \tag{246}$$

Finally, to obtain the $g_{ij}(r)$, the above expression can be averaged over all Mode i particles:

$$g_{ij}(r) \cong \frac{1}{n_i} \sum_{i_h}^{n_i} \sigma(i_h, j; k) \tag{247}$$

if $r > \alpha_i + \alpha_j$ and is zero otherwise. The term k is the integer lying in the range $$(r - a_i - a_j)/\Delta r_{ij} < k \leq 1 + (r - a_i - a_j)/\Delta r_{ij}. \tag{248}$$

If r is so large or so small for a particular particle $i_h$ that the spherical shell containing it misses the j-th cylinder altogether, then that term in the sum of Eq. 247 is omitted altogether.

The normalized radial distribution function, denoted $G_{ij}(r)$, is given by $$G_{ij}(r) = g_{ij}(r)/(4\pi r^2) \tag{249}$$

or in our finite bin width treatment, it is given by $$G_{ij}(r) = \frac{g_{ij}(r)}{\frac{4}{3}\pi(r_{k+1}^3 - r_k^3)}. \tag{250}$$

It is the mean number density $n_j$ of Type j particles at a distance r from a Type i particle. Thus normalized, the function $G_{ij}(r)$ approaches the constant $n_j$ as r grows large rather than increase quadratically as $g_{ij}(r)$ does. $n_j$ represents the number of j particles per unit volume, e.g., concentration, output from the preferred implementation.

Finding the Coordination Numbers

The coordination number $\Omega_{ij}$ is the mean number of Mode j particles touching a Mode i particle. Again, because a reduced dimension pack is ordered in concentric cylinders rather than being isotropic in all directions, the preferred implementation finds how much of the surface of the i-th particle is available for Mode j particles to touch. That is equivalent to asking how much of the imaginary spherical surface centered on the Mode i particle and having radius $\alpha_i + \alpha_j$ lies inside the j-th cylinder. We will denote that interior portion of the surface by $S_{ij}$. Then if a search shows there are $h_{ij}$ Mode j particles touching a particular Mode i particle identified by index number $i_h$, then our best estimate of the total number of touching Mode j spheres, if the entire surface were accessible, would be $$\eta_{ij} = h_{ij} 4\pi (a_i + a_j)^2 / S_{ij}. \qquad (251)$$

If the entire surface is accessible, then $S_{ij} = 4\pi(a_i + a_j)^2$ and $\eta_{ij} = h_{ij}$. Because of round-off error, a certain center-to-center error tolerance $\epsilon$ is required to determine whether two spheres are indeed touching. The code considers them touching if their centers are within the distance $(\alpha_i + \alpha_j)(1+\epsilon)$ from each other. Because the preferred implementation is in double precision, the default for $\epsilon$ is $10^{-12}$, but the user can specify any other desired $\epsilon$. Normally it should be a few orders of magnitude greater than machine precision.

The spherical surface $S_{ij}$ lying inside a cylinder could be obtained from our earlier work on obtaining the spherical volume inside a cylinder by taking a derivative of the volume expressions with respect to the sphere radius. However, those expressions are complicated and have substantial bookkeeping associated with them. Because in this implementation there is an error tolerance, we may take a numerical derivative as follows:

$$S_{ij} = \epsilon^{-1}[V_{in}(x_{ih}, y_{ih}, z_{ih}, (a_i+a_j)(1+\epsilon); a_c(j), z_{botj}, z_{topj}) - V_{in}(x_{ih}, y_{ih}, z_{ih}, (a_i+a_j); a_c(j), z_{botj}, z_{topj})]. \qquad (252)$$

The $\epsilon$ used in this expression should be kept very small even if the user chooses to be rather liberal in assigning a rather large error tolerance. One might, for example, assign this $\epsilon$ to be either the user-defined (or default) error tolerance or $10^{-6}$, whichever is smaller.

Finding Various Pack Statistics

There are a number of vital statistics of the pack that will generally be of interest. If the user so specifies, then the following data is written to a user-named file.

1. A recapitulation of the particle histogram.
2. A recapitulation of the values for control flags and parameters used in building the pack.
3. The total number of particles placed in the pack and the number placed from each mode.
4. The minimum and maximum radial and axial positions for the centers of all particles in the pack and the same for each mode.
5. Radial and axial particle density functions for each mode specified between the minimum and maximum positions specified above.
6. The number of particles placed after tunneling (if tunneling is permitted).
7. The number of particles hitting one of the catch nets.
8. The number of particles hitting one of the water levels.
9. The number of preplaced particles, if any.

It is important to understanding in implementing the various aspects of the invention and in applying the related principles that the mathematical equations and expression presented herein may be assumed to have an infinite degree of precision and all real implementations of those equations result in answers with finite precision. Many programmers assume that the use of double precision, 64-bit precision, eliminates the need for close attention to this fact. Such an assumption with this problem typically will be incorrect. For example, in testing the implementation of several equations, cases were found where use of quadruple precision, 128-bit precision, was insufficient to obtain correct solutions. These cases were avoided if in the solution process checks were made that allowed for tolerance bands. Every check for equality must include equality within a tolerance. The following tolerances are used within the preferred implementation.

1. Comparison with zero. Numbers in the range $-1.0E-20 <$ number $<1.0E-20$ are treated as zero.
2. General comparison for equality. Any two non-zero numbers are within $1.0E-10$ times the smaller of the two numbers are treated as equal.
3. General angle comparison for equality. Any two angles within $1.0E-6$ radians are treated as equal.
4. Distance comparison. Any two distances within $1.0E-6$ times the smallest particle radius are treated as equal.
5. Distance squared comparison. Any two numbers representing distance squared within $1.0E-6$ times the square of the smallest particle radius are treated as equal.

Additional advantages and modifications will readily occur to those skilled in the art. Therefore, the invention in its broader aspects is not limited to the specific details, representative devices and methods, and illustrative examples shown and described. Accordingly, departures may be made from such details without departing from the spirit or scope of the general inventive concept as defined by the appended claims and their equivalents.

What is claimed is:

1. A machine-implemented method for simulating placement of a plurality of unplaced particles, the method comprising:

selecting a plurality of unplaced particles;

wherein each of the plurality of unplaced particles exhibits a characteristic dimension, corresponding to N categories of the plurality of unplaced particles;

wherein the characteristic dimension of each of the plurality of unplaced particles of a given category of the N categories is different from the characteristic dimension of each of the plurality of unplaced particles of other of the N categories;

defining a central string, a space disposed about the central string, and N subspaces disposed about the central string and within the space, wherein each of the N subspaces corresponds to one of the N categories, respectively;

selecting a particle from the plurality of unplaced particles;

defining a catch net representative of buoyancy of a portion of a plurality of placed particles and positioning the catch net within the space based upon placement of the portion of the plurality of placed particles;

defining a water level representative of a level of a portion of the plurality of placed particles that are smaller than the selected particle;

simulating placement of the selected particle within a corresponding subspace so that the selected particle is positioned in a non-overlapping relationship with respect to the plurality of placed particles, the catch net, and the water level; and repeatedly selecting another particle from the plurality of unplaced particles and simulating placement thereof until placement of each of the plurality of unplaced particles has been simulated.

2. The method as recited in claim 1, wherein the N subspaces each comprise a cylindrical subspace positioned concentrically with respect to the central string.

3. A machine-implemented method for simulating placement of a plurality of unplaced particles, the method comprising:

selecting a plurality of unplaced particles;
wherein each of the plurality of unplaced particles exhibits a characteristic dimension, corresponding to N categories of the plurality of unplaced particles;
wherein the characteristic dimension of each of the plurality of unplaced particles of a given category of the N categories is different from the characteristic dimension of each of the plurality of unplaced particles of other of the N categories;
defining a central string, a space disposed about the central string, and N subspaces disposed about the central string and within the space, wherein each of the N subspaces corresponds to one of the N categories, respectively;
selecting a particle from the plurality of unplaced particles;
defining a catch net representative of a buoyancy of a portion of a plurality of placed particles and positioning the catch net within the space based upon placement of the portion of the plurality of placed particles;
simulating placement of the selected particle within a corresponding subspace so that the selected particle is positioned in a non-overlapping relationship with respect to the plurality of placed particles and the catch net; and
repeatedly selecting another particle from the plurality of unplaced particles and simulating placement thereof until placement of each of the plurality of unplaced particles has been simulated.

4. The method as recited in claim 3, wherein each of the plurality of unplaced particles comprises a sphere and the characteristic dimension of each of the plurality of unplaced particles comprises a radius.

5. The method as recited in claim 3, wherein selecting the particle from the plurality of unplaced particles comprises randomly selecting the particle from the plurality of unplaced particles.

6. The method as recited in claim 3, further comprising:
defining a pack surface for the plurality of placed particles; and
positioning the catch net relative to a position of the pack surface.

7. The method as recited in claim 6, wherein positioning the catch net relative to the pack surface comprises positioning the catch net at a distance away from the pack surface based upon a selected particle radius.

8. The method as recited in claim 6, wherein:
the plurality of placed particles include a top layer; and
the position of the pack surface comprises an average of a particle location of each of the plurality of placed particles in the top layer thereof.

9. The method as recited in claim 6, wherein:
each of the plurality of placed particles has a south pole;
the plurality of placed particles include a top layer; and
the pack surface corresponds to the south poles of the top layer of the plurality of placed particles.

10. The method as recited in claim 9, wherein the pack surface corresponds to an average of the south pole positions of each of the plurality of placed particles of the top layer.

11. The method as recited in claim 6, wherein the pack surface defining comprises:
selecting a top layer of the placed particles;
for each particle category k of the placed particles in the top layer, defining a particle radius $a_i$ for the placed particles i of that category k;
for subspace k corresponding to the particle category k, assigning a cylinder radius $W_k$;
assigning a top layer particle number m(k) and determining values for m(k) by evaluating $$\sum_{\substack{i=1 \\ Submode(i) \leq k}}^{m(k)-1} a_i^2 < W_k^2 \leq \sum_{\substack{i=1 \\ Submode(i) \leq k}}^{m(k)} a_i^2 \cdot k = 1, 2, \ldots, N$$

where N is a number of particle categories; and
determining the pack surface location using $$S = \frac{1}{m}\sum_{i=1}^{m}(Z_i - a_i)$$

where S represents the pack surface and $Z_i$ represents a position of a center of a center one of the placed particles.

12. The method as recited in claim 6, wherein:
for a given particle category k and corresponding subspace k, the particle placement comprises contacting an ith placed particle with the selected particle, the ith placed particle having a characteristic dimension $a_i$ and the selected particle having a characteristic dimension $a_c$;
the catch net comprises a subnet corresponding to the subspace k; and
if $a_i/a_c < 1$, then the catch net positioning comprises positioning the subnet k for a kth subspace $Z_{net}(k)$ at $$Z_{net}(k) = S - a_i$$

where S represents the position of the pack surface.

13. The method as recited in claim 6, wherein:
for a given particle category k and corresponding subspace k, the particle placement comprises contacting an ith placed particle with the selected particle, the ith placed particle having a characteristic dimension $a_i$ and the selected particle having a characteristic dimension $a_c$;
the catch net comprises a subnet corresponding to the subspace k; and
if $1 \leq a_i/a_c < a_x$, where $a_x$ represents a sample particle size for a corresponding sample particle that will fit into a cavity formed by placed spheres larger than the sample particle, then the catch net positioning comprises positioning a subnet k for a kth subspace $Z_{net}(k)$ at $$Z_{net}(k) = S - 2a_c$$

where S represents the position of the pack surface.

14. The method as recited in claim 13, wherein the sample particle size $a_x$ is assigned a value of $\sqrt{6}+2$.

15. The method as recited in claim 6, wherein:
for a given particle category k and corresponding subspace k, the particle placement comprises contacting an ith placed particle with the selected particle, the ith placed particle having a characteristic dimension $a_i$ and the selected particle having a characteristic dimension $a_c$;
the catch net comprises a subnet corresponding to the subspace k; and
if $a_i/a_c \geq a_x$, where $a_x$ represents a sample particle size for a corresponding sample particle that will fit into a cavity formed by placed spheres larger than the sample particle, then the catch net positioning comprises positioning a subnet k for a kth subspace $Z_{net}(k)$ at $$Z_{net}(k)=S-2a_c-a_i$$

where S represents the position of the pack surface.

16. The method as recited in claim 3, wherein:
the catch net extends across the space substantially perpendicularly to the central string.

17. The method as recited in claim 3, wherein:
the catch net extends across each of the N subspaces substantially perpendicularly to the central string.

18. The method as recited in claim 3, wherein:
each of the N subspaces extends substantially perpendicularly to the central string;
the catch net comprises N subnets; and
each of the N subnets corresponds to each of the N subspaces, respectively.

19. The method as recited in claim 18, wherein each of the N subnets extends across a corresponding subspace of the N subspaces.

20. The method as recited in claim 19, wherein:
each of the N subnets has a level; and
the levels of at least two of the N subnets differ from one another.

21. The method as recited in claim 20, wherein positioning the catch net comprises positioning each of the N subnets at a selected distance from an end of the central string.

22. The method as recited in claim 3, wherein:
the space includes a base surface; and
positioning the catch net comprises spacing the catch net away from the base surface.

23. The method as recited in claim 22, wherein spacing the catch net away from the base surface simulates a positioning of the catch net for a top layer of the placed particles.

24. The method as recited in claim 3, wherein positioning the catch net comprises:
positioning the catch net for a $k_{th}$ one of the N unplaced particle categories at a catch net position $Z_{net}(k)$ within a $k_{th}$ one of the N subspaces determined by $Z_{net}(k)=Z_{init}+H\ r\ a_k\ a_{min}/a_{max}$;
wherein:
$Z_{init}$ is an initial catch net position for a $k_{th}$ one of the N subspaces;
$a_k$ is a characteristic dimension of the particles of a $k_{th}$ one of the N unplaced particle categories;
$a_{min}$ is a characteristic dimension of a small one of the particles;
$a_{max}$ is a characteristic dimension of a large one of the particles;
r is a weighting coefficient; and
H is a switching coefficient.

25. The method as recited in claim 24, wherein the weighting coefficient is assigned a random number.

26. The method as recited in claim 24, wherein:
below a threshold value the switching coefficient is assigned a value of one; and
above the threshold value the switching coefficient is assigned a value of zero.

27. An apparatus for simulating placement of a plurality of unplaced particles, comprising:
an input device for inputting particle selection information;
a storage device operatively coupled to the input device for storing the particle selection information; and
a processor for repeatedly selecting a particle from the plurality of unplaced particles, for simulating placement of the selected particle within a space in a non-overlapping relationship with respect to previously placed particles to form a plurality of placed particles, and for establishing a catch net representative of buoyancy of a portion of the plurality of placed particles and positioning the catch net within a space based upon placement of the portion of the plurality of placed particles, the processor configured for placing the selected particle in non-overlapping relationship with respect to the catch net.

28. A machine-readable medium for use in simulating the placement of a plurality of unplaced particles, comprising:
machine executable instructions for defining a central string, a space disposed about the central string, and N subspaces disposed about the central string and within the space, each of the N subspaces corresponding to one of N categories of the plurality of particles, wherein each of the N categories corresponds to a characteristic dimension of the plurality of unplaced particles;
wherein the machine executable instructions are configured for repeatedly selecting a particle from the plurality of unplaced particles and simulating placement of the selected particle in a subspace of the N subspaces corresponding to the one category of N categories in a non-overlapping relationship with previously placed particles, to form a plurality of placed particles; and
wherein the machine executable instructions are configured for defining a catch net representative of buoyancy of a portion of the plurality of placed particles and positioning the catch net within the space based upon the placement of the portion of the plurality of placed particles, the selected particle being placed in non-overlapping relation with respect to the catch net.

29. A machine-implemented method for simulating placement of a plurality of particles, the method comprising:
selecting a plurality of unplaced particles;
wherein each of the plurality of unplaced particles exhibits a characteristic dimension, corresponding to N categories of the plurality of unplaced particles;
wherein the characteristic dimension of each of the plurality of unplaced particles of a given category of the N categories is different from the characteristic dimension of each of the plurality of particles of other of the N categories;
defining a central string, a space disposed about the central string, and N subspaces disposed about the central string and within the space, wherein each of the N subspaces corresponds to one of the N categories;
selecting a particle from the plurality of unplaced particles;
defining a water level representative of a level of a portion of a plurality of placed particles that are smaller than the selected particle;
simulating placement of the selected particle within a corresponding subspace so that the selected particle is positioned in a non-overlapping relationship with respect to the plurality of placed particles and the water level; and
repeatedly selecting another particle from the plurality of unplaced particles and simulating placement thereof until each of the particles of the plurality of unplaced particles has been simulated.

30. The method as recited in claim 29, wherein each of the plurality of unplaced particles comprises a sphere and the characteristic dimension of each of the plurality of unplaced particles comprises a radius.

31. The method as recited in claim 29, wherein:

defining the water level comprises determining an average location of the particle locations along the central string of the plurality of placed particles and positioning the water level at the average location.

32. The method as recited in claim 29, wherein:

the water level comprises a plurality of subspace water levels wherein each of the plurality of subspace water levels corresponds to one of the N subspaces, respectively; and further comprising positioning the water level comprising positioning each of the plurality of subspace water levels.

33. The method as recited in claim 32, wherein:

each of the N subspaces comprises a subspace surface representative of a portion of placed particles therein, each of the subspace surfaces comprising a subspace surface location with respect to the central string;

each of the plurality of placed particles comprises a north pole having a north pole location; and the subspace water level position for one of the subspaces is determined by determining an average location of the north pole locations of the portion of the plurality of placed particles within the one subspace and assigning the average location of the subspace surface location for the one subspace.

34. The method as recited in claim 32, wherein:

each of the N subspaces comprises a subspace surface representative of a portion of smaller placed particles within that subspace, each of the subspace surfaces comprising a subspace surface location with respect to the central string;

each of the plurality of placed particles comprises a south pole having a south pole location; and the subspace water level position for one of the subspaces is determined by determining an average location of the south pole locations of the portion of the plurality of placed particles within the one subspace and assigning the average location as the subspace surface location for the one subspace.

35. The method as recited in claim 32, wherein:

positioning the water level comprises using an offset for each of the subspace water level positions.

36. The method as recited in claim 29, wherein:

defining the water level comprises using an offset to position the water level.

37. An apparatus for simulating placement of a plurality of unplaced particles, comprising:

an input device for inputting particle selection information;

a storage device operatively coupled to the input device for storing the particle selection information; and a processor for selecting a particle from the plurality of particles, for placing the selected particle in the corresponding subspace so that the selected particle becomes a placed particle at a particle location unique to that placed particle and is in non-overlapping relation with other placed particles, for establishing a water level representative of a level of a portion of the placed particles that are smaller than the selected particle and represent a surface of the smaller placed particles, and for positioning the water level within the space based upon the smaller particle surface, the selected particle being placed in non-overlapping relation with respect to the water level.

38. A machine-readable medium for use in simulating placement of a plurality of unplaced particles, comprising:

machine executable instructions for defining a central string, a space disposed about the central string, and N subspaces disposed about the central string and within the space, each of the N subspaces corresponding to one of N particle categories;

wherein the machine executable instructions are configured for repeatedly selecting a particle from the plurality of particles and simulating the placement of the selected particle in a subspace of the N subspaces of the corresponding category of N categories in non-overlapping relation with previously placed particles, to form a plurality of placed particles; and wherein the machine executable are configured for defining a water level representative of a portion of the plurality of placed particles that are smaller than the selected particle and represent a surface of the portion of the plurality of placed particles and for positioning the water level within the space based upon the smaller particle surface, the selected particle being placed in non-overlapping relation with respect to the water level.

39. A machine-implemented method for simulating the placement of a particle, the method comprising:

defining a central string and a space having a cylindrical boundary wall disposed about the central string;

defining a plurality of cylindrical subspaces disposed about the central string and within the space, wherein each of the subspaces has a cylindrical boundary wall;

wherein the space includes a plurality of previously placed particles;

defining a water level representative of a level of a portion of the plurality of previously placed particles having a size which is smaller than a selected particle;

simulating movement of a particle within the space from an initial position and in a selected direction;

simulating contact of the particle with at least one of the cylindrical boundary wall of the space, the water level, the cylindrical wall of one of the plurality of subspaces, and at least one of the plurality of previously placed particles; and determining stable placement of the particle within the space.

40. The method as recited in claim 39, wherein simulating contact of the particle with at least one of the cylindrical boundary wall of the space, the water level, the cylindrical boundary wall of one of the plurality of subspaces, and the at least one of the plurality of previously placed particles comprises simulating rolling of the particle with respect to at least one of the cylindrical boundary wall of the space, the water level, the cylindrical wall of one of the plurality of subspaces, and the at least one of the plurality of previously placed particles.

41. The method as recited in claim 39, wherein simulating contact of the particle with at least one of the cylindrical boundary wall of the space, the water level, the cylindrical boundary wall of one of the plurality of subspaces, and the at least one of the plurality of previously placed particles comprises determining whether contact of the particle with at least one of the cylindrical boundary wall of the space, the water level, the cylindrical boundary wall of one of the plurality of subspaces, and the at least one of the plurality of previously placed particles is compressive or tensile.

42. The method as recited in claim 39, wherein simulating movement of the particle within the space from the initial position and in the selected direction comprises simulating movement of the particle within the space in a direction parallel to the central string.

43. The method as recited in claim 39, wherein simulating movement of the particle within the space from the initial position and in the selected direction comprises constraining a center of the particle to remain within one of the plurality of cylindrical subspaces during simulating movement thereof.

44. The method as recited in claim 39, further comprising:
defining a catch net representative of buoyancy of a portion of the plurality of placed particles and positioning the catch net within the space based upon the placement of the portion of the plurality of placed particles.

45. A machine-implemented method for simulating the placement of a particle, the method comprising:
defining a central string and a space having a cylindrical boundary wall disposed about the central string;
defining a plurality of cylindrical subspaces disposed about the central string and within the space, wherein each of the subspaces has a cylindrical boundary wall;
wherein the space includes a plurality of previously placed particles;
defining a catch net representative of a buoyancy of a portion of the plurality of previously placed particles and positioning the catch net within the space based upon the placement of the portion of the plurality of previously placed particles;
simulating movement of a particle within the space from an initial position and in a selected direction;
simulating contact of the particle with at least one of the cylindrical boundary wall of the space, the catch net, the cylindrical boundary wall of one of the plurality of subspaces, and at least one of the plurality of previously placed particles; and
determining stable placement of the particle within the space.

46. The method as recited in claim 45, wherein simulating contact of the particle with at least one of the cylindrical boundary wall of the space, the catch net, the cylindrical boundary wall of one of the plurality of subspaces, and the at least one of the plurality of previously placed particles comprises simulating rolling of the particle with respect to at least one of the cylindrical boundary wall of the space, the catch net, the cylindrical boundary wall of one of the plurality of subspaces, and the at least one of the plurality of previously placed particles.

47. The method as recited in claim 45, wherein simulating contact of the particle with at least one of the cylindrical boundary wall of the space, the catch net, the cylindrical boundary wall of one of the plurality of subspaces, and the at least one of the plurality of previously placed particles comprises determining whether contact of the particle with at least one of the cylindrical boundary wall of the space, the catch net, the cylindrical boundary wall of one of the plurality of subspaces, and the at least one of the plurality of previously placed particles is compressive or tensile.

48. The method as recited in claim 45, wherein simulating movement of the particle within the space from the initial position and in the selected direction comprises simulating movement of the particle within the space in a direction parallel to the central string.

49. The method as recited in claim 45, wherein simulating movement of the particle within the space from the initial position and in the selected direction comprises constraining a center of the particle to remain within one of the plurality of cylindrical subspaces during simulating movement thereof.

50. The method as recited in claim 45, further comprising:
defining a water level representative of a level of a portion of the plurality of previously placed particles having a size which is smaller than the selected particle.

* * * * *

UNITED STATES PATENT AND TRADEMARK OFFICE
CERTIFICATE OF CORRECTION

PATENT NO. : 7,085,689 B2
APPLICATION NO. : 09/805606
DATED : August 1, 2006
INVENTOR(S) : I. Lee Davis and Michael P. Iverson It is certified that error appears in the above-identified patent and that said Letters Patent is hereby corrected as shown below:

| | | |
|---|---|---|
| COLUMN 5, | LINE 61, | change "accordind" to --according-- |
| COLUMN 7, | LINE 11, | change ""Machine"," to --"Machine,"-- |
| COLUMN 13, | LINE 42, | change "terns" to --terms-- |
| COLUMN 13, | LINE 57, | change "andj" to --and j-- |
| COLUMN 23, | LINE 38, | change "ie.," to --i.e.,-- |
| COLUMN 32, | LINE 26, | change "ftirther" to --further-- |
| COLUMN 39, | LINE 50, | change "+ $\sin\theta_{ji} \sin\varphi_{ji} \cos\theta_c'$) (84b)" to --+ $\sin\theta_{ji} \sin\varphi_{ji} \cos\theta_c'$). (84b)-- |
| COLUMN 41, | LINE 6, | change "cos(θ9$_c$0a)" to --cosθ$_c$ (90a)-- |
| COLUMN 44, | LINE 5, | change "cos(θ'1$_c$]08b)" to --cosθ$_c$'](108b)-- |
| COLUMN 49, | LINE 68, | change "sin$\Phi_c$)]$^1$($^2$1.47)" to --sin$\Phi_c$)]$^{1/2}$. (147)-- |
| COLUMN 54, | LINE 8, | change "And" to --and-- |
| COLUMN 56, | LINE 31, | change "fuiction" to --function-- |
| COLUMN 64, | LINE 24, | change "a re" to --are-- |
| COLUMN 64, | LINE 24, | change "pl e" to --pole-- |

Signed and Sealed this

Sixth Day of October, 2009

David J. Kappos
*Director of the United States Patent and Trademark Office*